US009539320B2

(12) United States Patent
Hadden et al.

(10) Patent No.: US 9,539,320 B2
(45) Date of Patent: Jan. 10, 2017

(54) VACCINE IMMUNOTHERAPY

(75) Inventors: John W. Hadden, Cold Spring Harbor, NY (US); Kathy Signorelli, Kings Park, NY (US); James Egan, New York, NY (US); Paul Naylor, New York, NY (US)

(73) Assignee: IRX Therapeutics, Inc., New York, NY (US)

( * ) Notice: Subject to any disclaimer, the term of this patent is extended or adjusted under 35 U.S.C. 154(b) by 0 days.

(21) Appl. No.: 13/320,584

(22) PCT Filed: May 17, 2010

(86) PCT No.: PCT/US2010/035060
§ 371 (c)(1),
(2), (4) Date: Nov. 15, 2011

(87) PCT Pub. No.: WO2010/132867
PCT Pub. Date: Nov. 18, 2010

(65) Prior Publication Data
US 2012/0064035 A1    Mar. 15, 2012

Related U.S. Application Data

(60) Provisional application No. 61/178,741, filed on May 15, 2009.

(51) Int. Cl.
*A61K 45/00* (2006.01)
*A61K 39/39* (2006.01)
(Continued)

(52) U.S. Cl.
CPC ............. *A61K 39/39* (2013.01); *A61K 38/164* (2013.01); *A61K 38/177* (2013.01);
(Continued)

(58) Field of Classification Search
CPC ..................................................... A61K 45/00
See application file for complete search history.

(56) References Cited

U.S. PATENT DOCUMENTS 4,079,127 A    3/1978 Goldstein et al.
4,116,951 A    9/1978 Wang
(Continued)

FOREIGN PATENT DOCUMENTS

CN    1106297 A     8/1995
EP    0 041 189 A1  12/1981
(Continued)

OTHER PUBLICATIONS

Coles, et al., (J Pharma Pharmacol. 1965. 17, Suppl., 87S-91S).*
(Continued)

*Primary Examiner* — Cherie M Stanfield
(74) *Attorney, Agent, or Firm* — Wolf, Greenfield & Sacks, P.C.

(57) ABSTRACT

A composition for treating cancer, including synergistic amounts of a primary cell-derived biologic having the cytokines IL-1, IL-2, IL-6, IL-8, TNF-α, and IFN-γ, and a cancer vaccine having at least one antigen. A composition comprising synergistic amounts of the primary cell-derived biologic in combination with at least one adjuvant. A method of treating cancer by administering the composition. A method of reversing immune suppression and gaining immunity to cancer. A method of producing an immune response to an exogenous antigen. A method of enhancing an immune response in a patient by administering the primary cell-derived biologic in combination with at least one adjuvant, and enhancing the immune response of the patient by a synergistic interaction of the primary cell-derived biologic and the adjuvant. A method of increasing function of an immune system.

11 Claims, 59 Drawing Sheets

In-vivo CTL Assay with labelled peptide-pulsed splenocytes

• The CTL assay shows *in vivo* killing of 24% of the target cells in mice vaccinated in the absence of IRX-2, increased to 63% in mice vaccinated in the presence of IRX-2

Legend :
E = emulsion
O = Ova peptides
P = Poly I:C
C = CpG
I = IFN-Gamma
M = IRX-2 included in the vaccine

(51) Int. Cl.
  *A61K 38/16* (2006.01)
  *A61K 38/17* (2006.01)
  *A61K 38/19* (2006.01)
  *A61K 38/20* (2006.01)
  *A61K 38/21* (2006.01)
  *A61K 39/00* (2006.01)
  *A61K 45/06* (2006.01)
  *A61K 39/395* (2006.01)

(52) U.S. Cl.
  CPC .......... *A61K 38/191* (2013.01); *A61K 38/193* (2013.01); *A61K 38/204* (2013.01); *A61K 38/2006* (2013.01); *A61K 38/208* (2013.01); *A61K 38/2013* (2013.01); *A61K 38/2053* (2013.01); *A61K 38/217* (2013.01); *A61K 39/0011* (2013.01); *A61K 39/39558* (2013.01); *A61K 45/06* (2013.01); *A61K 2039/55522* (2013.01); *A61K 2039/55561* (2013.01); *A61K 2039/55588* (2013.01); *A61K 2039/6081* (2013.01)

(56) References Cited

U.S. PATENT DOCUMENTS

| | | |
|---|---|---|
| 4,148,788 A | 4/1979 | Wang |
| 4,293,455 A | 10/1981 | Merrifield et al. |
| 4,353,821 A | 10/1982 | Birr et al. |
| 4,390,623 A | 6/1983 | Frabricius et al. |
| 4,406,830 A | 9/1983 | Fabricius et al. |
| 4,448,879 A | 5/1984 | Fabricius et al. |
| 4,464,355 A | 8/1984 | Fabricius et al. |
| 4,466,918 A | 8/1984 | Birr et al. |
| 4,470,926 A | 9/1984 | Birr et al. |
| 4,504,415 A | 3/1985 | Felix et al. |
| 4,612,365 A | 9/1986 | Birr et al. |
| 4,614,731 A | 9/1986 | Horecker |
| 4,659,694 A | 4/1987 | Horecker |
| 4,716,148 A | 12/1987 | Horecker |
| 4,910,296 A | 3/1990 | Birr et al. |
| 5,098,702 A | 3/1992 | Zimmerman et al. |
| 5,100,664 A | 3/1992 | Doyle et al. |
| 5,503,828 A | 4/1996 | Testa et al. |
| 5,503,841 A | 4/1996 | Doyle et al. |
| 5,632,983 A * | 5/1997 | Hadden ........................ 424/85.1 |
| 5,643,565 A | 7/1997 | Doyle et al. |
| 5,679,356 A | 10/1997 | Bonnem et al. |
| 5,698,194 A | 12/1997 | Hadden |
| 5,747,024 A | 5/1998 | Grabstein et al. |
| 5,788,963 A | 8/1998 | Murphy et al. |
| 5,800,810 A | 9/1998 | Doyle et al. |
| 5,849,307 A | 12/1998 | Metz et al. |
| 5,849,589 A | 12/1998 | Tedder et al. |
| 5,866,115 A | 2/1999 | Kanz et al. |
| 6,017,527 A | 1/2000 | Maraskovsky et al. |
| 6,060,068 A | 5/2000 | Doyle et al. |
| 6,274,378 B1 | 8/2001 | Steinman et al. |
| 6,350,589 B1 | 2/2002 | Morris et al. |
| 6,482,389 B1 | 11/2002 | Hadden |
| 6,759,239 B2 | 7/2004 | Suciu-Foca et al. |
| 6,896,879 B2 | 5/2005 | Talor |
| 6,977,072 B2 | 12/2005 | Hadden |
| 7,153,499 B2 | 12/2006 | Hadden |
| 7,182,942 B2 | 2/2007 | Hadden |
| 7,374,751 B1 * | 5/2008 | Hancock ...................... 424/85.2 |
| 7,731,945 B2 | 6/2010 | Hadden |
| 7,993,660 B2 | 8/2011 | Hadden et al. |
| 8,470,562 B2 | 6/2013 | Fennington, Jr. et al. |
| 8,591,956 B2 | 11/2013 | Hadden et al. |
| 8,784,796 B2 | 7/2014 | Hadden |
| 9,333,238 B2 | 5/2016 | Egan et al. |
| 2001/0053361 A1 | 12/2001 | Thompson et al. |
| 2002/0034494 A1 | 3/2002 | Vicari et al. |
| 2002/0058019 A1 | 5/2002 | Berenson et al. |
| 2002/0146397 A1 | 10/2002 | Hadden |
| 2002/0159953 A1 | 10/2002 | Hadden |
| 2003/0007955 A1 | 1/2003 | Rees et al. |
| 2003/0206885 A1 | 11/2003 | Hadden |
| 2004/0001829 A1 | 1/2004 | June et al. |
| 2004/0071658 A1 | 4/2004 | Hadden et al. |
| 2004/0136952 A1 | 7/2004 | Bhaskaran et al. |
| 2005/0008614 A1 | 1/2005 | Nieland et al. |
| 2005/0124645 A1 | 6/2005 | Finkel |
| 2005/0152874 A1 | 7/2005 | Hadden |
| 2006/0120996 A1 | 6/2006 | Hadden |
| 2006/0140983 A1 | 6/2006 | Palucka et al. |
| 2006/0194242 A1 | 8/2006 | Hadden |
| 2007/0025958 A1 * | 2/2007 | Hadden ................ A61K 38/217 424/85.1 |
| 2007/0031372 A1 | 2/2007 | Hadden |
| 2007/0041956 A1 | 2/2007 | Hadden |
| 2007/0065415 A1 | 3/2007 | Kleinsek et al. |
| 2007/0128174 A1 | 6/2007 | Kleinsek et al. |
| 2007/0154399 A1 | 7/2007 | Hadden |
| 2007/0196335 A1 | 8/2007 | Pardoll et al. |
| 2007/0259330 A1 | 11/2007 | Goddard et al. |
| 2008/0138365 A1 | 6/2008 | Berinstein et al. |
| 2008/0220000 A1 | 9/2008 | Moore et al. |
| 2009/0041797 A1 | 2/2009 | Davis et al. |
| 2009/0180982 A1 | 7/2009 | Hadden, Sr. |
| 2009/0181078 A1 | 7/2009 | Reed et al. |
| 2009/0258395 A1 | 10/2009 | Fennington, Jr. et al. |
| 2010/0047182 A1 | 2/2010 | Hadden |
| 2010/0047205 A1 | 2/2010 | Hadden et al. |
| 2010/0310469 A1 | 12/2010 | Hadden |
| 2011/0044941 A1 | 2/2011 | Hadden |
| 2011/0076249 A1 | 3/2011 | Hadden et al. |
| 2011/0081313 A1 | 4/2011 | Hadden |
| 2011/0110884 A1 | 5/2011 | Hadden et al. |
| 2012/0141512 A1 | 6/2012 | Hadden et al. |
| 2012/0244117 A1 | 9/2012 | Egan et al. |
| 2013/0164255 A1 | 6/2013 | Hadden et al. |
| 2013/0243723 A1 | 9/2013 | Hadden et al. |
| 2014/0010779 A1 | 1/2014 | Hadden |
| 2014/0010780 A1 | 1/2014 | Hadden |
| 2014/0023593 A1 | 1/2014 | Hadden |
| 2014/0030217 A1 | 1/2014 | Hadden et al. |
| 2014/0348782 A1 | 11/2014 | Hadden |
| 2014/0348783 A1 | 11/2014 | Hadden |

FOREIGN PATENT DOCUMENTS

| | | |
|---|---|---|
| EP | 0 433 765 A1 | 6/1991 |
| EP | 0 974 357 A1 | 1/2000 |
| EP | 0 789 588 B1 | 1/2005 |
| EP | 0 787 008 B1 | 1/2009 |
| EP | 1 653 912 B1 | 10/2011 |
| EP | 1 998 811 B1 | 10/2012 |
| JP | 8-511166 A | 11/1996 |
| JP | 10-509955 | 9/1998 |
| JP | 2002-531521 A | 9/2002 |
| JP | 2008-502605 A | 1/2008 |
| JP | 2009-530308 A | 8/2009 |
| JP | 2009-197032 A | 9/2009 |
| WO | WO 87/06830 A1 | 11/1987 |
| WO | WO 89/09619 A1 | 10/1989 |
| WO | WO 94/13314 A1 | 6/1994 |
| WO | WO 95/04548 A1 | 2/1995 |
| WO | WO 96/15800 A1 | 5/1996 |
| WO | WO 96/15808 A1 | 5/1996 |
| WO | WO 96/34956 A1 | 11/1996 |
| WO | WO 97/31119 A1 | 8/1997 |
| WO | WO 99/20788 A1 | 4/1999 |
| WO | WO 99/40938 A2 | 8/1999 |
| WO | WO 00/06723 A1 | 2/2000 |
| WO | WO 00/33870 A2 | 6/2000 |
| WO | WO 01/24771 A1 | 4/2001 |
| WO | WO 02/34119 A2 | 5/2002 |
| WO | WO 03/035004 A2 | 5/2003 |
| WO | WO 03/061566 A2 | 7/2003 |
| WO | WO 2005/025494 A2 | 3/2005 |
| WO | WO 2005/120550 A2 | 12/2005 |
| WO | WO 2005/123120 A1 | 12/2005 |

(56) References Cited

FOREIGN PATENT DOCUMENTS

| WO | WO 2007/067782 A2 | 6/2007 |
|---|---|---|
| WO | WO 2007/136910 A2 | 11/2007 |
| WO | WO 2008/014220 A2 | 1/2008 |
| WO | WO 2008/101154 A2 | 8/2008 |
| WO | WO 2008/133983 A1 | 11/2008 |
| WO | WO 2009/070639 A1 | 6/2009 |
| WO | WO 2009/137238 A2 | 11/2009 |
| WO | WO 2009/146392 A1 | 12/2009 |
| WO | WO 2010/132867 A1 | 11/2010 |
| WO | WO 2011/072006 A1 | 6/2011 |
| WO | WO 2012/037551 A2 | 3/2012 |

OTHER PUBLICATIONS

Verastequi et al., (Int J Immunopharmacol. Nov.-Dec. 1997;19(11-12):619-27. Abstract Only).*
Eby (Med Hypotheses. 2005;64(6):1124-6).*
Duenas-Gonzalez et al., (Int Immunopharmacol. Jun. 2002;2(7):1007-16. Abstract Only).*
Barrera et al., (Arch Otolaryngol Head Neck Surg. Mar. 2000;126:345-351).*
Hadden, JW (Intl Immunopharmacol.2003;3:1061-1071).*
Albert et al., Dendritic cells acquire antigen from apoptotic cells and induce class I-restricted CTLs. Nature. Mar. 5, 1998;392(6671):86-9.
Almand et al., Clinical significance of defective dendritic cell differentiation in cancer. Clin Cancer Res. May 2000;6(5):1755-66.
Alvarez et al., Human T cell growth factor. I. Optimal conditions for its production. J Immunol. Sep. 1979;123(3):977-83.
Bajénoff et al., Stromal cell networks regulate lymphocyte entry, migration, and territoriality in lymph nodes. Immunity. Dec. 1, 2006;25(6):989-1001.
Banchereau et al. Immunobiology of dendritic cells. Annu Rev Immunol. 2000;18:767-811.
Barrera et al., Clinical and pathological bio-responses induced with a cytokine mixture (IRX-2) in patients with oral cavity squamous cell carcinoma. Clinical and Applied Immunology Rev. 2001;1:181-5.
Barrera et al., Clinical and pathological responses induced by a neoadjuvant treatment with a cytokine mixture (IRX-2) in oral cavity squamous cell carcinoma of head and neck. Int J Immunorehab. 2000;2(3):29-32.
Barrera et al., Neoadjuvant immunological treatment with IRX-2 in patients with advanced oral cavity squamous cell carinoma of the head and neck induces clinical and histological responses. First World Congress on Head and Neck Oncology. 1998:1017-20.
Barrera et al., Nursing care makes a difference. Application of the Omaha System. Outcomes Manag. Oct.-Dec. 2003;7(4):181-5.
Belldegrun et al., Adoptive immunotherapy of urologic tumors. Urologic Oncology. Cancer Treatment and Research. 1989;46:213-33.
Belldegrun et al., Human tumor infiltrating lymphocytes. Analysis of lymphokine mRNA expression and relevance to cancer immunotherapy. J Immunol. Jun. 15, 1989;142(12):4520-6.
Bellone et al., Cancer immunotherapy: synthetic and natural peptides in the balance. Immunol Today. Oct. 1999;20(10):457-62.
Bellone et al., Processing of engulfed apoptotic bodies yields T cell epitopes. J Immunol. Dec. 1, 1997;159(11):5391-9.
Bender et al., Improved methods for the generation of dendritic cells from nonproliferating progenitors in human blood. J Immunol Methods. Sep. 27, 1996;196(2):121-35.
Berd et al., Effect of low dose cyclophosphamide on the immune system of cancer patients: reduction of T-suppressor function without depletion of the CD8+ subset. Cancer Res. Jun. 15, 1987;47(12):3317-21.
Berd et al., Potentiation of human cell-mediated and humoral immunity by low-dose cyclophosphamide. Cancer Res. Nov. 1984;44(11):5439-43.

Berd, Low doses of chemotherapy to inhibit suppressor T cells. Immunity to Cancer II. 1989;288:449-58.
Beuth et al., Thymosin alpha(1) application augments immune response and down-regulates tumor weight and organ colonization in BALB/c-mice. Cancer Lett. Oct. 16, 2000;159(1):9-13.
Borden, Interferons: rationale for clinical trials in neoplastic disease. Ann Intern Med. Sep. 1979;91(3):472-9. Review.
Borysiewicz et al., A recombinant vaccinia virus encoding human papillomavirus types 16 and 18, E6 and E7 proteins as immunotherapy for cervical cancer. Lancet. Jun. 1, 1996;347(9014):1523-7.
Brandwein, IRX-2: a natural cytokine stimulant for cancer vaccines. Session V: Strategies for immunization. Cancer Immunol Immunotherapy. Mar. 2003;52:S17-18, 30.
Cella et al., Inflammatory stimuli induce accumulation of MHC class II complexes on dendritic cells. Nature. Aug. 21, 1997;388(6644):782-7.
Cella et al., Ligation of CD40 on dendritic cells triggers production of high levels of interleukin-12 and enhances T cell stimulatory capacity: T-T help via APC activation. J Exp Med. Aug. 1, 1996;184(2):747-52.
Chang et al., Overview of interleukin-2 as an immunotherapeutic agent. Semin Surg Oncol. 1989;5(6):385-90. Review.
Chaux et al., Inflammatory cells infiltrating human colorectal carcinomas express HLA class II but not B7-1 and B7-2 costimulatory molecules of the T-cell activation. Lab Invest. May 1996;74(5):975-83.
Chilson et al., Mitogenic lectins bind to the antigen receptor on human lymphocytes. Eur J Immunol. Feb. 1989;19(2):389-96.
Chirigos et al., Immunotherapeutic agents: their role in cellular immunity and their therapeutic potential. Springer Semin Immunopathol.1985;8(4):327-46.
Cirelli et al., Interferons in human papillomavirus infections. Antiviral Res. Jul. 1994;24(2- 3):191-204.
Clerici et al., An Occam's razor approach to the immunopathogenesis of HIV infection. AIDS. 1995;9 Suppl A:S33-40.
Cohen et al., Pronounced acute immunosuppression in vivo mediated by HIV Tat challenge. Proc Natl Acad Sci U S A. Sep. 14, 1999;96(19):10842-7.
Cortesina et al., Interleukin-2 injected around tumor-draining lymph nodes in head and neck cancer. Head Neck. Mar.-Apr. 1991;13(2):125-31.
Cortesina et al., Temporary regression of recurrent squamous cell carcinoma of the head and neck is achieved with a low but not with a high dose of recombinant interleukin 2 injected perilymphatically. Br J Cancer. Mar. 1994;69(3):572-6.
Cortesina et al., Treatment of recurrent squamous cell carcinoma of the head and neck with low doses of interleukin-2 injected perilymphatically. Cancer. Dec. 15, 1988;62(12):2482-5.
Cowens et al., Inhibition of the development of suppressor cells in culture by 4- hydroperoxycyclophosphamide. J Immunol. 1984;132:95-100.
Cozzolino et al., Characterization of cells from invaded lymph nodes in patients with solid tumors. Lymphokine requirement for tumor-specific lymphoproliferative response. J Exp Med. Aug. 1, 1987;166(2):303-18.
Cross et al., Administration of a prostaglandin synthetase inhibitor associated with an increased immune cell infiltrate in squamous cell carcinoma of the head and neck. Arch Otolaryngol Head Neck Surg. May 1992;118(5):526-8.
Czystowska et al., Mechanisms of T-cell protection from death by IRX-2: a new immunotherapeutic. Cancer Immunol Immunother. Apr. 2011;60(4):495-506. doi: 10.1007/s00262010-0951-9. Epub Dec. 23, 2010.
Dallal et al., The dendritic cell and human cancer vaccines. Curr Opin Immunol. Oct. 2000;12(5):583-8.
De Stefani et al., Improved survival with perilymphatic interleukin 2 in patients with resectable squamous cell carcinoma of the oral cavity and oropharynx. Cancer. Jul. 1, 2002;95(1):90-7.
De Vries et al., Effective migration of antigen-pulsed dendritic cells to lymph nodes in melanoma patients is determined by their maturation state. Cancer Res. Jan. 1, 2003;63(1):12-7.

(56) References Cited

OTHER PUBLICATIONS

Deans et al., CD45R as a primary signal transducer stimulating IL-2 and IL-2R mRNA synthesis by CD3-4-8- thymocytes. J Immunol. Oct. 15, 1989;143(8):2425-30.
Deepe et al., Pharmacological modulation of suppressor cell activity in mice with disseminated histoplasmosis. Infect Immun. Jul. 1983;41(1):114-20.
Den Otter et al., Local therapy of cancer with free IL-2. Cancer Immunol Immunother. Jul. 2008;57(7):931-50. doi: 10.1007/s00262-008-0455-z.
Dunn et al., Dendritic cells and HNSCC: a potential treatment option? Oncology Reports. 2005;13:3-10.
Egan et al., IRX-2, a novel in vivo immunotherapeutic, induces maturation and activation of human dendritic cells in vitro. J Immunotherapy. 2007;30(6):624-33.
Ehrke, Immunomodulation in cancer therapeutics. Int Immunopharmacol. Aug. 2003;3(8):1105-19.
Favalli et al., Modulation of natural killer activity by thymosin alpha 1 and interferon. Cancer Immunol Immunother. 1985;20(3):189-92.
Ferraro et al., Co-delivery of PSA and PSMA DNA vaccines with electroporation induces potent immune responses. Hum Vaccin. Jan.-Feb. 2011;7 Suppl:120-7. Epub Jan. 1, 2011.
Forni et al., Interleukin 2 activated tumor inhibition in vivo depends on the systemic involvement of host immunoreactivity. J Immunol. Jun. 1, 1987;138(11):4033-41.
Frillingos et al., Appearance of thymosin alpha 1 in supernatants of monocytes incubated with prothymosin alpha. Arch Biochem Biophys.Jul. 1992;296(1):256-63.
Gabrilovich et al., Decreased antigen presentation by dendritic cells in patients with breast cancer. Clin Cancer Res. Mar. 1997;3(3):483-90.
Gabrilovich et al., Dendritic cells in antitumor immune responses. I. Defective antigen presentation in tumor-bearing hosts. Cell Immunol. May 25, 1996;170(1):101-10.
Gabrilovich et al., Production of vascular endothelial growth factor by human tumors inhibits the functional maturation of dendritic cells. Nat Med. Oct. 1996;2(10):1096-103.
Gabrilovich et al., Vascular endothelial growth factor inhibits the development of dendritic cells and dramatically affects the differentiation of multiple hematopoietic lineages in vivo. Blood. Dec. 1, 1998;92(11):4150-66.
Gallo et al., Cyclooxygenase-2 pathway correlates with VEGF expression in head and neck cancer. Implications for tumor angiogenesis and metastasis. Neoplasia. Jan.-Feb. 2001;3(1):53-61.
Galon et al., Type, density, and location of immune cells within human colorectal tumors predict clinical outcome. Science. Sep. 29, 2006;313(5795):1960-4.
Garaci et al., Thymosin alpha 1 in the treatment of cancer: from basic research to clinical application. Int J Immunopharmacol. Dec. 2000;22(12):1067-76. Review.
Garaci, Thymosin alpha1: a historical overview. Ann N Y Acad Sci. Sep. 2007;1112:14-20. Epub Jun. 13, 2007.
Gearing et al., Production and assay of the interleukins. J Immunol Methods. Oct. 24, 1985;83(1):1-27.
Gillis et al., T cell growth factor: parameters of production and a quantitative microassay for activity. J Immunol. Jun. 1978;120(6):2027-32.
Goldstein et al., The role of interferon in cancer therapy: a current perspective. CA Cancer J Clin. Sep.-Oct. 1988;38(5):258-77.
Goldstein et al., Thymosin alpha1: isolation and sequence analysis of an immunologically active thymic polypeptide. Proc Natl Acad Sci U S A. Feb. 1977;74(2):725-9.
Goldstein, Thymosin α1: chemistry, mechanism of action and clinical applications. Combination Therapies. Plenum Press. 1993;2:39-48.
Gollapudi et al, Effect of ciprofloxacin on mitogen-stimulated lymphocyte proliferation. Antimicrob Agents Chemother. Feb. 1986;29(2):337-8.

Hadden et al., A trial of IRX-2 in patients with squamous cell carcinomas of the head and neck. Int Immunopharmacol. Aug. 2003;3(8):1073-81.
Hadden et al., Immunopharmacologic bases of immunotherapy. Clin Physiol Biochem. 1985;3(2-3):111-9. Review.
Hadden et al., Immunopharmacology. Immunomodulation and immunotherapy. JAMA. Nov. 25, 1992;268(20):2964-9.
Hadden et al., Immunotherapy with natural interleukins and/or thymosin alpha 1 potently augments T-lymphocyte responses of hydrocortisone-treated aged mice. Int J Immunopharmacol. Oct. 1995;17(10):821-8.
Hadden et al., Interleukins and contrasuppression induce immune regression of head and neck cancer. Arch Otolaryngol Head Neck Surg. Apr. 1994;120(4):395-403.
Hadden et al., IRX-2 and thymosin alpha1 (Zadaxin) increase T lymphocytes in T lymphocytopenic mice and humans. Ann N Y Acad Sci. Sep. 2007;1112:245-55. Epub Jun. 28, 2007.
Hadden et al., Lymphocyte blast transformation. I. Demonstration of adrenergic receptors in human peripheral lymphocytes. Cell Immunol. Dec. 1970;1(6):583-95.
Hadden et al., Mixed interleukins and thymosin fraction V synergistically induce T lymphocyte development in hydrocortisone-treated aged mice. Cell Immunol. Oct. 1, 1992;144(1):228-36.
Hadden et al., Strategies of immune reconstitution: effects of lymphokines on murine T cell development in vitro and in vivo. Life Sci. 1989;44(13):v-xii.
Hadden et al., The characterization of immunotherapeutic agents. Immunopharmacol Reviews. Plenum Press. New York. 1990;1:1-64.
Hadden, Aspects of the immunopharmacology of thymosin alpha-1. Clinical Applied Reviews. Mar. 2001;1(3-4):187-91.
Hadden, Combination immunotherapy. Intl Immunopharm. 2003;3:1049-50.
Hadden, Immunology of Head and Neck Cancer. Contemporary Issues in Oral Cancer. New York. Oxford University Press. 2000:72-95.
Hadden, Immunology of head and neck cancer: prospects for immunotherapy. Clin Immunotherapy. 1995;3:362-85.
Hadden, Immunopharmacology. Immunomodulation and immunotherapy. JAMA. Nov. 27, 1987;258(20):3005-10.
Hadden, Immunostimulants. Immunol Today. Jun. 1993;14(6):275-80. Review.
Hadden, Immunotherapy of human immunodeficiency virus infection. TIPS review. 1991;12:107-11.
Hadden, T-cell adjuvants. Int J Immunopharmacol. Sep. 1994;16(9):703-10.
Hadden, The immunology and immunotherapy of breast cancer: an update. Int J Immunopharmacol. Feb. 1999;21(2):79-101.
Hadden, The immunopharmacology of head and neck cancer: an update. Int J Immunopharmacol. Nov.-Dec. 1997;19(11-12):629-44.
Hadden, The treatment of zinc deficiency is an immunotherapy. Int J Immunopharmacol. Sep. 1995;17(9):697-701.
Hadden, Thymic endocrinology. Ann N Y Acad Sci. May 1, 1998;840:352-8.
Hadden, Thymic endocrinology. Int J Immunopharmacol. Apr. 1992;14(3):345-52. Review.
Hank et al., Monoclonal antibodies, cytokines and fusion proteins in the treatment of malignant disease. Cancer Chemother Biol Response Modif. 1999;18:210-22.
Hart, Dendritic cells: unique leukocyte populations which control the primary immune response. Blood. Nov. 1, 1997;90(9):3245-87.
Hengst et al., Cooperation between cyclophosphamide tumoricidal activity and host antitumor immunity in the cure of mice bearing large MOPC-315 tumors. Cancer Res. Jun. 1981;41(6):2163-7.
Hengst et al., Importance of timing in cyclophosphamide therapy of MOPC-315 tumor-bearing mice. Cancer Res. Jul. 1980;40(7):2135-41.
Hillman et al., Systemic treatment with interleukin-4 induces regression of pulmonary metastases in a murine renal cell carcinoma model. Cell Immunol. Feb. 1995;160(2):257-63.
Hirsch et al., Immunostimulation of patients with head and neck cancer. In vitro and preliminary clinical experiences. Arch Otolaryngol. May 1983;109(5):298-301.

(56) References Cited

OTHER PUBLICATIONS

Hoffmann et al., Alterations in the frequency of dendritic cell subsets in the peripheral circulation of patients with squamous cell carcinomas of the head and neck. Clin Cancer Res. Jun. 2002;8(6):1787-93.

Holtl et al., Immunotherapy of metastatic renal cell carcinoma with tumor lysate-pulsed autologous dendritic cells. Clin Cancer Res. Nov. 2002;8(11):3369-76.

Hwu et al., The genetic modification of T cells for cancer therapy: an overview of laboratory and clinical trials. Cancer Detect Prev. 1994;18(1):43-50. Review.

Hwu et al., The use of gene-modified tumor-infiltrating lymphocytes for cancer therapy. Ann N Y Acad Sci. May 31, 1994;716:188-97; discussion 197-203.Review.

Johnston-Early et al., Delayed hypersensitivity skin testing as a prognostic indicator in patients with small cell lung cancer. Cancer. Oct. 15, 1983;52(8):1395-400.

Jordan et al., Optimal analysis of composite cytokine responses during alloreactivity. J Immunol Methods. Feb. 1, 2002;260(1-2):1-14.

June et al., Evidence for the involvement of three distinct signals in the induction of IL-2 gene expression in human T lymphocytes. J Immunol. Jul. 1, 1989;143(1):153-61.

Kaech et al., Effector and memory T-cell differentiation: implications for vaccine development. Nat Rev Immunol. Apr. 2002;2(4):251-62.

Kalinski et al., Prostaglandin E(2) is a selective inducer of interleukin-12 p40 (IL-12p40) production and an inhibitor of bioactive IL-12p70 heterodimer. Blood. Jun. 1, 2001;97(11):3466-9.

Kameda et al., Mixed lymphokines in low dose prolong life in cyclophosphamide-treated melanoma-bearing mice. Int J Immunother. 1992;8:1-5.

Kaminuma et al., Interleukin-5 production by peripheral blood mononuclear cells of asthmatic patients is suppressed by T-440: relation to phosphodiesterase inhibition. J Pharmacol Exp Ther. Oct. 1996;279(1):240-6.

Katsuyuki et al., Clinical trials of immunotherapy for advanced prostate cancer. Urologic Oncology. 2000;5:265-73.

Kavanaugh et al., Immunologic dysfunction in cancer. Hematol Oncol Clin North Am. Aug. 1996;10(4):927-51.

Kidd, Th1/Th2 balance: the hypothesis, its limitations, and implications for health and disease. Altern Med Rev. Aug. 2003;8(3):223-46.

Kleindienst et al., Endogenous dendritic cells are required for amplification of T cell responses induced by dendritic cell vaccines in vivo. J Immunol. Mar. 15, 2003;170(6):2817-23.

Koopman et al., Reversal of human papillomavirus immune escape using IRX-2 and a toll-like receptor 3 agonist. Online. Available at http://scripties.umcg.eldoc.ub.rug.nl/root/geneeskunde/2010/KoopmanMaaike/. Jan. 1, 2011. Retrieved from the Internet on Jan. 22, 2011.

Kovacs et al., Increases in CD4 T lymphocytes with intermittent courses of interleukin-2 in patients with human immunodeficiency virus infection. A preliminary study. N Engl J Med. Mar. 2, 1995;332(9):567-75.

Lafferty et al., Immunological induction of T lymphocytes: role of antigen and the lymphocyte costimulator. Blood Cells 1978;4(3):395-406.

Lahiri et al., Engagement of TLR signaling as adjuvant: towards smarter vaccine and beyond. Vaccine. Dec. 9, 2008;26(52):6777-83.

Langenkamp et al., Kinetics of dendritic cell activation: impact on priming of TH1, TH2 and nonpolarized T cells. Nat Immunol. Oct. 2000;1(4):311-6.

Lanzavecchia et al., Understanding the generation and function of memory T cell subsets. Curr Opin Immunol. Jun. 2005;17(3):326-32.

Lopez et al., Biochemotherapy with thymosin alpha 1, interleukin-2 and dacarbazine in patients with metastatic melanoma: clinical and immunological effects. Ann Oncol. Oct. 1994;5(8):741-6.

López-Rodríguez et al., Interleukin-2 killer cells: in vitro evaluation of combination with prothymosin alpha. Lymphokine Cytokine Res. Jun. 1994;13(3):175-82.

Lou et al., Dendritic cells strongly boost the antitumor activity of adoptively transferred T cells in vivo. Cancer Res. Sep. 15, 2004;64(18):6783-90.

Maass et al., Priming of tumor-specific T cells in the draining lymph nodes after immunization with interleukin 2-secreting tumor cells: three consecutive stages may be required for successful tumor vaccination. Proc Natl Acad Sci U S A. Jun. 6, 1995;92(12):5540-4.

Mackall et al., Age, thymopoiesis, and CD4+ T-lymphocyte regeneration after intensive chemotherapy. N Engl J Med. Jan. 19, 1995;332(3):143-9.

Mackall, T-cell immunodeficiency following cytotoxic antineoplastic therapy: a review. Stem Cells. 2000;18(1):10-8.

MacLean et al., Enhancing the effect of Theratope STn-KLH cancer vaccine in patients with metastatic breast cancer by pretreatment with low-dose intravenous cyclophosphamide. J Immunother Emphasis Tumor Immunol. Jul. 1996;19(4):309-16.

Mantovani et al., Macrophage polarization: tumor-associated macrophages as a paradigm for polarized M2 mononuclear phagocytes. Trends Immunol. Nov. 2002;23 (11):549-55. Review.

Maric et al., Immunostimulatory activity of prothymosin-alpha in senescence. Ann N Y Acad Sci. 1991;621:148-58.

Maric et al., In vivo effect of prothymosin-alpha 1 on humoral and cell-mediated immune responses in the young rat. Int J Neurosci.Jul. 1991;59(1-3):135-42.

Masek et al., Neuroendocrine immune interactions in health and disease. Int Immunopharmacol. Aug. 2003;3(8):1235-46.

Mastino et al., Combination therapy with thymosin alpha 1 potentiates the anti-tumor activity of interleukin-2 with cyclophosphamide in the treatment of the Lewis lung carcinoma in mice. Int J Cancer. Feb. 1, 1992;50(3):493-9.

Mastino et al., Thymosin alpha 1 potentiates interleukin 2-induced cytotoxic activity in mice. Cell Immunol. Mar. 1991;133(1):196-205.

Mastrangelo et al., Active specific immunization in the treatment of patients with melanoma. Semin Oncol. Dec. 1996;23(6):773-81.

Mattijssen et al., Clinical and immunopathological results of a phase II study of perilymphatically injected recombinant interleukin-2 in locally far advanced, nonpretreated head and neck squamous cell carcinoma. J Immunother (1991). Feb. 1991;10(1):63-8.

Mempel et al., Rulers over randomness: stroma cells guide lymphocyte migration in lymph nodes. Immunity. Dec. 2006;25(6):867-9.

Meneses et al., Histologic findings in patients with head and neck squamous cell carcinoma receiving perilymphatic natural cytokine mixture (IRX-2) prior to surgery. Arch Pathol Lab Med. May 1998;122(5):447-54.

Meneses et al., Lymph node histology in head and neck cancer: impact of immunotherapy with IRX-2. Int Immunopharmacol. Aug. 2003;3(8):1083-91.

Middel et al., Sinus histiocytosis with massive lymphadenopathy: evidence for its relationship to macrophages and for a cytokine-related disorder. Histopathology. Dec. 1999;35(6):525-33.

Mikysková et al., Local cytokine treatment of HPV16-associated tumors results in inhibition of their lung metastases. Clin Exp Metastasis. 2001;18(7):581-7.

Mitchell et al., Promotion of human T lymphocyte proliferation by IL-4. J Immunol. Mar. 1, 1989;142(5):1548-57.

Mokyr et al., Role of antitumor immunity in cyclophosphamide-induced rejection of subcutaneous nonpalpable MOPC-315 tumors. Cancer Res. Mar. 1982;42(3):974-9.

Moody et al., Thymosin alpha 1 down-regulates the growth of human non-small cell lung cancer cells in vitro and in vivo. Cancer Res. Nov. 1, 1993;53(21):5214-8.

Morgan et al., Selective in vitro growth of T lymphocytes from normal human bone marrows. Science. Sep. 10, 1976;193(4257):1007-8.

Mule, Mechanistic aspects of successful immunotherapy of established pulmonary metastases by the systemic administration of high-dose recombinant interleukin-2. Prog Clin Biol Res. 1987;244:79-91.

(56) References Cited

OTHER PUBLICATIONS

Murphy et al., Infusion of dendritic cells pulsed with HLA-A2-specific prostate-specific membrane antigen peptides: a phase II prostate cancer vaccine trial involving patients with hormone-refractory metastatic disease. Prostate. Jan. 1, 1999;38(1):73-8.
Musiani et al., Effect of low doses of interleukin-2 injected perilymphatically and peritumorally in patients with advanced primary head and neck squamous cell carcinoma. J Biol Response Mod. Dec. 1989;8(6):571-8.
Naylor et al., Preclinical and clinical studies on immunogenicity and safety of the HIV-1 p17-based synthetic peptide Aids vaccine—HGP-30-KLH. Int J Immunopharmacol. 1991;13 Suppl 1:117-27.
Naylor et al., Enhancement of Peptide Specific DTH with Combination Cytokines. Presented CSHL Meeting Dec. 4-7, 2003. Molecular Approaches to Vaccine Design. p. 28.
Naylor et al., Immunopharmacology of thymosin alpha1 and cytokine synergy. Ann N Y Acad Sci. Sep. 2007;1112:235-44. Epub Jun. 13, 2007.
Naylor et al., IRX-2 increases the T cell-specific immune response to protein/peptide vaccines. Vaccine. Oct. 8, 2010;28(43):7054-62. Epub Aug. 13, 2010.
Naylor et al., Preclinical studies with an IRX-2 enhanced prostate vaccine. J Urology. 2008;179(4):45.
Naylor et al., Preclinical studies with IRX-2 and thymosin alpha1 in combination therapy. Ann N Y Acad Sci. Apr. 2010;1194:162-8.
Naylor et al., T cell targeted immune enhancement yields effective T cell adjuvants. Int Immunopharmacol. Aug. 2003;3(8):1205-15.
Nohria et al., Cytokines as potential vaccine adjuvants. Biotherapy. 1994;7(3-4):261-9.
O'Hagan et al., Recent developments in adjuvants for vaccines against infectious diseases. Biomol Eng. Oct. 15, 2001;18(3):69-85.
Overwijk et al., Creating therapeutic cancer vaccines: notes from the battlefield. Trends Immunol. Jan. 2001;22(1):5-7.
Paetkau et al., Proliferation of murine thymic lymphocytes in vitro is mediated by the concanavalin A-induced release of a lymphokine (costimulator). J Immunol. Oct. 1976;117(4):1320-4.
Panje, Regression of head and neck carcinoma with a prostaglandin-synthesis inhibitor. Arch Otolaryngol. Nov. 1981;107(11):658-63.
Pulley et al., Intravenous, intralesional and endolymphatic administration of lymphokines in human cancer. Lymphokine Res. 1986;5 Suppl 1:S157-63.
Randolph, Dendritic cell migration to lymph nodes: cytokines, chemokines, and lipid mediators. Semin Immunol. Oct. 2001;13(5):267-74.
Rapidis et al., Immunotherapy of head and neck cancer: current and future considerations. J Oncol. 2009;2009:346345. doi: 10.1155/2009/346345. Epub Aug. 9, 2009. 11 pages.
Rasi et al., Anti-tumor effect of combined treatment with thymosin alpha 1 and interleukin-2 after 5-fluorouracil in liver metastases from colorectal cancer in rats. Int J Cancer. Jun. 1, 1994;57(5):701-5.
Rasi et al., Combined treatment with thymosin-alpha1 and low dose interferon-alpha after dacarbazine in advanced melanoma. Melanoma Res. Apr. 2000;10(2):189-92.
Ridgway, The first 1000 dendritic cell vaccinees. Cancer Invest. 2003;21(6):873-86.
Riesbeck et al., Limited effects of temafloxacin compared with ciprofloxacin on T-lymphocyte function. Antimicrob Agents Chemother. Apr. 1994;38(4):879-82.
Riesenbeck et al., Superinduction of cytokine gene transcription by ciprofloxacin. J Immunol. Jul. 1, 1994;153(1):343-52.
Rogers et al., CD28, Ox-40, LFA-1, and CD4 modulation of Th1/Th2 differentiation is directly dependent on the dose of antigen. J Immunol. Mar. 15, 2000;164(6):2955-63.
Romani et al., Generation of mature dendritic cells from human blood. An improved method with special regard to clinical applicability. J Immunol Methods. Sep. 27, 1996;196(2):137-51.
Rosenberg et al., A progress report on the treatment of 157 patients with advanced cancer using lymphokine-activated killer cells and interleukin-2 or high-dose interleukin-2 alone. N Engl J Med. Apr. 9, 1987;316(15):889-97.
Rosenberg et al., Cancer immunotherapy: moving beyond current vaccines. Nat Med. Sep. 2004;10(9):909-15.
Rosenberg et al., Observations on the systemic administration of autologous lymphokine-activated killer cells and recombinant interleukin-2 to patients with metastatic cancer. N Engl J Med. Dec. 5, 1985;313(23):1485-92.
Rosenberg, Immunotherapy of cancer by systemic administration of lymphoid cells plus interleukin-2. J Biol Response Mod. Oct. 1984;3(5):501-11.
Rosenberg, The development of new immunotherapies for the treatment of cancer using interleukin-2. A review. Ann Surg. Aug. 1988;208(2):121-35. Review.
Saha et al., Zinc induces thymulin secretion from human thymic epithelial cells in vitro and augments splenocyte and thymocyte responses in vivo. Int J Immunopharmacol. Sep. 1995;17(9):729-33.
Saito et al., Spontaneous ex vivo apoptosis of peripheral blood mononuclear cells in patients with head and neck cancer. Clin Cancer Res. Jun. 1999;5(6):1263-73.
Sallusto et al., Dendritic cells use macropinocytosis and the mannose receptor to concentrate macromolecules in the major histocompatibility complex class II compartment: downregulation by cytokines and bacterial products. J Exp Med. Aug. 1, 1995;182(2):389-400.
Sallusto et al., Efficient presentation of soluble antigen by cultured human dendritic cells is maintained by granulocyte/macrophage colony-stimulating factor plus interleukin 4 and downregulated by tumor necrosis factor alpha. J Exp Med. Apr. 1, 1994;179(4):1109-18.
Schuler-Thurner et al., Rapid induction of tumor-specific type 1 T helper cells in metastatic melanoma patients by vaccination with mature, cryopreserved, peptide-loaded monocyte-derived dendritic cells. J Exp Med. May 20, 2002;195(10):1279-88.
Schuloff, Thymic peptide hormones: basic properties and clinical applications in cancer. Crit Rev Oncol Hematol. 1985;3(4):309-76. Review.
Scott et al., Cell-mediated immune response to human papillomavirus infection. Clin Diagn Lab Immunol. Mar. 2001;8(2):209-20.
Scott et al., Th1 Cytokine Patterns in Cervical Human Papillomavirus Infection. Clin Diagn Lab Immunol. Sep. 1999; 6(5): 751-5.
Silecchia et al., Efficacy of repeated cycles of chemo-immunotherapy with thymosin alpha1 and interleukin-2 after intraperitoneal 5-fluorouracil delivery. Cancer Immunol Immunother. Jul. 1999;48(4):172-8.
Sozzani et al., Differential regulation of chemokine receptors during dendritic cell maturation: a model for their trafficking properties. J Immunol. Aug. 1, 1998;161(3):1083-6.
Steinman et al., Avoiding horror autotoxicus: the importance of dendritic cells in peripheral T cell tolerance. Proc Natl Acad Sci U S A. Jan. 8, 2002;99(1):351-8. Epub Jan. 2, 2002.
Steinman, The dendritic cell system and its role in immunogenicity. Annu Rev Immunol. 1991;9:271-96.
Syrjänen, Human papillomavirus (HPV) in head and neck cancer. J Clin Virol. Mar. 2005;32 Suppl 1:S59-66.
Tagawa, Cytokine therapy for cancer. Curr Pharm Des. Apr. 2000;6(6):681-99.
Talmage et al., Activation of cytotoxic T cells by nonstimulating tumor cells and spleen cell factor(s). Proc Natl Acad Sci U S A. Oct. 1977;74(10):4610-4.
Tas et al., Depressed monocyte polarization and clustering of dendritic cells in patients with head and neck cancer: in vitro restoration of this immunosuppression by thymic hormones. Cancer Immunol Immunother. 1993;36(2):108-14.
Thurman et al., Comparative evaluation of multiple lymphoid and recombinant human interleukin-2 preparations. J Biol Response Mod. Feb. 1986;5(1):85-107.

(56) References Cited

OTHER PUBLICATIONS

Tjoa et al., Development of dendritic-cell based prostate cancer vaccine. Immunol Lett. Sep. 15, 2000;74(1):87-93.
Tjoa et al., Evaluation of phase I/II clinical trials in prostate cancer with dendritic cells and PSMA peptides. Prostate. Jun. 15, 1998;36(1):39-44.
Tzehoval et al., Thymosins alpha 1 and beta 4 potentiate the antigen-presenting capacity of macrophages. Immunopharmacology. Sep.-Oct. 1989;18(2):107-13.
Valente et al., Infiltrating leukocyte populations and T-lymphocyte subsets in head and neck squamous cell carcinomas from patients receiving perilymphatic injections of recombinant interleukin 2. A pathologic and immunophenotypic study. Mod Pathol. Nov. 1990;3(6):702-8.
Van Den Eynde et al., T cell defined tumor antigens. Curr Opin Immunol. Oct. 1997;9(5):684-93.
Van Lier et al , Immobilized anti-CD3 monoclonal antibodies induce accessory cell-independent lymphokine production, proliferation and helper activity in human T lymphocytes. Immunology. Sep. 1989;68(1):45-50.
Verastegui et al. Immunological approach in the evaluation of regional lymph nodes of patients with squamous cell carcinoma of the head and neck. Clin Immunol. Jan. 2002;102(1):37-47.
Verastegui et al., Long-term immune dysfunction after radiotherapy to the head and neck area. Int Immunopharmacol. Aug. 2003;3(8):1093-1104.
Verwilghen et al., Differences in the stimulating capacity of immobilized anti-CD3 monoclonal antibodies: variable dependence on interleukin-1 as a helper signal for T-cell activation. Immunology. Feb. 1991;72(2):269-76.
Vine et al., T4 cell activation by immobilized phytohemagglutinin: differential capacity to induce IL-2 responsiveness and IL-2 production. J Immunol. Oct. 15, 1988;141(8):2593-600.
Wang et al., Human tumor antigens for cancer vaccine development. Immunol Rev. Aug. 1999;170:85-100.
Webb et al., Mitogen-induced human lymphocyte activation in serum-free medium. Clin Immunol Immunopathol. Apr. 1973;1(3):304-10.
Whiteside et al., Antigen-processing machinery in human dendritic cells: up-regulation by maturation and down-regulation by tumor cells. J Immunol. Aug. 1, 2004;173(3):1526-34.
Whiteside et al., Evidence for local and systemic activation of immune cells by peritumoral injections of interleukin 2 in patients with advanced squamous cell carcinoma of the head and neck. Cancer Res. Dec. 1, 1993;53(23):5654-62.
Whiteside, Immunobiology and immunotherapy of head and neck cancer. Curr Oncol Rep. Jan. 2001;3(1):46-55.
Chen et al., Serum and mucosal immune responses to an inactivated influenza virus vaccine induced by epidermal powder immunization. J Virol. Sep. 2001;75(17):7956-65.
Marschner et al., CpG ODN enhance antigen-specific NKT cell activation via plasmacytoid dendritic cells. Eur J Immunol. Aug. 2005;35(8):2347-57.
Heath et al., Cytokines as immunological adjuvants. Vaccine. 1992;10(7):427-34. Review.
Sano et al., CpG Oligodeoxynucleotides as a Future Vaccine for Allergic Diseases. Allergol Intl. 2005;54:17-23.
Simmons et al., GM-CSF as a systemic adjuvant in a phase II prostate cancer vaccine trial. Prostate. Jun. 1, 1999;39(4):291-7.
PCT/US2010/035060, Aug. 20, 2010, International Search Report and Written Opinion.
PCT/US2010/035060, Nov. 15, 2011, International Preliminary Report on Patentability.
International Search Report and Written Opinion dated Aug. 20, 2010 for Application No. PCT/US2010/035060.
International Preliminary Report on Patentability dated Nov. 15, 2011 for Application No. PCT/US2010/035060.
Cavaillon, Pro-versus Anti-Inflammatory Cytokines: Myth or Reality. Cell Mol Biol. 2001;47(4):695-702.
Kruit et al., Immunization with recombinant MAGE-A3 protein combined with adjuvant systems AS15 or AS02B in patients with unresectable and progressive metastatic cutaneous melanoma: A randomized open-label phase II study of the EORTC Melanoma Group (16032- 18031).2008 ASCO Meeting Proceedings Post-Meeting Edition. J Clin Oncol. 2008;26(15S):9065.
Kruit et al., Selection of Immunostimulant AS15 for Active Immunization With MAGE-A3 Protein: Results of a Randomized Phase II Study of the European Organisation for Research and Treatment of Cancer Melanoma Group in Metastatic Melanoma. J Clin Oncol. Jul. 1, 2013;31(19):2413-20.
McLaughlin et al., Improved immunotherapy of a recombinant carcinoembryonic antigen vaccinia vaccine when given in combination with interleukin-2. Cancer Res. May 15, 1996;56(10):2361-7.
Qin et al., Isolation and identification of a new thymic peptide from calf thymus. Biochem (Mosc). Aug. 2004;69(8):921-5.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Yang et al., The use of polyethylene glycol-modified interleukin-2 (PEG-IL-2) in the treatment of patients with metastatic renal cell carcinoma and melanoma. A phase I study and a randomized prospective study comparing IL-2 alone versus IL-2 combined with PEG-IL-2. Cancer. Aug. 15, 1995;76(4):687-94.
Dubey et al., Costimulatory requirements of naive CD4+ T cells. ICAM-1 or B7-1 can costimulate naive CD4 T cell activation but both are required for optimum response. J Immunol. Jul. 1, 1995;155(1):45-57.
Hodge et al., A triad of costimulatory molecules synergize to amplify T-cell activation. Cancer Res. Nov. 15, 1999;59(22):5800-7.
Kawai et al., Innate immune recognition of viral infection. Nature Immunology. Feb. 2006;7(2):131-7.
Krishnan et al., Toll-like receptor signal transduction. Exp Mol Med. Aug. 31, 2007;39(4):421-38.
Mellstedt et al., The challenge of biosimilars. Ann Oncol. Mar. 2008;19(3):411-9. Epub Sep. 14, 2007.
Müller et al., The advent of biosimilars: challenges and risks. Swiss Med Wkly. Jul. 1, 2014;144:w13980. doi: 10.4414/smw.2014. 13980. eCollection 2014.
Tarle, Serial measurements of tissue polypeptide specific antigen (TPS), PSA, PAP and CEA serotest values in treated patients with primary and metastatic prostate cancer. Anticancer Res. May-Jun. 1993;13(3):769-77. PubMed PMID: 7686362. Abstract Only.

\* cited by examiner

FIGURE 33B

B. Ovalbumin Antibody Response

A. NFT Specific T cell Response

SEQUENCE LISTING

```
<160> NUMBER OF SEQ ID NOS: 20

<210> SEQ ID NO 1
<211> LENGTH: 9
<212> TYPE: PRT
<213> ORGANISM: Artificial Sequence
<220> FEATURE:
<223> OTHER INFORMATION: Prostate Specific Membrane Antigen Peptide

<400> SEQUENCE: 1

Leu Leu His Glu Thr Asp Ser Ala Val
1               5

<210> SEQ ID NO 2
<211> LENGTH: 8
<212> TYPE: PRT
<213> ORGANISM: Artificial Sequence
<220> FEATURE:
<223> OTHER INFORMATION: Prostate Specific Membrane Antigen Peptide

<400> SEQUENCE: 2

Leu Phe Asp Ile Glu Ser Lys Val
1               5

<210> SEQ ID NO 3
<211> LENGTH: 20
<212> TYPE: DNA
<213> ORGANISM: Artificial Sequence
<220> FEATURE:
<223> OTHER INFORMATION: CpG oligonucleotide

<400> SEQUENCE: 3
tccatgacgt tcctgacgtt                                                  20

<210> SEQ ID NO 4
```

```
<211> LENGTH: 32
<212> TYPE: PRT
<213> ORGANISM: Artificial Sequence
<220> FEATURE:
<223> OTHER INFORMATION: synthetic long peptide for HPV

<400> SEQUENCE: 4

Met His Gln Lys Arg Thr Ala Met Phe Gln Asp Pro Gln Glu Arg Pro
1               5                   10                  15

Arg Lys Leu Pro Gln Leu Cys Thr Glu Leu Gln Thr Thr Ile His Asp
            20                  25                  30

<210> SEQ ID NO 5
<211> LENGTH: 32
<212> TYPE: PRT
<213> ORGANISM: Artificial Sequence
<220> FEATURE:
<223> OTHER INFORMATION: synthetic long peptide for HPV

<400> SEQUENCE: 5

Leu Pro Gln Leu Cys Thr Glu Leu Gln Thr Thr Ile His Asp Ile Ile
1               5                   10                  15

Leu Glu Cys Val Tyr Cys Lys Gln Gln Leu Leu Arg Arg Glu Val Tyr
            20                  25                  30

<210> SEQ ID NO 6
<211> LENGTH: 25
<212> TYPE: PRT
<213> ORGANISM: Artificial Sequence
<220> FEATURE:
<223> OTHER INFORMATION: synthetic long peptide for HPV

<400> SEQUENCE: 6

Lys Gln Gln Leu Leu Arg Arg Glu Val Tyr Asp Phe Ala Phe Arg Asp
1               5                   10                  15

Leu Cys Ile Val Tyr Arg Asp Gly Asn
            20                  25

<210> SEQ ID NO 7
<211> LENGTH: 26
<212> TYPE: PRT
<213> ORGANISM: Artificial Sequence
<220> FEATURE:
<223> OTHER INFORMATION: synthetic long peptide for HPV

<400> SEQUENCE: 7

Arg Asp Leu Cys Ile Val Tyr Arg Asp Gly Asn Pro Tyr Ala Val Cys
1               5                   10                  15

Asp Lys Cys Leu Lys Phe Tyr Ser Lys Ile
            20                  25

<210> SEQ ID NO 8
<211> LENGTH: 25
<212> TYPE: PRT
<213> ORGANISM: Artificial Sequence
<220> FEATURE:
<223> OTHER INFORMATION: synthetic long peptide for HPV

<400> SEQUENCE: 8

Asp Lys Cys Leu Lys Phe Tyr Ser Lys Ile Ser Glu Tyr Arg His Tyr
1               5                   10                  15

Cys Tyr Ser Leu Tyr Gly Thr Thr Leu
            20                  25
```

```
<210> SEQ ID NO 9
<211> LENGTH: 24
<212> TYPE: PRT
<213> ORGANISM: Artificial Sequence
<220> FEATURE:
<223> OTHER INFORMATION: synthetic long peptide for HPV

<400> SEQUENCE: 9

His Tyr Cys Tyr Ser Leu Tyr Gly Thr Thr Leu Glu Gln Gln Tyr Asn
1               5                   10                  15

Lys Pro Leu Cys Asp Leu Leu Ile
            20

<210> SEQ ID NO 10
<211> LENGTH: 32
<212> TYPE: PRT
<213> ORGANISM: Artificial Sequence
<220> FEATURE:
<223> OTHER INFORMATION: synthetic long peptide for HPV

<400> SEQUENCE: 10

Tyr Gly Thr Thr Leu Glu Gln Gln Tyr Asn Lys Pro Leu Cys Asp Leu
1               5                   10                  15

Leu Ile Arg Cys Ile Asn Cys Gln Lys Pro Leu Cys Pro Glu Glu Lys
            20                  25                  30

<210> SEQ ID NO 11
<211> LENGTH: 32
<212> TYPE: PRT
<213> ORGANISM: Artificial Sequence
<220> FEATURE:
<223> OTHER INFORMATION: synthetic long peptide for HPV

<400> SEQUENCE: 11

Arg Cys Ile Asn Cys Gln Lys Pro Leu Cys Pro Glu Glu Lys Gln Arg
1               5                   10                  15

His Leu Asp Lys Lys Gln Arg Phe His Asn Ile Arg Gly Arg Trp Thr
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: synthetic long peptide for HPV

<400> SEQUENCE: 12

Asp Lys Lys Gln Arg Phe His Asn Ile Arg Gly Arg Trp Thr Gly Arg
1               5                   10                  15

Cys Met Ser Cys Cys Arg Ser Ser Arg Thr Arg Arg Glu Thr Gln Leu
            20                  25                  30

<210> SEQ ID NO 13
<211> LENGTH: 35
<212> TYPE: PRT
<213> ORGANISM: Artificial Sequence
<220> FEATURE:
<223> OTHER INFORMATION: synthetic long peptide for HPV

<400> SEQUENCE: 13

Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu Asn Asp Ser Ser
            20                  25                  30
```

-continued

```
Glu Glu Glu
        35

<210> SEQ ID NO 14
<211> LENGTH: 35
<212> TYPE: PRT
<213> ORGANISM: Artificial Sequence
<220> FEATURE:
<223> OTHER INFORMATION: synthetic long peptide for HPV

<400> SEQUENCE: 14

Leu Tyr Cys Tyr Glu Gln Leu Asn Asp Ser Ser Glu Glu Asp Glu
1               5                   10                  15

Ile Asp Gly Pro Ala Gly Gln Ala Glu Pro Asp Arg Ala His Tyr Asn
            20                  25                  30

Ile Val Thr
        35

<210> SEQ ID NO 15
<211> LENGTH: 35
<212> TYPE: PRT
<213> ORGANISM: Artificial Sequence
<220> FEATURE:
<223> OTHER INFORMATION: synthetic long peptide for HPV

<400> SEQUENCE: 15

Gly Gln Ala Glu Pro Asp Arg Ala His Tyr Asn Ile Val Thr Phe Cys
1               5                   10                  15

Cys Lys Cys Asp Ser Thr Leu Arg Leu Cys Val Gln Ser Thr His Val
            20                  25                  30

Asp Ile Arg
        35

<210> SEQ ID NO 16
<211> LENGTH: 35
<212> TYPE: PRT
<213> ORGANISM: Artificial Sequence
<220> FEATURE:
<223> OTHER INFORMATION: synthetic long peptide for HPV

<400> SEQUENCE: 16

Thr Leu Arg Leu Cys Val Gln Ser Thr His Val Asp Ile Arg Thr Leu
1               5                   10                  15

Glu Asp Leu Leu Met Gly Thr Leu Gly Ile Val Cys Pro Ile Cys Ser
            20                  25                  30

Gln Lys Pro
        35

<210> SEQ ID NO 17
<211> LENGTH: 15
<212> TYPE: PRT
<213> ORGANISM: Artificial sequence
<220> FEATURE:
<223> OTHER INFORMATION: Synthetic polypeptide

<400> SEQUENCE: 17

Asn Phe Thr Gln Ile Pro His Leu Ala Gly Thr Glu Gln Asn Phe
1               5                   10                  15

<210> SEQ ID NO 18
<211> LENGTH: 15
<212> TYPE: PRT
<213> ORGANISM: Artificial Sequence
<220> FEATURE:
```

```
<223> OTHER INFORMATION: Synthetic polypeptide

<400> SEQUENCE: 18

Asn Phe Thr Arg Thr Pro His Leu Ala Gly Thr Gln Asn Asn Phe
1               5                   10                  15

<210> SEQ ID NO 19
<211> LENGTH: 10
<212> TYPE: PRT
<213> ORGANISM: Artificial Sequence
<220> FEATURE:
<223> OTHER INFORMATION: Synthetic polypeptide

<400> SEQUENCE: 19

Asn Gly Ser Leu Gln Cys Arg Ile Cys Ile
1               5                   10

<210> SEQ ID NO 20
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 20

Ser Ile Ile Asn Phe Glu Lys Leu
1               5
```

VACCINE IMMUNOTHERAPY

RELATED APPLICATIONS

This application is a national stage filing under U.S.C. §371 of PCT International application PCT/US2010/035060, filed May 17, 2010. Application PCT/US2010/035060 claims priority under 35 U.S.C. §119(e) to U.S. Provisional Application Ser. No. 61/178,741, entitled "VACCINE IMMUNOTHERAPY" filed on May 15, 2009.

BACKGROUND OF THE INVENTION

1. Technical Field

The present invention relates to vaccine immunotherapy. More specifically, the present invention relates to compositions and methods for eliciting and potentiating an immune response to endogenous or exogenous antigens in patients having cancer or other antigen-producing disease states or lesions and for eliciting and potentiating an immune response to adjuvants.

2. Background Art

It has become increasingly apparent that human cancers possess antigens, which, if acted upon by the host's immune system, can result in tumor regression. These antigens have been defined by both serological and cellular immune approaches, which have lead to the definition of both B and T cell epitopes (Sahin, 1997; Van der Eynde, 1997; Wang, 1999). Based upon these results, it has become a goal of cancer immunotherapists to induce the regression of tumors. However, historically, successful efforts have been sporadic and generally minor in frequency and magnitude.

A fundamental problem in the effort to immunize cancer patients, i.e., against tumor antigens, is that the tumor-bearing state is associated with immunosuppressive mechanisms derived from both the tumor and the host's disturbed immune system (Kavanaugh, 1996), thereby making immunization difficult and until now impossible on a consistent basis. Immune suppression or depletion involves a reduced capacity of the immune system to respond. Such suppression can be drug-induced, i.e., by drug treatment, virus-induced, e.g., as in AIDS, or induced by a disease state such as cancer. The immune system in this condition is effectively turned off. In the case of a disease state such as cancer, the body is not able to protect itself against tumor antigens, thus allowing a tumor to grow and possibly metastasize.

A variety of tumor immunization strategies have been developed. All of these strategies are complex and deviate significantly from the conventional immunization strategies used for infectious diseases (see, e.g., Weber, 2000). One such tumor immunization strategy involves THERATOPE® (Biomira), a sialyl Tn polysaccharide mucin antigen conjugated with keyhole limpet hemocyanin (KLH) and administered with DETOX® mycobacterium adjuvant and low dose cyclophosphamide (Maclean, 1996). Use of this vaccine in patients with metastatic breast and ovarian cancer has yielded major clinical responses (i.e., greater than 50% tumor reduction) in only a low percentage of patients.

Gene therapy has also been attempted using viral constructs as expression vectors for genes expressing tumor antigens. For example, a recombinant vaccinia virus construct encoding modified forms of human papilloma virus (HPV) E6 and E7 protein sequences has been used for immunization of patients with cervical cancer. Vaccination with this construct yielded questionable clinical responses (Borysiewickz, 1996). See also, Sanda, 1999 wherein a recombinant vaccinia-PSA (prostate-specific antigen) construct was used as a vaccine in prostate cancer patients.

Another approach has been dendritic cell-mediated therapy, e.g., wherein dendritic cells were pulsed with oligopeptide fragments of prostate-specific membrane antigens (PSMA). The dendritic cells (with or without the priming PSMA antigens) were then administered to patients with metastatic prostate cancer. Major clinical responses were obtained in only a low percentage of patients (Murphy, 1999; see also, Tjoa, 2000).

Additionally, autologous tumors have been used with low dose cyclophosphamide and BCG (Bacillus Calmette-Guerin) to immunize cancer patients with malignant melanoma. However, few clinical responses were reported (Mastrangelo, 1996). Another strategy included using MAGE antigens with a variety of vaccine adjuvants. Again, this has yielded few, if any, responses in patients with malignant melanoma (personal communication, Thierry Boon).

Several patents to Doyle et al (U.S. Pat. Nos. 5,503,841; 5,800,810; 6,060,068; 5,643,565; and 5,100,664) disclose methods of enhancing the immune response in patients using interleukin 2 (IL-2). This method is disclosed for use in response to infectious diseases and primarily functions using antigens known to be immunogenic. Limited applicability was demonstrated. As disclosed above, the treatment of cancer is known to require different approaches. To date, treatment with IL-2 has shown minor effects in two cancers, renal cell and malignant melanoma (response rates less than 20%). It is generally considered ineffective in squamous cell head and neck and cervical cancer and in prostate cancer. Hence, it is not approved for these uses.

It is important to contrast prophylactic vaccines using known "classic" antigens of complex structure and high molecular weights in healthy patients vs. therapeutic vaccines (generally unsuccessful) with tumor antigens or peptides (general unsuccessful) in immunosuppressed patients (generally unsuccessful). The first is easy and our current viral vaccines attest to their efficacy. The latter is nearly impossible on a routine basis despite thirty years of intense effort.

Effective cancer vaccines require stimulation of cell-mediated immunity, perhaps even in preference to antibody production. As noted, despite numerous studies with various antigens, adjuvants and vaccine constructs, the clinical trial data to date have been disappointing. The critical events for a T cell mediated anti-cancer immune response are antigen presentation to T cells, primarily in the lymph nodes draining the site of the tumor or immunization, followed by T cell activation and migration to the peripheral sites. In fact, the uptake of the antigen by tissue macrophages, neutrophils and/or dendritic cells and presentation of processed peptides in combination with MHC class I and class II antigens to the T cells in the lymph node are crucial to a complete immune response. Key to a successful T cell immune activation is the generation of the appropriate cytokine environment to drive the immune response to a vaccine, at both the site of immunization and draining lymph nodes. The fact that the mechanism of action of the immune system has heretofore not been completely understood prevents the currently available cancer vaccines from achieving their full potential.

The kinetics of the immune response includes two phases. The first is the draining of the antigen and soluble proteins to the lymph nodes, where an initial immune activation occurs. Twenty four to forty eight hours later, antigen-presenting cells (APCs), most particularly dendritic cells, migrate from the site of immunization via the draining lymphatic ducts to the lymph node, where a second wave of presentation of antigen and activation occurs. More specifically, the APCs interact in the lymph node with precursor T helper cells via engagement of co-stimulatory receptors as well as T cell receptors to yield T helper 1 (Th1) cells and/or T helper 2 (Th2) cells. The ratio of these subsets controls subsequent development of either cell-mediated or humoral (antibody) immune responses (Th1 biasing towards DTH/cytotoxicity, whereas Th2 biases towards antibody production). Following the induction of these activated T cells, the immune response subsides, leaving predominately memory T cells, which are capable of responding upon re-exposure to antigen.

The critical events in this pathway are mediated by cytokines that bias the response in the direction of humoral or cellular immunity. Locally produced cytokines, such as IL-1, IL-2, IFN-γ, GM-CSF, IL-6, TNF-α, IL-I2 and IL-8, are associated with the recruitment of immune system cells, antigen uptake, dendritic cell maturation, dampening of T regulatory cell activity, T cell education and proliferation, and the development of Th1 cells (Naylor, 2003). The interdependence of the response means that the activity of any given cytokine depends on the occurrence of precursor events such that the simultaneous presence of multiple cytokines can have different effects at both the injection site and the draining lymph nodes, depending on the kinetics of cell responses to different cytokines.

Failure to evoke a sufficient immune response with traditional vaccines has remained a challenge for vaccine development. Adjuvants have thus been developed to accelerate, enhance, and prolong the immune response to vaccination and reduce the amount of antigen needed per dose. Adjuvants have been used for almost 100 years. Le Moignic and Pinoy first recognized that *Salmonella typhimurium* suspended in mineral oil potentiated immune responses in 1916. In 1926, Ramon demonstrated that an antitoxin response could be augmented by a large range of substances such as agar, tapioca, lethicin, starch oil, saponin, and breadcrumbs, and Glenny used aluminum salt to precipitate diphtheria toxoid improving immunogenicity, leading to alums used today. Quil A was determined to have adjuvant properties in 1936 by Thibaud and Richou. Quil A is a triterpenoid saponin extracted from the bark of the South American Molina soap tree *Quillaja saponaria*. In 1937, Freund also developed adjuvants from emulsions. Little progress has been made since then. As we begin to understand the immune system as described above, more progress is being made with adjuvants. Several adjuvants have been developed for vaccines, including cancer vaccines, but still only alum has really had success worldwide. Alum is a Th2 adjuvant; however, adjuvants providing a Th1 response are also desired. Adjuvants are especially needed for population groups that do not sufficiently respond to conventional vaccines due to impaired immune response, such as elderly or immunosuppressed patients. Adjuvants have the potential to overcome immunotolerance; however, none have been very successful in doing so to date. Therefore, there remains a need for an effective adjuvant for various diseases including cancer.

The present invention utilizes the primary cell-derived biologic IRX-2, also previously known as a natural cytokine mixture (NCM), as disclosed in U.S. Pat. Nos. 5,632,983 and 5,698,194, issued to Applicant, to immunize patients and/or potentiate immunization, such as cancer patients or other patients with other antigen-producing lesions or disease states. More specifically, IRX-2 has been previously shown in U.S. Pat. No. 5,698,194 to be effective in promoting T cell development and function in aged, immunosuppressed mice. IRX-2 was shown to decrease the proportion of immature T cells and increase the proportion of mature T cells in the thymus. The IRX-2 included IL-1, IL-2, IL-6, IL-8, IL-12, IFN-γ, TNF-α, GM-CSF, G-CSF, and IL-3, IL-4, IL-7 in trace amounts.

It will be apparent from the disclosure detailed herein that the cytokine compositions of the invention and the methods that utilize them are applicable to the stimulation of an immune response to any antigen of interest, e.g, cancer or tumor antigens, as well as antigens produced by other persistent disease states or lesions. As detailed herein, the cytokine mixture of the invention acts as an adjuvant preferably to stimulate T cell immunity in vivo.

Moreover, the present invention relates to, but not exclusively to, eliciting an immune response to either endogenous antigens, i.e., proteins or peptides that are located in vivo and are processed and presented by APCs (such as dendritic cells) in vivo, or to exogenous antigens, i.e., proteins or peptides that have been isolated or generated in vitro and then administered in vivo to an environment (e.g., a lymph node) where dendritic cells are present and can effectively present the antigens, e.g., to T cells. In particular as it relates to peptide antigens, this goal is considered by many immunologists to be insurmountable. Peptides are generally considered to be much too small to be effective immunogens, their half-life is short, and they are often non-mutated self antigens to which the patient is immunologically tolerant. Thus, gaining an immune response to such antigens is tantamount to inducing auto-immunity.

As described herein, the present invention is useful to develop a consistent and effective method of vaccine immunotherapy, wherein immune responses are elicited in patients, such as cancer patients, using the cytokine compositions of the present invention in combination with endogenous and/or exogenous disease-associated antigens, including tumor antigens and peptides, as well as with other adjuvants.

SUMMARY OF THE INVENTION

The present invention provides for a composition for treating cancer, including synergistic amounts of a primary cell-derived biologic having the cytokines IL-1, IL-2, IL-6, IL-8, TNF-α, and IFN-γ, and a vaccine having at least one antigen.

The present invention provides for a composition for enhancing an immune response in a patient, including synergistic amounts of a primary cell-derived biologic having the cytokines IL-1, IL-2, IL-6, IL-8, TNF-α, and IFN-γ, in combination with at least one adjuvant.

The present invention further provides for a method of treating cancer, including the step of administering a composition including synergistic amounts of a primary cell-derived biologic including the cytokines IL-1, IL-2, IL-6, IL-8, TNF-α, and IFN-γ, and a vaccine including at least one antigen.

The present invention provides for a method of reversing immune suppression and gaining immunity to cancer, including the steps of administering a composition including synergistic amounts of a primary cell-derived biologic including the cytokines IL-1, IL-2, IL-6, IL-8, TNF-α, and IFN-γ, and a vaccine including at least one antigen, stimulating the production of naïve T cells, maturing immature dendritic cells, and allowing presentation by resulting mature dendritic cells of the antigen to the naïve T cells, thereby reversing immune suppression and gaining immunity to the cancer.

The present invention also provides for a method of producing an immune response to an exogenous antigen in a patient, including the steps of administering an adjuvant of a primary cell-derived biologic including the cytokines IL-1, IL-2, IL-6, IL-8, TNF-α, and IFN-γ, and at least one exogenous antigen, wherein the exogenous antigen does not normally produce an immune response, and producing an immune response in the patient.

The present invention provides for a method of enhancing an immune response in a patient, including the steps of administering a primary cell-derived biologic including the cytokines IL-1, IL-2, IL-6, IL-8, TNF-α, and IFN-γ, in combination with at least one adjuvant, and enhancing the immune response of the patient by a synergistic interaction of the primary cell-derived biologic and the adjuvant.

The present invention further provides for a method of increasing function of an immune system, including the steps of administering a primary cell-derived biologic including the cytokines IL-1, IL-2, IL-6, IL-8, TNF-α, and IFN-γ, in combination with at least one adjuvant, wherein the adjuvant has a mechanism of action that is different than the mechanism of action of the primary cell-derived biologic, and increasing function of the immune response.

The present invention further provides for a method of increasing function of an immune system by administering a primary cell biologic adjuvant system.

BRIEF DESCRIPTION OF THE DRAWINGS

Other advantages of the present invention are readily appreciated as the same becomes better understood by reference to the following detailed description when considered in connection with the accompanying drawings wherein:

FIG. 29A depicts the serum antibody response to the OVA carrier in mice immunized with the OVA-PSMA conjugate and IRX-2 (IRX), alum or CpG, data are presented as mean and standard error of the mean for 5-10 mice per group, FIG. 29B depicts the serum antibody response to the PSMA peptides in mice immunized with the OVA-PSMA conjugate and IRX-2 (IRX), alum or CpG, and FIG. 29C depicts the serum antibody response to the PSMA peptides in mice immunized with the KLH-PSMA conjugate in combination with IRX-2 (IRX), alum or PBS, the results were determined by ELISA assay and are presented as optical density;

FIG. 33B is a bar graph of effect of additional injections of IRX-2 on immune response to antigen;

DETAILED DESCRIPTION OF THE INVENTION

Figure 1:
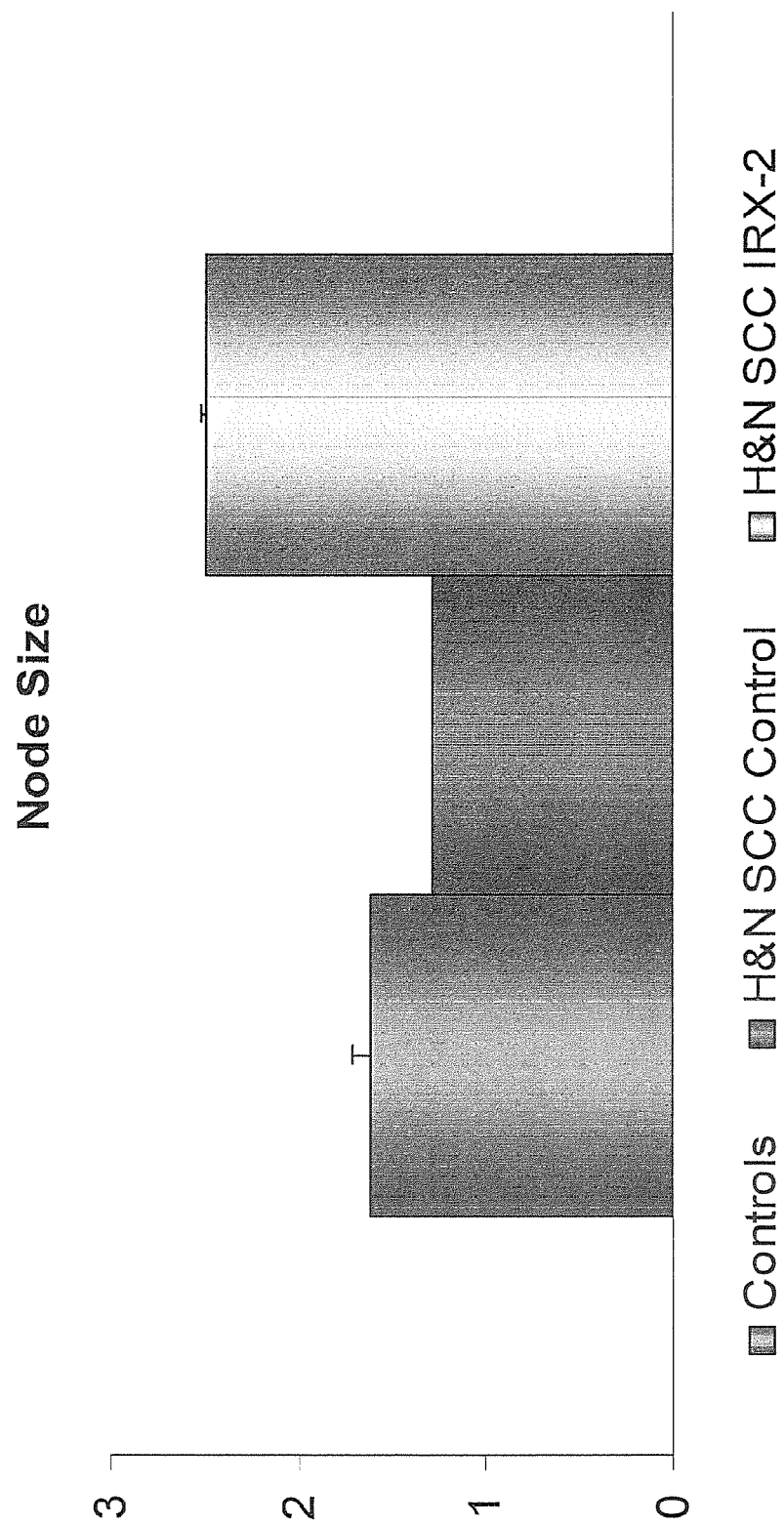
FIG. 1 is a bar graph showing lymph node size in normal controls, cancer controls or IRX-2-treated populations with H&NSCC.

The present invention relates to compositions and methods of immunotherapy and treating cancer or other antigen-producing persistent lesions or disease states. More specifically, the invention relates to compositions and methods for eliciting an immune response to antigens associated with a cancer or other antigen-producing disease or lesion, wherein a primary cell-derived biologic comprising IL-1, IL-2, IL-6, IL-8, IFN-γ, and TNF-α, as well as a cancer vaccine including at least one antigen is administered to a patient in an amount effective to stimulate an immune response to the antigen in the patient. According to the present invention, the antigen is preferably an exogenous antigen and the primary cell-derived biologic acts as an adjuvant with the antigen to stimulate an immune response to the antigen in a patient. The primary cell-derived biologic can also be used in combination with other adjuvants as described herein.

Definitions

As used herein, the term "adjuvant" denotes a composition with the ability to enhance the immune response to a particular antigen. Such ability is manifested by a significant increase in immune-mediated protection. To be effective, an adjuvant must be delivered at or near the site of antigen. Enhancement of immunity is typically manifested by either a significant increase (usually greater than 10 fold) in the titer of antibody raised to the antigen and/or enhancement of cellular immunity, which can be measured by a positive skin test, cytotoxic T cell assay, ELISPOT assay for IFN-γ or IL-2, or T cell infiltration into the tumor. The cytokine compositions of the present invention are particularly suited to enhance T cell-mediated immune responses. The adjuvant effects of the cytokine compositions of the invention include the generation of naïve T cells, the promotion of dendritic cell differentiation and maturation, the stimulation of monocytes and macrophages, and in the case of cancer patients, increased lymphocyte infiltration into tumors, tumor fragmentation, tumor regression, and reduction of sinus histiocytosis in the lymph nodes.

"Adjuvant system" as used herein denotes combining adjuvants to work together to obtain optimally effective and safe formulation in which each part of the vaccine, the antigen and adjuvant(s), works together to produce an immune response. Examples of such adjuvant systems are ASO2, 3 and 4 formulated vaccines made by Glaxo Smith Kline (GSK).

"Vaccine" as used herein, refers to a vaccine including at least one antigen, and preferably more than one antigen, that is administered to a patient to create an immune response and preferably T cell response to the antigen(s) delivered. The vaccine can include various other components such as a carrier or other stimulatory molecules. The vaccines can be DNA-based vaccines, peptide-based vaccines, or protein-based vaccines encoded in various viral/bacterial vectors or cells.

As used herein, "effective amount" refers to an amount of primary cell derived biologic that is needed to achieve the desired result of the present invention, namely, producing an immune response to an antigen by a synergistic manner. One skilled in the art can determine the effective amount of the primary cell derived biologic that should be given to a particular patient.

"IRX-2", also known as "citoplurikin", is a leukocyte-derived, natural primary cell-derived biologic produced by purified human white blood cells (mononuclear cells) stimulated by phytohemagglutinin (PHA) and ciprofloxacin (CIPRO). By definition, IRX-2 is an adjuvant system. The major active components are interleukin 1β (IL-1β, also referred to herein as IL-1), interleukin 2 (IL-2), interleukin 6 (IL-6), interleukin 8 (IL-8), tumor necrosis factor α (TNF-α), and γ-interferon (IFN-γ). Preferably, the IRX-2 used in the present invention includes these six critical cytokines. IRX-2 has also previously been referred to as an "NCM", a natural cytokine mixture, defined and set forth in U.S. Pat. Nos. 6,977,072 and 7,153,499. The terms IRX-2, primary cell-derived biologic, and NCM are used interchangeably herein.

Briefly, IRX-2 is prepared in the continuous presence of a 4-aminoquinolone antibiotic and with the continuous or pulsed presence of a mitogen, which in the preferred embodiment is PHA. Other mitogens, however, can also be used. The IRX-2 produced for administration to patients contains a concentration of IL-1β that ranges from 60-6,000 pcg/mL, more preferably, from 150-1,800 pcg/mL; a concentration of IL-2 that ranges from 600-60,000 pcg/mL, more preferably, from 3,000-12,000 pcg/mL, and concentrations of IFN-γ and TNF-α that range from 200-20,000 pcg/mL, more preferably, from 1,000-4,000 pcg/mL.

IRX-2 can also contain a concentration of IL-6 that ranges from 60-6,000 pcg/mL, more preferably, from 300-2,000 pcg/mL; a concentration of IL-8 that ranges from 6000-600,000 pcg/mL, more preferably from 20,000-180,000 pcg/mL; a concentration of TNF-α that ranges from 200-20,000 pcg/ml, more preferably, from 1,000-4,000 pcg/mL. Recombinant, natural or pegylated cytokines can be used, or IRX-2 can include a mixture of recombinant, natural or pegylated cytokines. IRX-2 can contain only the above cytokines; however, other cytokines can be included. The IRX-2 of the present invention can further include other recombinant, natural or pegylated cytokines such as IL-7, IL-12, IL-15, GM-CSF (at a concentration that ranges from 100-10,000 pcg/mL, more preferably from 500-2,000 pcg/mL), and G-CSF. The method of making IRX-2 is disclosed in the above cited patents as well as in U.S. Provisional Patent Application No. 61/044,674.

Also encompassed by the present invention are derivatives, fragments and peptides related to the cytokines disclosed herein, wherein such derivatives, fragments and peptides retain the biological activity of their respective cytokines.

Figure 2A:
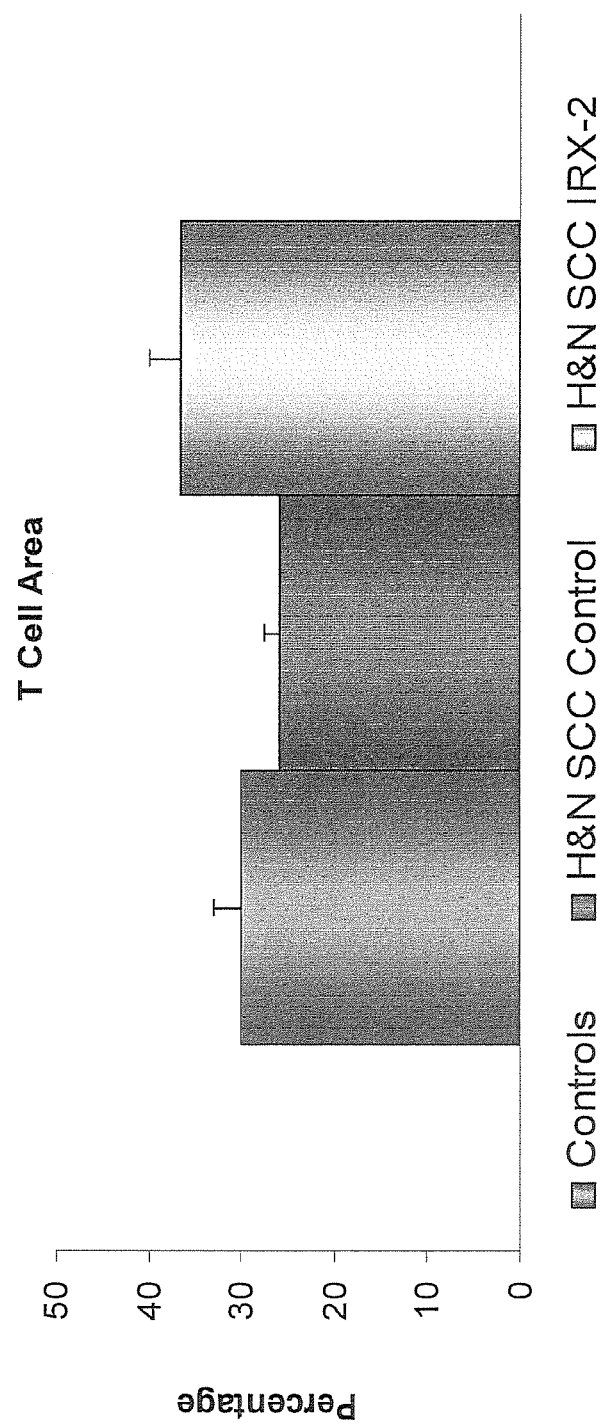
FIG. 2A is a bar graph showing T cell area and FIG. 2B shows density in normal controls, H&NSCC controls and H&NSCC patients treated with IRX-2.
Figure 2B:
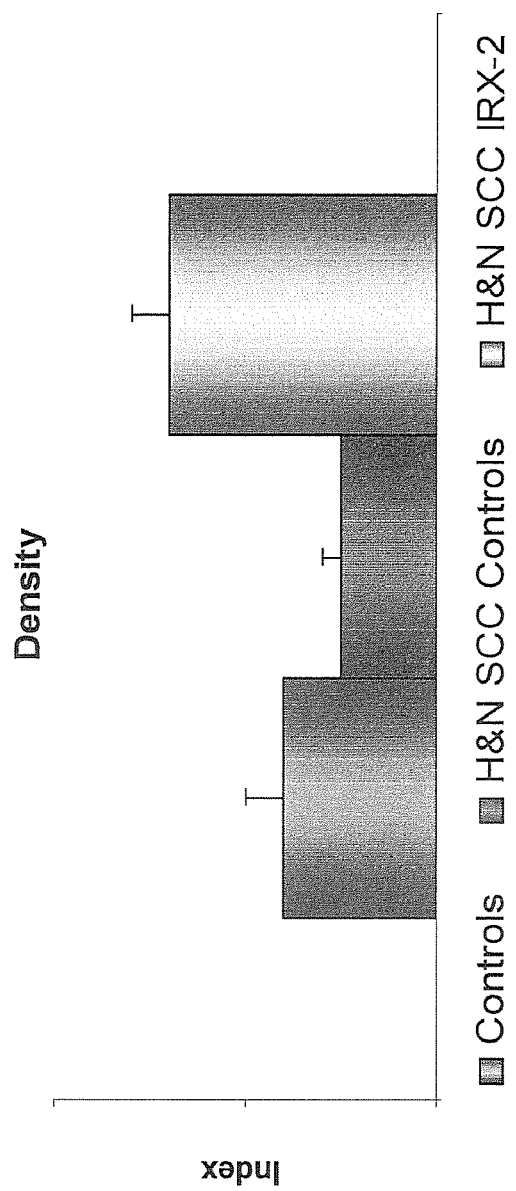
Figure 3A:
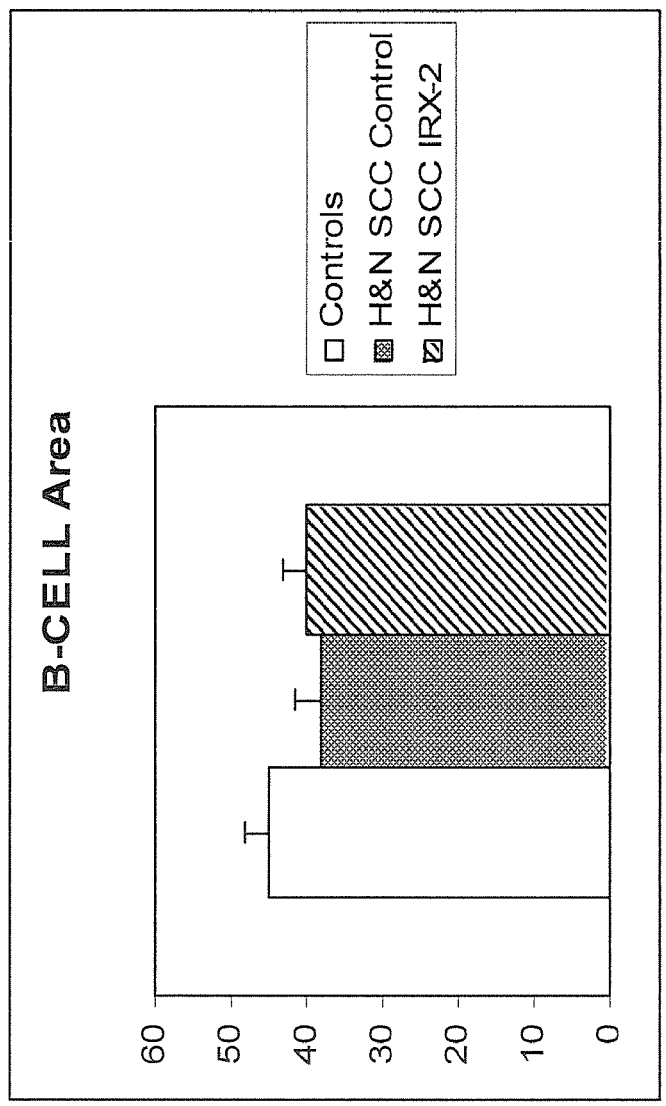
FIG. 3A is a bar graph comparing B cell area and FIG. 3B is a bar graph comparing follicles in the three treatment groups.
Figure 3B:
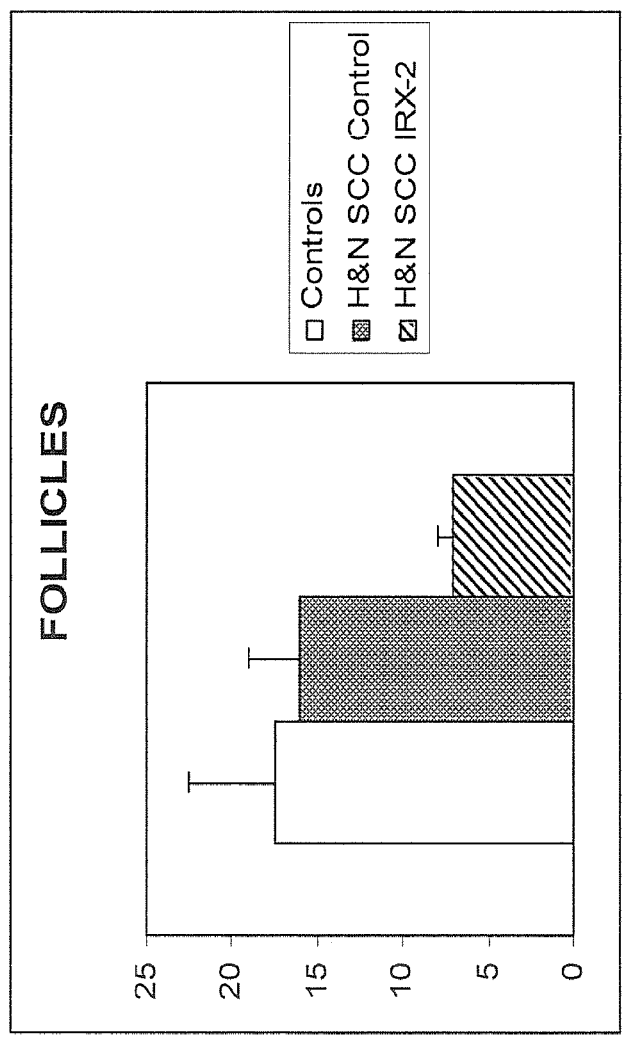
Figure 4A:
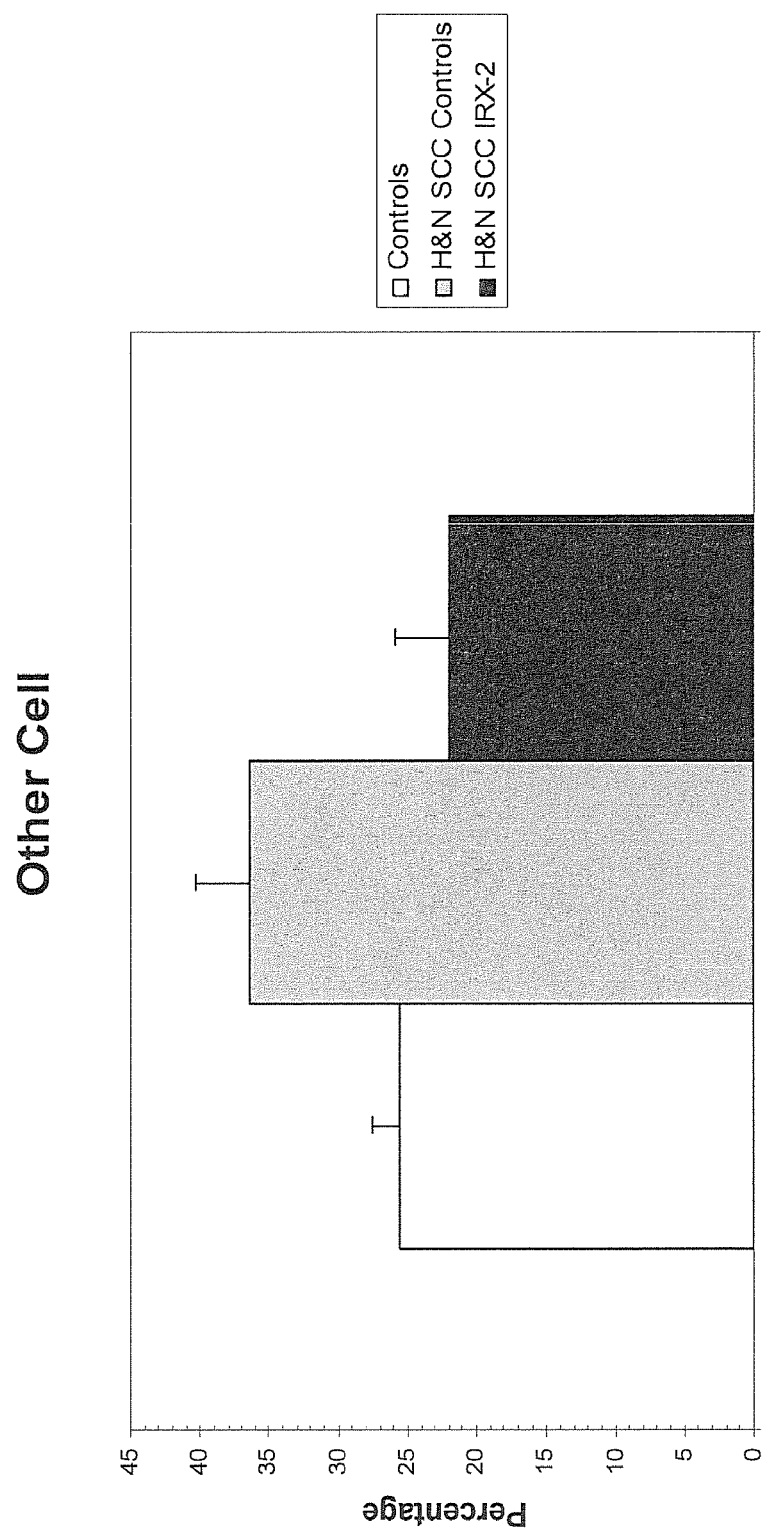
FIG. 4A shows a comparison of other cells and FIG. 4B shows a comparison of sinus histiocytosis (SH) in the three treatment groups.
Figure 4B:
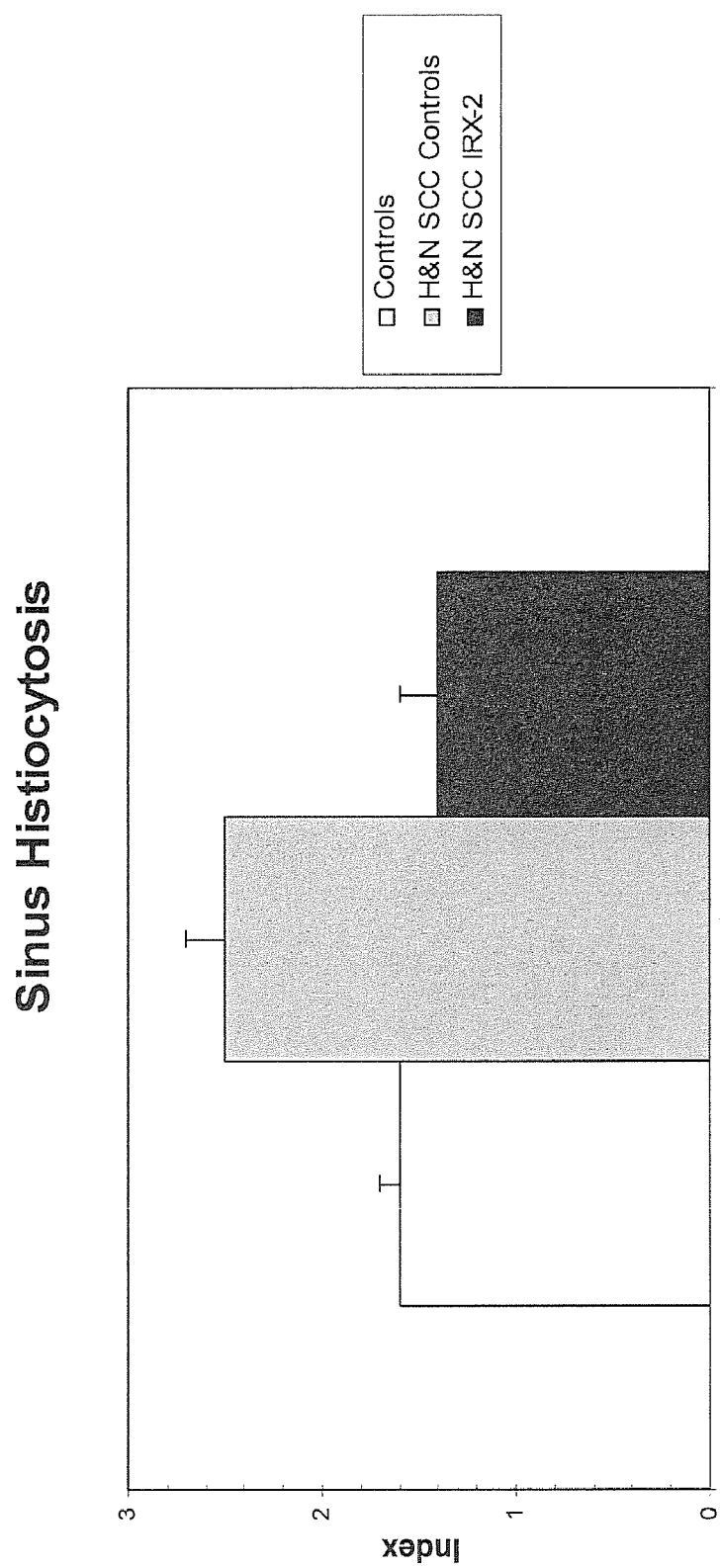

Other compounds can also be administered along with IRX-2, such as compositions for promoting immune suppression, such as chemical inhibitors; non-steroidal anti-inflammatory drugs (NSAIDS); zinc; and combinations thereof. The chemical inhibitor can be any chemotherapeutic agent that is not immunosuppressive (preferably used at low doses) and that has immunomodulatory effects so as to increase immunity and/or an immune response, e.g., by inhibiting immune suppression or suppressor mechanisms in the body. According to a preferred embodiment, the chemical inhibitor is an anti-neoplastic agent, including but not limited to alkylating agents, antimetabolites and antibiotics. The chemical inhibitor can also be an immunomodulating agent such as thalidomide. The chemical inhibitor can also be in a salt or other complex form. Preferably, the chemical inhibitor is the alkylating agent cyclophosphamide (CY). The NSAID is preferably indomethacin (INDO), which is both a CoxI and CoxII inhibitor. The NSAID can also be ibuprofen or CoxII inhibitors such as celecoxib and rofecoxib, or combinations thereof. The four components used together (i.e. chemical inhibitor, NSAID, primary cell derived biologic, and zinc) are able to address the suppressive environment created by the immune target and restore the cellular immune response of the patient. More specifically, the chemical inhibitor inhibits T regulatory cells; the NSAID reverses local immune suppression by prostaglandins the primary cell derived biologic activates dendritic cells, stimulates T cells, and protects T cells from apoptosis; and zinc provides key nutrients for T cell function as shown in FIG. 2. This combined action encourages immune response to both endogenous and exogenous antigens.

As used herein, the term "endogenous antigen" denotes an antigen that is produced and situated in vivo, i.e., within an organism such as a patient, such that, after the administration of the cytokine composition of the invention in vivo, the cytokines act as an adjuvant with the antigen within the patient to stimulate an immune response to the antigen.

As used herein, the term "exogenous antigen" denotes an antigen that is produced, i.e., isolated or generated, in vitro, i.e., outside of an organism to be treated, and is administered to the organism (i.e., a patient) in vivo, such that, after the administration of the cytokine composition of the invention in vivo, the cytokines act as an adjuvant with the antigen within the patient to stimulate an immune response to the antigen. The exogenous antigen can be a chemically synthesized or genetically engineered compound or molecule or can be an endogenous antigen that has been extracted from its in vivo environment and isolated in vitro. The extracted antigen can be processed or otherwise modified for re-introduction in vivo. The exogenous antigen can be administered either in a separate pharmacological preparation from the cytokine composition of the invention or in the same preparation. As demonstrated by the data of Examples 11 and 12 below, the IRX-2 composition of the invention is effective in combination with exogenous prostate-specific membrane antigens (PSMA) in promoting immune responses in both mice and humans. Other exogenous antigens can be combined with IRX-2 as further described below.

As used herein, the term "tumor associated antigen" denotes a protein or peptide or other molecule capable of inducing an immune response to a tumor. This can include, but is not limited to, PSMA peptides, MAGE peptides (Sahin, 1997; Wang, 1999), Papilloma virus peptides (E6 and E7), MAGE fragments, NY ESO-1 or other similar antigens. Previously, these antigens were not considered to be effective in treating patients based either on their size, i.e., they were considered too small, or they were previously thought to lack immunogenic properties (i.e., they were considered to be self antigens).

Synthetic long peptides are defined as peptide sequences between 22 and 45 amino acids. Synthetic long peptides vaccines offer several advantages over minimal peptide sequence vaccines, which are explained below. One of the key factors in vaccine efficacy is the context in which peptides are presented to the immune system. Synthetic long peptides are not able to bind directly to MHC class I but need to be taken up and processed by dendritic cells and then presented to cytotoxic T cells. In contrast, minimal cytotoxic T cells peptides (8-10 amino acids), are readily loaded exogenously in MHC class I molecules and can be presented by both professional APC (DC) and non-professional APC (T cells and B cells) in vivo. The presentation of cytotoxic T cells peptide epitopes on non-activated B cells induces a transient cytotoxic T cells response which is followed by a subsequent deletion of these CD8+ T-cells. The slow release and long duration of antigen presentation that is induced by the IFA adjuvant—more than 100 days—in combination with minimal presentation of cytotoxic T cells peptides in non-inflammatory lymph nodes by non-professional APC induces CD8+ T-cell tolerance and fratricide when peptide vaccine-activated CD8+ T-cells present the minimal cytotoxic T cells peptide to one another. In contrast, loading of minimal MHC class I binding peptides directly onto DC can convert a cytotoxic T cell tolerizing peptide into a peptide that triggers the expansion of a tumor-protective cytotoxic T cell response. Similarly, extension of the cytotoxic T cells peptide sequence to a synthetic long peptide, that requires professional processing by DC, has the same beneficial. Synthetic long peptides are primarily processed and presented by professional APC and therefore stimulate cytotoxic T cells predominantly within the strong stimulatory environment of the inflamed draining lymph. Another advantage of synthetic long peptides vaccines over minimal cytotoxic T cells peptide vaccines is the increased duration of in vivo epitope presentation in the antigen draining lymph node, which is important for clonal expansion and for IFN-γ production by effector T-cells. This improved in vivo presentation and concomitant induction of T-cell expansion by an synthetic long peptide epitope is particularly apparent if the cytotoxic T cells epitope concerned displays weaker MHC class I binding. Therefore, conversion of minimal cytotoxic T cells peptides to long peptides offers an alternative to methods such as modification of cytotoxic T cells peptides in order to increase immunogenicity.

Examples of synthetic long peptides for HPV are as follows:

| | |
|---|---|
| E61-32: | MHQKRTAMFQDPQERPRKLPQLCTELQTTIHD (SEQ ID NO: 4); |
| E619-50: | LPQLCTELQTTI HDIILECVYCKQQLLRREVY (SEQ ID NO: 5); |
| E641-65: | KQQLLRREVYDFAFRDLCIVYRDGN (SEQ ID NO: 6); |
| E655-80: | RDLCIVYRDGNPYAVCDKCLKFYSKI (SEQ ID NO: 7); |
| E671-95: | DKCLKFYSKISEYRHYCYSLYGTTL (SEQ ID NO: 8); |
| E685-109: | HYCYSLYGTTLEQQYNKPLCDLLIR (SEQ ID NO: 9); |
| E691-120: | YGTTLEQQYNKPLCDLLIRCINCQKPLCPEEK (SEQ ID NO: 10); |
| E6109-140: | RCINCQKPLCPEEKQRHLDKKQRFHNIRGRWT (SEQ ID NO: 11); |
| E6127-158: | DKKQRFHNIRGRWTGRCMSCCRSSRTRRETQL (SEQ ID NO: 12); |
| E71-35: | MHGDTPTLHEYMLDLQPETTDLYCYEQLNDSSEEE (SEQ ID NO: 13); |
| E722-56: | LYCYEQLNDSSEEEDEIDGPAGQAEPDRAHYNIVT (SEQ ID NO: 14); |
| E743-77: | GQAEPDRAHYNIVTFCCKCDSTLRLCVQSTHVDIR (SEQ ID NO: 15); |
| E764-98: | TLRLCVQSTHVDIRTLEDLLMGTLGIVCPICSQKP (SEQ ID NO: 16). |

More specifically, the present invention is directed to a composition including synergistic amounts of a primary cell-derived biologic (IRX-2) having the cytokines IL-1, IL-2, IL-6, IL-8, TNF-α, and IFN-γ, and a cancer vaccine including at least one antigen. IRX-2 acts as an adjuvant alone or in combination with other adjuvants to the exogenous antigen(s) in the vaccine, i.e. it stimulates an immune response to the exogenous antigen. In other words, IRX-2 acts in a synergistic manner with the exogenous antigen to create a greater immune response than can be achieved by administering the exogenous antigens alone. IRX-2 provides advantages over previous adjuvants because of its affect of completely "turning on" the immune system of a patient whose immune system is in any way suppressed from its full function. Without reversing suppression of the immune system, antigen cannot be presented effectively to treat cancer and other diseases. The mechanism by which IRX-2 "turns on" the immune system is further described below.

The composition can be used to treat many different types of diseases such as cancers, such as, but not limited to, head and neck squamous cell carcinoma (H&NSCC), breast cancer, colorectal cancer, stomach cancer, pancreatic cancer, lung cancer, brain cancer, colon cancer, ovarian cancer, tongue cancer, pharynx cancer, prostate cancer, and melanoma. In addition, the compositions and methods of the invention can be used to treat non-cancerous persistent lesions such as infectious lesions that produce an antigen in vivo, e.g., cutaneous or systemic candidiasis, papilloma virus-associated venereal warts, or cervical dysplasia.

The IRX-2 is essentially as described above in the definitions section and can optionally include additional cytokines other than the six critical cytokines of IL-1, IL-2, IL-6, IL-8, TNF-α, and IFN-γ, and the composition can optionally further include the various other compounds that are administered in the typical IRX-2 regimen, i.e., a chemical inhibitor, an NSAID, and zinc also as described above.

The vaccine of the present invention is any vaccine that is used to treat cancer by stimulating an immune response to a particular antigen and generally includes at least one antigen commonly produced in that particular type of cancer. While the antigens discussed herein are referred to as being in a "cancer vaccine", it should be understood that the antigens can also be used individually or in combination without being in a traditional "vaccine" in the same manner described herein, such as in Examples 11 and 12.

Common antigens used in cancer vaccines include AFP, alpha-actinin-4, ARTC1, BAGE, BCR-abl, B-RAF, CA 15-3, CA 19-9, CA-125, CASP-5, CASP-8, beta.-catenin, carcinoembryonic antigen, modified carcinoembryonic antigen, carcinoma-associated mutated mucins, cdc27, CDK4, CDKN2A, CEA, chromogranin A, COA-1, cyclin dependent kinase-4, dek-can fusion protein, EFTUD, elongation factor 2, epidermal growth factor receptor EGFRvIII, Epstein Barr Virus EBNA gene product, ETA, ETV6-AML1 fusion protein, FLT3-ITD, FN1, GAGE, gangliosides, GPNMB, gp75/TRP-1, gp100, H1FT, HAGE, HERV-K-MEL, HER2/neu protein, HIP-55, HIV-1, HIV-2, HLA-A2, HLA-A11, hsp70-2, KIAAO205, kinesin 2, KK-LC-1, KLK-4, KM-HN-1, KSA, LAGE, LDLR-fucosyltransferaseAS fusion protein, MAGE, mammaglobin-A, MART-1/Melan A, MART-2, ME1, melanoma proteoglycan, myosin class I, MUC-1, MUM-1, MUM-2, MUM-3, NA-88, NCAM-180, neo-PAP, NFYC, NY-BR, NY-ESO-1, OA1, OGT, OS-9, p15, p21-ras, p53, p185 HER2/neu, papilloma virus E7, papilloma virus E6, pmi-RARalpha fusion protein, PRDX5, PTPRK, PSA, PSMA, RAGE, K-ras, N-ras, RAB38, RBAF600, SAGE, SIRT2, SNRPD1, sp17, SYT-SSX1 fusion protein, SYT-SSX2 fusion protein, TA 90, TAG, TGF-β1 anti-apoptotic factor, TGF-βRII, thyroglobulin, TRAG-3, triosephosphate isomerase, TRP2, TRP2-INT2, tumor protein D52, tyrosinase, WT1, fragments thereof, derivatives thereof, and combinations thereof. Any other suitable antigen can also be used.

The antigens administered can be the antigens themselves in the form of naturally occurring proteins, recombinant proteins, chemically synthesized proteins, or combinations thereof.

Furthermore, the antigens can be encoded in a viral or bacterial vector, i.e. a nucleic acid vector. In this case, the antigen is encoded in nucleic acid material, such as DNA or RNA. Common viral vectors used for encoding nucleic acid include, but are not limited to, retrovirus, adenovirus, adeno-associated virus (AAV), herpes virus, and poxvirus. Examples of poxvirus include vaccinia, modified vaccinia Ankara (MA), NYVAC, avipox, TROVAX, fowlpox, and canarypox. Specific examples of canarypox include ALVAC and ALVAC(2). One skilled in the art can encode the antigens in the desired vector.

The composition can further include co-stimulatory molecules to stimulate T cells. T cells require two different signals in order to become fully activated. The first signal is antigen-specific and comes from the T cell receptor interacting with peptide-MHC molecules on the membrane of antigen presenting cells. The second signal, which is the co-stimulatory signal, is antigen non-specific and is achieved by the interaction between co-stimulatory molecules expressed on the membrane of antigen presenting cells and the T cell. Co-stimulatory molecules can be found naturally in the body; however, in an immune suppressed patient, additional molecules can be administered. Examples of co-stimulatory molecules include abatacept, belatacept, CD28-SuperMAB, B7/CD28 co-stimulatory molecules, TNF superfamily co-stimulatory molecules, SLAM family co-stimulatory molecules as well as others.

The composition can also include synthetic long peptides as described above. This combination is an example of combining a vaccine having a novel mechanism of action with the composition of the present invention to gain a synergistic response due to the combined mechanism of action of the two components.

The composition can also include compounds for blocking suppressive or negative regulatory immune mechanisms, such as anti-CTLA-4, anti-PD-1 or anti-PDL-1. The CTLA-4 (Cytotoxic T-Lymphocyte Antigen 4) family of recepts, when engaged, inhibits activation of T cells, promotes cell cycle arrest, and decreased cytokine production. This is an important function in a normally functioning immune system to prevent excessive immune responses. However, inhibiting the CTLA-4 receptor in an immune suppressed patient is desired in order to remove some of the suppression and stimulate the activation of T cells.

The composition can further include a Treg depleting molecule. Tregs, or regulatory T cells, distinguish between self-antigens and non-self antigens and actively suppress immune activation. Depletion of Tregs can reduce suppression of the immune system in an immune suppressed patient. This depletion can be accomplished by administering a Treg depleting molecule such as, but not limited to, denileukin difitox (ONTAK®, Eisai Inc.).

The composition can include angiogenesis-associated antigens in order to prevent or inhibit angiogenic processes occurring near or within tumors. Angiogenesis-associated antigens can include, but are not limited to, VEGF, VEGF receptor, EGFR, bFGF, PDGF-B, PD-ECGF, TGFs including TGF-α, endoglin, Id proteins, various proteases, nitric oxide synthase, aminopeptidase, thrombospondins, k-ras, Wnt, cyclin-dependent kinases, microtubules, heat shock proteins, heparin-binding factors, synthases, collagen receptors, integrins, and surface proteoglycan NG2.

The composition can further include potentiating agents CD80, ICAM-1, and LFA-3, also known as TRICOM, for potentiating the effect of the primary cell-derived biologic and cancer vaccine as well as the other components described above. Other combinations of potentiating agents include IL-12 and GM-CSF; IL-12, GM-CSF, and TNF-α; CD80 and IL-12; and CD86, GM-CSF, and IL-12.

The present invention also encompasses the use of both an endogenous antigen and an exogenous antigen, i.e., wherein the composition is administered to a patient having an endogenous antigen in vivo and wherein the cytokines act as an adjuvant with both the exogenous and endogenous antigens to stimulate immune responses in the patient. For example, the endogenous antigen can be present in regional lymph nodes or at the tumor site.

The present invention is also directed to a composition including the primary cell-derived biologic as described above, which itself acts as an adjuvant, and at least one other adjuvant in order to stimulate the immune system of a patient. Exogenous antigen(s) such as in the cancer vaccines and the other components described above can also be included in the composition. In other words, the composition is a multi-adjuvant composition that further enhances the effect of the antigens. Furthermore, the primary cell-derived biologic not only potentiates the effect of the antigens as described above, but also the effect of the adjuvants, i.e. the primary cell-derived biologic acts synergistically with the adjuvants.

There are two different classes of adjuvants: toll-like receptor (TLR)-independent and TLR-dependent. TLR-independent adjuvants act as delivery systems and help to concentrate antigens, target them to antigen-presenting cells, and colocalize antigens and immune potentiators. TLR-dependent adjuvants directly stimulate the immune system through activation of TLRs. The composition of the present invention can be used with a TLR-independent adjuvant, a TLR-dependent adjuvant, or combinations thereof. Using each kind of adjuvant can stimulate different parts of the immune system at once. For example, a TLR-independent adjuvant can traffic antigen and TLR-dependent adjuvants to APCs to stimulate antigen uptake and stability, while the TLR-dependent adjuvant directly enhances immunity through activation of TLR signaling and reduces potential toxicity of administering TLR-dependent adjuvants on their own. Also, using multiple TLR-dependent adjuvants can result in a synergistic effect of the adjuvants.

The adjuvants can be, but are not limited to, the following adjuvants. TLR-independent adjuvants: Alum (aluminum phosphate/hydroxide) is a mineral salt with various indications. AS03 (GSK; squalene (10.68 mg), DL-alpha-tocopherol (11.86 mg), and polysorbate 80 (4.85 mg) is an oil in water emulsion that is used for pandemic influenza. MF59 (Novartis; 4-5% w/v squalene, 0.5% w/v Tween 80, 0.5% Span 85, optionally: varying amounts of muramul tripeptide phosphatidyl-ethanolamine (MTP-PE)) is an oil in water emulsion used for influenza. Provax (Biogen Idec; squalene plus pluronic L121) is an oil in water emulsion. Montanide (Seppic SA; Bioven; Cancervax; mannide oleate and mineral oil) is a water in oil emulsion that is used in treating malaria and cancer. TiterMax (CytRx; squalene plus CRL-8941) is a water in oil emulsion. Advax (Vaxine Pty; nanocrystalline particles of inulin) is a biopolymer that is used in vaccines against Hepatitis B (prophylactic and therapeutic), influenza, anthrax, *shigella*, Japanese encephalitis, rabies, bee venom, allergy, and cancer immunotherapy. QS21 (Antigenics; fraction of Quil A) is a plant-derived composition that is used in treating melanoma, malaria, HIV, and influenza. Quil A (Statens Serum Institute; purified fraction of *Quillaja saponaria*) is a plant-derived composition used in various treatments. ISCOM (CSL; Isconova; saponin plus sterol plus, optionally, phospholipid) is a plant-derived composition that is used in various treatments including influenza. Liposomes (Crucell; Nasvax; synthetic phospholipid spheres consisting of lipid) are used in treating various disease.

TLR-dependent adjuvants: Ampligen (Hemispherx; synthetic specifically configured double-stranded RNA containing regularly occurring regions of mismatching) works by activation of TLR3 and is used as a vaccine against pandemic flu. AS01 (GSK; MPL, liposomes, and QS-21) works by MPL-activation of TLR4, liposomes provide enhanced antigen delivery to APCs, QS-21 provides enhancement of antigen presentation to APCs and induction of cytotoxic T cells, and this is used as a vaccine against malaria and tuberculosis. AS02 (GSK; MPL, o/w emulsion, and QS-21) works by MPL-activation of TLR4, the o/w emulsion provides innate inflammatory responses, APC recruitment and activation, enhancement of antigen persistence at injection site, presentation to immune-competent cells, elicitation of different patterns of cytokines, and the QS-21 provides enhancement of antigen presentation to APCs and induction of cytotoxic T cells, and this is used as a vaccine against malaria, tuberculosis, HBV, and HIV. AS04 (GSK; MPL, aluminum hydroxide/aluminum phosphate) works by MPL-activation of TLR4, alum provides a depot effect, local inflammation, and increase of antigen uptake by APCs, and this is used as a vaccine for HBV, HPV, HSV, RSV, and EBV. MPL RC-529 (Dynavax; MPL) works by activation of TLR4 and is used as a vaccine against HBV. E6020 (Eisa/Sanofi Pasteur; synthetic phospholipid dimer) works by activation of TLR4. TLR-technology (Vaxinnate; antigen and flagellin) works by activation of TLR5 and is used in vaccines against influenza. PF-3512676 (CpG 7909) (Coley/Pfizer/Novartis; immunomodulating synthetic oligonucleotide) works by activation of TLR9 and is used in vaccines against HBV, influenza, malaria, and anthrax. ISS (Dynavax; short DNA sequences) works by activation of TLR9 and is used in vaccines against HBV and influenza. IC31 (Intercell; peptide and oligonucleotide) and works by activation of TLR9, formation of an injection site depot, and enhancing of antigen uptake into APCs and is used as a vaccine against influenza, tuberculosis, malaria, meningitis, allergy, and cancer indications.

It should also be understood that the primary cell-derived biologic and adjuvant combinations can be used for other indications than those currently recommended for the above adjuvants, and they especially can be used for cancer indications as described herein. Thus, the primary cell-derived biologic and adjuvant combination can be used to enhance the immune system and treat any of the diseases indicated specifically for the adjuvants or for any other disease described herein.

Furthermore, the present invention can include the primary cell-derived biologic and another adjuvant as described above that has a different mechanism of action than that of the primary cell-derived biologic. The primary cell-derived biologic acts to effectively "turn on" the immune system by maturing immature dendritic cells, stimulate the production of naïve T cells, and effectively present antigen to the naïve T cells. The mechanism of action is further described below. When combined with an adjuvant that acts on another area of the immune system, the primary cell-derived biologic and adjuvant can produce a synergistic response in the immune system by stimulating multiple areas of the immune system at once.

The present invention provides for a method of treating cancer, by administering the composition described above including synergistic amounts of the primary cell-derived biologic including the cytokines IL-1, IL-2, IL-6, IL-8, TNF-α, and IFN-γ, and a cancer vaccine comprising at least one antigen. The composition is effective at treating cancer because the primary cell-derived biologic and the antigens interact in a synergistic manner to present antigens to T cells and activate the immune system. In general, the primary cell-derived biologic acts to stimulate the production of naïve T cells, mature immature dendritic cells, and allow presentation by resulting mature dendritic cells of the exogenous antigens in the cancer vaccine to the naïve T cells. The mechanism of action is further described below. In other words, without the action of the primary cell-derived biologic, the cancer vaccine would not be as effective in generating immunity to the cancer in the patient because the immune system would remain suppressed. The administration step can be achieved as further described below, and preferably by perilymphatic injection once daily.

T cells in the patient can also be co-stimulated by administering co-stimulatory molecules as described above to generate antigen non-specific signals to T cells. Inhibition of T cells can be prohibited by administering anti-CTLA-4 as described above in order to further stimulate the T cells as described above. Tregs can be depleted by administering Tregs depleting molecules in order to further reduce suppression of the immune system as described above. Induction and continued development of blood vessels in tumors can be prevented by administering angiogenesis-associated antigens as described above. Potentiating agents can be administered that potentiate the effect of the components of the composition as described above.

The method of treating cancer can further include performing a therapy such as chemotherapy, radiation, anti-angiogenic therapy, and combinations thereof. Each of these therapies is more effective when performed in combination with the composition of the present invention than when performed alone.

The present invention also provides for a method of reversing immune suppression and gaining immunity to cancer by administering the composition described above including synergistic amounts of the primary cell-derived biologic including the cytokines IL-1, IL-2, IL-6, IL-8, TNF-α, and IFN-γ, and a cancer vaccine comprising at least one antigen, stimulating the production of naïve T cells, maturing immature dendritic cells, and allowing presentation by resulting mature dendritic cells of the exogenous antigens in the cancer vaccine to the naïve T cells, thereby reversing immune suppression and gaining immunity to the cancer. In other words, the primary cell-derived biologic and the cancer vaccine work together in order to effectively turn on the immune system in the immune suppressed patient and stimulate immunity to the cancer based on the exogenous antigens.

As in the above method, T cells in the patient can also be co-stimulated by administering co-stimulatory molecules as described above to generate antigen non-specific signals to T cells. Inhibition of T cells can be prohibited by administering anti-CTLA-4 as described above in order to further stimulate the T cells as described above. Tregs can be depleted by administering Tregs depleting molecules in order to further reduce suppression of the immune system as described above. Induction and continued development of blood vessels in tumors can be prevented by administering angiogenesis-associated antigens as described above. Potentiating agents can be administered that potentiate the effect of the components of the composition as described above.

The method of reversing immune suppression and gaining immunity to cancer can further include performing a therapy such as chemotherapy, radiation, anti-angiogenic therapy, and combinations thereof. Each of these therapies is more effective when performed in combination with the composition of the present invention than when performed alone.

The present invention also provides for a method of producing an immune response to an exogenous antigen in a patient, by administering an adjuvant of a primary cell-derived biologic including the cytokines IL-1, IL-2, IL-6, IL-8, TNF-α, and IFN-γ, and at least one exogenous antigen, wherein the exogenous antigen does not normally produce an immune response, and producing an immune response in the patient. The exogenous antigens can be any of those described above that normally do not produce an immune response in a patient. Example 12 shows that IRX-2 is effective in producing an immune response with PSMA peptides that are not normally effective. This method can further be combined with any of the steps or compounds as described above.

The present invention provides for a method of enhancing an immune response in a patient, by administering the primary cell-derived biologic including the cytokines IL-1, IL-2, IL-6, IL-8, TNF-α, and IFN-γ, in combination with at least one adjuvant. The primary cell-derived biologic is described above. The adjuvant(s) can be a TLR-independent adjuvant, a TLR-dependent adjuvant, or combinations thereof. The method can then include the step of delivering and concentrating antigens, targeting antigens to antigen-presenting cells, and colocalizing antigens and immune potentiators by administering a TLR-independent adjuvant. The method can also include the step of directly stimulating the immune system by activating TLRs by administering a TLR-dependent adjuvant. As described above, the primary cell-derived biologic acts synergistically with the other adjuvants to more effectively stimulate the immune system in response to antigens. Preferably, exogenous antigens are also administered as described above such as in the cancer vaccine. This method can further be combined with any of the steps or compounds as described above. The adjuvant can have a different mechanism of action than the primary cell-derived biologic as described above.

The present invention further provides for a method of increasing function of an immune system by administering the primary cell-derived biologic including the cytokines IL-1, IL-2, IL-6, IL-8, TNF-α, and IFN-γ, in combination with at least one adjuvant, wherein the adjuvant has a mechanism of action that is different than the mechanism of action of the primary cell-derived biologic, and increasing function of the immune response. In other words, the primary cell-derived biologic and the adjuvant interact synergistically to increase immune function beyond what would result from the primary cell-derived biologic or adjuvant alone because each component is "turning on" a different area of the immune system, to produce a greater immune response. This method can further be combined with any of the steps or compounds as described above.

The Mechanism of Action of IRX-2

As defined above, the primary cell-derived biologic of the invention acts as an adjuvant, i.e., stimulates or enhances the immune response of a patient to a particular antigen. Moreover, the IRX-2 compositions and methods of the invention are particularly suited to stimulate T cell-mediated immune responses. Immune responses promoted by the compositions and methods of the invention include the induction or generation of naïve T cells, the differentiation and maturation of dendritic cells, allowing for proper presentation of antigen to T cells (e.g., in the lymph nodes), and the activation of monocytes and macrophages. Specifically, in cancer patients, immune responses promoted by the compositions and methods of the invention include tumor infiltration by lymphocytes, tumor fragmentation and regression as well as a reduction in sinus histiocytosis (when present). Essentially, the primary cell-derived biologic induces immune production and blocks immune destruction. The mechanism of action of the primary cell-derived biologic is further described in U.S. patent application Ser. No. 12/323, 595 to Applicants.

More specifically, the compositions and methods of the present invention aid in overcoming immune depression/ suppression in patients by inducing the production of naïve T cells. The term "naïve" T cells, as defined herein, denotes newly produced T cells, which T cells have not yet been exposed to antigen. Such T cells are non-specific, yet are capable of becoming specific upon presentation of antigen by a mature dendritic cell having antigen, such as tumor peptides, exposed thereon. Thus, the compositions and methods of the invention replenish or generate new T cells (see Examples 2 and 8 below).

In addition, particularly in cancer patients having tumors, the present compositions and methods allow for lymphocyte infiltration into the tumors with significant tumor fragmentation and regression. See, e.g., Examples 2-7 below. Such infiltration is important in order to maximize clinical response and for the greatest increase in survival rate. For example, lymphocyte:granulocyte or macrophage infiltration of a 90:10 ratio is optimal and T and/or B cell infiltration is preferably diffuse and intense and not peripheral. Tumor reduction and fragmentation in histological samples reflects a good immune response and is indicative of an adjuvant effect by the compositions of the invention.

Moreover, specific lymph node changes also indicate an effective immune response, such as lymph node enlargement, i.e., not just reversal of tumor-induced reduction of size but overall increase in size compared to the normal node size, as well as increased T and B cell areas. In addition, the lymph nodes of cancer patients often contain an intrasinusoidal accumulation of large histiocytes, also termed sinus histiocytosis (SH). SH is believed to be the accumulation of immature dendritic cells, which have ingested and processed tumor antigens but are unable to mature and present these tumor peptides to naive T cells. Without the proper presentation of antigen to T cells, these T cells are incapable of stimulating Th1 and Th2 effector cells, which stimulation normally leads to cell-mediated and antibody-mediated immunity, respectively, in the body. As indicated in Examples 2-7 below, the cytokine compositions and methods of this invention reduced SH in the lymph nodes of cancer patients and produced the various lymph changes described above, again indicating an adjuvant effect by the compositions of the invention.

Because dendritic cells are known to play such a key role in antigen presentation in the production of an appropriate immune response in vivo, an agent having a stimulatory effect on dendritic cell maturation will act as an adjuvant in eliciting a good immune response to an antigen. As demonstrated in Example 9 below, the cytokine compositions of the present invention promote dendritic cell maturation. Furthermore, the data of Example 2 demonstrate that the cytokine compositions of the invention also unblock the dendritic cell defect that leads to SH, i.e., by promoting DC maturation, and thus specifically, in cancer patients, the compositions of the invention provide multiple adjuvant effects, i.e., in unblocking DCs in SH in the lymph nodes and in promoting DC maturation generally.

The cytokine compositions of the invention also provide a further adjuvant effect by acting as potent activators of monocytes/macrophages. Monocytes are precursors to both DCs and macrophages in the body and thus an agent that promotes monocyte/macrophage activation has an adjuvant effect on immune responses in vivo. See Example 10 below.

The primary cell-derived biologic also blocks immune destruction by protecting the activated T cells from apoptosis. One of the mechanisms of tumor escape involves targeted elimination of CD8+ effector T cells through apoptosis mediated by tumor-derived microvesicles (MV). Immunosuppressive MV have been found in neoplastic lesions, sera, ascites and pleural effusions obtained from cancer patients and have been linked to apoptosis and TCR alterations in effector T cells in these patients. MV-driven elimination of effector T cells, which are necessary for anti-tumor host defense, contributes to tumor escape and cancer progression. Therefore, protection of anti-tumor effector cells from functional impairments and death is a major objective of immune therapy. Clinical and experimental data show that certain cytokines, especially survival cytokines using the common receptor γ chain, are able to protect activated T cells from tumor-induced death and enhance their anti-tumor activity.

More specifically, there are several ways in which the primary cell-derived biologic protects T cells from apoptosis. The expression of anti-apoptotic signaling molecules (i.e. JAK-3 and phosphor-Akt) is up-regulated and the expression of pro-apoptotic molecules (i.e. SOCS-2) is down-regulated. Activation of caspases in CD8+ and CD4+ T lymphocytes is decreased and cFLIP expression is increased. Inhibition of the PI3K/Akt survival pathway is counteracted by IRX-2. The T cells are protected from both extrinsic apoptosis (MV-induced and FasL-induced apoptosis) and intrinsic mitochondrial apoptosis.

The protection from extrinsic MV-induced apoptosis is further accomplished by preventing down-regulation of JAK3, CD3-ζ, and STAT5; inhibiting dephosphorylation of Akt-½; and maintaining balanced ratios of Bax/Bcl-2, Bax-Bcl-xL, and Bim/Mcl-1. The protection from MV-induced apoptosis is also accomplished by preventing induction of the activity of caspase-3 and caspase-7. More specifically, the induction of the active cleaved form of caspase-3 is blocked, as is the loss of mitochondrial membrane potential. Nuclear DNA fragmentation is inhibited. Protection from intrinsic apoptosis by the primary cell-derived biologic is shown by its protection of activated T cells from staurosporine-induced apoptosis.

Importantly, the cytokines of the primary cell-derived biologic protect the activated T cells from apoptosis in a synergistic manner. In other words, the combination of the cytokines in the primary cell-derived biologic produces a greater affect than is seen by administering individual cytokines alone.

In view of the above, the compositions and methods of the present invention stimulate the immune system via multiple effects, including the in vivo maturation of dendritic cells resulting in effective peptide antigen presentation as well as activation of monocytes and macrophages and the production of naïve uncommitted T cells. The proper presentation of antigen leads to T and B cell clonal expansion, creating immunity in the patient. In the case of cancer patients, the effects noted above result in the infiltration, e.g., of lymphocytes, into tumors (e.g., via hematogenous spread) and tumor reduction and/or destruction. The result, as indicated by the data below, is increased survival due to immunologic memory (see, e.g., Example 3 below).

For any of the above embodiments, the following administration details and/or protocols for treatment are used:

Preferably, the cytokine composition of the present invention is injected around lymphatics that drain into lymph nodes regional to a lesion, such as a tumor or other persistent lesions being treated. More specifically, local perilymphatic injections or other injections that are known to those of skill in the art are administered to provide sufficient localization of the immunotherapy preparation. In the case of head and neck cancer, the injections are given in the neck, but can be applied in other locations as required by the disease to be treated. Such treatment induced clinical regressions in a high percentage of head and neck cancer patients, who also showed improved, recurrence-free survival (Hadden, 1994; Meneses, 1998; Barrera, 2000; Whiteside, 1993). In contrast, intratumoral injection of recombinant interleukin-2 in head and neck cancer patients (Whiteside, et al (Cancer Res. 53:5654-5662, 1993)) produced a T cell lymphocyte infiltrate, but no significant clinical responses. Similarly, peritumoral injection of Multikine (Celsci Website) in combination with perilymphatic injection resulted in significant tumor responses (i.e., greater than 50% tumor reduction) in only 11 patients, making their response rate less than 10%. Furthermore, peritumoral and intratumoral injection can be associated with progression of disease, even in patients who initially have had a positive response to the cytokine protocol, thus undoing its benefit. Peritumoral or intratumoral injection is thus contraindicated.

A ten (10) day injection scheme for administration of the compositions of the invention is preferred, but a twenty (20) day injection protocol can be used. Bilateral injections are effective. Where radical neck dissection has occurred, contralateral injection is effective.

In the embodiment wherein an exogenous antigen is to be utilized, exogenously provided synthetic or extracted antigens such as tumor antigen and peptides (see Bellone, 1998) can be administered into the pre-primed or co-primed regional or distal lymph node, either in a separate preparation or as part of the cytokine composition of the invention.

Endogenous suppression of T cells, which can be caused by, e.g., cancer or other immunosuppressive diseases, can be blocked by the co-administration of low dose cyclophosphamide (CY) and a non-steroidal anti-inflammatory drug (NSAID) (i.e., in combination with the cytokine compositions of the invention). The NSAID is preferably indomethacin (INDO) but ibuprofen or CoxII inhibitors such as celecoxib (CELEBREX®) or rofecoxib (VIOXX®) or combinations thereof can also be used. Side effects of NSAIDS can be aggressively treated with proton inhibitors and prostaglandin E analogs. Zinc and multi-vitamins, possibly including the addition of selenium, can also be added as agents to help restore T cell immunity. Preferably, the dose of zinc is 15 to 75 mg. A standard multivitamin can be administered. The zinc can be an available gluconate.

The cytokine compositions of the invention can be administered prior to or after surgery, radiotherapy, chemotherapy, or combinations thereof. The compositions of the invention can be administered during the recurrence of tumors, i.e., during a period where tumor growth is occurring again after a period where tumors were thought to have disappeared or were in remission.

The cytokine compositions of the present invention are administered and dosed to promote optimal immunization either to exogenous or endogenous antigen, taking into account the clinical condition of the individual patient, the site and method of administration, scheduling of administration, patient age, sex, and body weight. The pharmaceutically "effective amount" for purposes herein is thus determined by such considerations as are known in the art. The amount must be effective to promote immunization, leading to, e.g., tumor reduction, tumor fragmentation and leukocyte infiltration, delayed recurrence or improved survival rate, or improvement or elimination of symptoms, including increased T cell counts.

In the methods of the present invention, the compositions of the present invention can be administered in various ways. It should be noted that the cytokines or exogenous antigens used in the compositions of the invention can be administered in their standard forms or as pharmaceutically acceptable derivatives and can be administered alone or as active ingredients in combination with pharmaceutically acceptable carriers, diluents, adjuvants and vehicles. Furthermore, the compositions of the invention can be administered intra- or subcutaneously, or peri- or intralymphatically, intranodally or intrasplenically or intramuscularly, intraperitoneally, and intrathorasically. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

The doses can be single doses or multiple doses over a period of several days. When administering the compositions of the present invention, they are generally formulated in a unit dosage injectable form (e.g., solution, suspension, or emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, or vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, can also be used as solvent systems for the compositions of the invention. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it is desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent or additive used would have to be compatible with the cytokines or exogenous antigens of the invention.

Sterile injectable solutions can be prepared by incorporating the cytokines or exogenous antigens utilized in practicing the present invention in the required amount of the appropriate solvent with several of the other ingredients, as desired.

A pharmacological formulation of the present invention can be administered to the patient in an injectable formulation containing any compatible carrier, such as various vehicles, additives, and diluents; or the cytokines and/or exogenous antigens utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those disclosed in U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

It should be apparent that the compositions and methods of the invention are useful for the treatment of antigen-producing diseases such as cancer, infectious diseases or persistent lesions, as discussed above. The compositions and methods promote immunization against the antigens produced by these diseases by stimulating immune responses in patients in vivo, which immune responses help to alleviate or eliminate the symptoms and effects of the disease in the patient.

The above discussion provides a factual basis for the use of the present invention. The compositions and methods of the invention for use in the utilities disclosed herein can be shown by the following non-limiting examples and accompanying figures.

The examples set forth below describe the preparation of IRX-2, a cytokine mixture in accordance with this invention, data from clinical trials demonstrating the use of IRX-2 as an adjuvant with endogenous tumor antigens to stimulate immune responses in cancer patients as well as experiments in mice and humans demonstrating the use of the cytokine mixture of the invention with exogenous antigens to stimulate immune responses in vivo.

More specifically, Example 1 below describes the production of IRX-2, a cytokine composition in accordance with the present invention. The production of IRX-2 is fully disclosed in U.S. Pat. Nos. 5,632,983 and 5,698,194, which are incorporated herein by reference.

Example 2 below discloses clinical trial data wherein H&N SCC patients treated with IRX-2 (in combination with low dose cyclophosphamide (CY), indomethacin (INDO) and zinc) displayed significant clinical and pathological responses including nodal changes indicating immunization (e.g., increases in node size and decreases in sinus histiocytosis), tumor infiltration with lymphocytes, and tumor reduction and fragmentation. Examples 4-7 relate to additional cancer patients, i.e., with lymphoma, cervical cancer, liver cancer, and squamous cell carcinoma of the penis (human papilloma-virus associated), all of whom were treated with the IRX-2 of the invention and who showed significant clinical responses to the treatment. Example 3 provides data regarding the increased survival (up to 2 years) of the cancer patients of these studies.

As demonstrated in Example 2, treatment with IRX-2 also produced marked increases in T lymphocyte counts in T lymphocytopenic patients and a corresponding increase in naïve T cells (newly-produced T cells unexposed to antigen). Furthermore, as indicated by the data of Example 8 below, the increases in T cells observed in these studies was specifically due to treatment with the cytokine composition of the invention. More specifically, Example 8 provides data of the treatment of lymphocytopenic H&N SCC cancer patients with only IRX-2 (without the accompanying administration of CY and/or INDO), wherein significant increases in overall lymphocyte counts as well as specific CD3+ and CD4+ T cell subset populations were obtained.

Similarly, the data of Example 9 demonstrate that IRX-2 promotes the differentiation and maturation of dendritic cells as measured by morphologic, phenotypic and functional criteria. As noted above, dendritic cells (DCs) are known to play a critical role in the immunization of patients to antigens, i.e., by presenting antigen to the appropriate T cell. More specifically, Example 9 demonstrates that IRX-2 promotes morphologic changes in DCs indicative of maturation. IRX-2 also was shown to down-regulate CD1a antigen expression on the DC cell surface, to upregulate CD83 and MHC II antigen expression on the DC cell surface, and to increase the expression of T cell co-stimulatory and adhesion molecules, e.g., CD86, CD40, and CD54 (ICAM-1), on the DC cell surface. In addition, IRX-2 was shown to down-regulate the endocytic activity of DCs (which is consistent with maturation of the DCs), to enhance the T cell stimulatory activity of DCs (as demonstrated by increased MLR activity) and to increase the production of IL-12 from DCs, IL-12 itself being an essential factor in the differentiation of naïve CD4+ helper T cells (into Th1 cells) and the activation and proliferation of cellular and phagocytic components of the immune system. Finally, IRX-2 was shown to reduce VEGF-induced apoptosis of DCs. This anti-apoptotic effect of IRX-2 may play a crucial role in maintaining the survival of mature DCs within a tumor setting, allowing for prolonged antigen presentation and activation of tumor antigen-specific cytotoxic T lymphocytes.

The data of Example 10 below demonstrate further that IRX-2 is a potent activator of monocytes and macrophages. For example, IRX-2 significantly increases activation markers of monocytes/macrophages, i.e., HLA-DR, CD86, CD40 and CD80. In addition, the IRX-2 was shown to be a stronger activator of monocytes/macrophages than TNF-α or LPS and the IRX-2 was able to continue activating the cells even in the presence of the immunosuppressing cytokine IL-10.

Example 11 below demonstrates the ability of IRX-2 to elicit immune responses, i.e., in the form of DTH responses as well as antibody responses, in mice following administration of the cytokine composition in combination with exogenous prostate-specific membrane (PSMA) peptide antigen conjugates. The IRX-2 was also effective in stimulating DTH responses to unconjugated PSMA peptides in humans with advanced prostate cancer.

Example 12 below further demonstrates IRX-2's effectiveness in combination with PSMA exogenous antigen. Furthermore, IRX-2 was administered in combination with an irradiated PSMA expressing cell-based vaccine or a synthetic peptide conjugate vaccine and was able to enhance in vivo T cell immune responses to these antigens.

Example 13 below further demonstrates IRX-2's effectiveness in combination with peptides and Incomplete Fruend's adjuvant in enhancing in vivo T cell immune responses to these antigens. Results of the experiments show that IRX-2 can effectively be combined with multi-antigen cancer vaccines as well as cell-based vaccines.

Example 14 below further demonstrates IRX-2's effectiveness in combination with other adjuvants including CpG's, Poly I:C, IFN-γ and Incomplete Fruend's adjuvant. Furthermore, IRX-2, in combination with these other adjuvants, was able to enhance in vivo antigen specific T cell responses and the cytotoxic activity of antigen specific T cells. IRX-2, when included as part of a vaccine that included CpG's, Poly I:C, IFN-γ and Incomplete Fruend's adjuvant was effective when given as a single shot in enhancing antigen specific T cell responses.

Example 15 below further demonstrates IRX-2's effectiveness in enhancing B cell and T cell responses in combination with a viral-based vaccine. Furthermore, IRX-2 enhances B cell and T cell responses when used in combination with a viral-based vaccine that expresses the TRICOM triad of costimulatory molecules.

EXAMPLES

All steps relating to cell culture are performed under sterile conditions. General methods of cellular immunology not described herein are performed as described in general references for cellular immunology techniques such as Mishell and Shiigi (Selected Methods in Cellular Immunology, 1981) and are well known to those of skill in the art.

Example 1

Preparation of Primary Cell Derived Biologic (IRX-2)

The method of making the primary cell derived biologic is generally described in U.S. Provisional Patent Application No. 61/044,674. Mononuclear cells (MNCs) are purified to remove contaminating cells by loading leukocytes onto lymphocyte separation medium (LSM) and centrifuging the medium to obtain purified MNCs with an automated cell processing and washing system. The MNCs are then stored overnight in a FEP lymphocyte storage bag. An induction mixture of the MNCs is stimulated with a mitogen, preferably phytohemagglutinin (PHA), and ciprofloxacin in a disposable cell culture device and a primary cell derived biologic is produced from the MNCs. The mitogen is removed from the induction mixture by filtering and tangential flow filtration mode, and then the induction mixture is incubated. The induction mixture is clarified by filtering to obtain a primary cell derived biologic supernatant. Finally, the primary cell derived biologic supernatant is cleared from DNA and adventitious agents by applying anion exchange chromatography and 15 nanometer filtration and optionally further inactivation by ultraviolet-C (UVC). The final product can then be vialed and stored for future administration to a patient.

Example 2

Local perilymphatic injections in the neck with IRX-2 in addition to treatment with low dose CY (at 300 mg/m2), INDO (25 mg orally three times daily), and zinc (65 mg elemental zinc as the sulfate orally once a day) have induced clinical regressions in a high percentage of patients with squamous cell head and neck cancer (H&NSCC) (Hadden, 1994; Meneses, 1998; Barrera, 2000; Hadden, 2003; Menesis, 2003) with evidence of improved, recurrence-free survival. Overall, including minor responses (25%-50%), tumor shrinkage and reduction of tumor in pathological specimens, over 90% responded and the majority had greater than 50% tumor reduction.

These responses are speculated to be mediated by immune regression since both B and T lymphocytes were observed infiltrating the tumors. The therapy was not associated with significant toxicity. Treatment of lymphocytopenic cancer patients with the combination of IRX-2 has resulted in marked lymphocyte mobilization; where analyzed, these patients showed increases in CD45RA positive T cells (i.e., naïve T cells (see Table I below)). Further, intratumoral or peritumoral injection of IRX-2 in patients with H&NSCC resulted in either reversing immunotherapy-induced tumor regression or in progression of the tumor. The tumor is thus not the site of immunization. Rather, analysis of regional lymph nodes revealed that the regional lymph node is the site of immunization to postulated tumor antigens (Meneses, 2003; see FIGS. 1-5). None of these patients treated with IRX-2 developed metastasis which would have been expected in 15% of the patients clinically and up to 50% pathologically. These results indicate that systemic immunity rather than merely local immunity had been induced. Patients were pretested with a skin test to 0.1 ml of IRX-2 prior to treatment and more than 90% of those with a positive skin test (>0.3 mm at 24 hours) had robust clinical and pathological responses. Patients with negative skin tests had weak or no responses. Thus, skin testing selects good responders.

Major increases were observed in T lymphocyte counts (CD3) 752->1020 in these T lymphocytopenic patients (T cell counts 752 vs. 1600 (normal)). Importantly, there was a corresponding increase in "naïve" CD45RA positive T cells (532->782). As previously mentioned, these increases are generally not thought to occur in adults particularly with a pharmacological therapy like IRX-2. These cells presumably are recent thymic émigrés and could be considered a major new capacity for responding to new antigens like tumor antigens. The preexisting CD45RA positive cells were not responding to the tumor antigens and may have been incapable of doing so due to tumor-induced immune suppression (anergy).

TABLE I

Treatment of Lymphocytopenic Patients with H&NSCC with IRX-2 Increases in Naïve T Cells in Blood (#/mm)

| PATIENT # | NAÏVE T CELL MARKER | | | PAN T CELL MARKER | | |
|---|---|---|---|---|---|---|
| | PRE | POST | INCREASE | PRE | POST | INCREASE |
| 1 | 479 | 778 | +299 | 704 | 1171 | +467 |
| 2 | 938 | 1309 | +371 | 1364 | 1249 | −115 |
| 3 | 98 | 139 | +41 | 146 | 178 | +32 |
| 4 | 341 | 438 | +97 | 655 | 590 | −65 |
| 5 | 567 | 652 | +97 | 453 | 643 | +190 |
| 6 | 658 | 1058 | +400 | 1118 | 1714 | +569 |
| 7 | 642 | 1101 | +459 | 822 | 1601 | +779 |
| MEAN | 532 | 782 | +250 | 752 | 1020 | +269 |

The literature (Hadden J W, Int'l J Immunopharmacol 11/12:629-644, 1997; Hadden J W, Int'l J Immunopharmacol 21:79-101, 1999) indicates that for both SCC and adenocarcinomas, the two major types of cancer, regional lymph nodes reflect abnormalities related to the tumor, including sinus histiocytosis, lymphoid depletion and often the presence of tumor-associated lymphocytes capable of reacting to tumor cells (with IL-2). With metastasis, lymphoid depletion and depressed function occur. An unpublished analysis of uninvolved cervical lymph nodes in 10 H&NSCC patients showed reduction in average lymph node size and an increase in sinus histiocytosis associated with H&NSCC (see controls of FIGS. 1-4A and B of the present application).

Following treatment with one cycle of the IRX-2 protocol (Hadden, 1994; Meneses, 1998; Barrera, 2000), the uninvolved cervical lymph nodes showed the changes indicated in FIGS. 1-4. Compared to the regional lymph nodes of patients with H&NSCC not treated with IRX-2, these nodes showed a significant increase in size, T cell area and density, and decreases in sinus histiocytosis and congestion. The lymph nodes of treated patients were all stimulated and were larger than control nodes with increased T cell area and density. These nodes were thus not only restored to normal but showed evidence of T cell predominance, a known positive correlate with survival in H&NSCC (Hadden, 1997).

Figure 5:
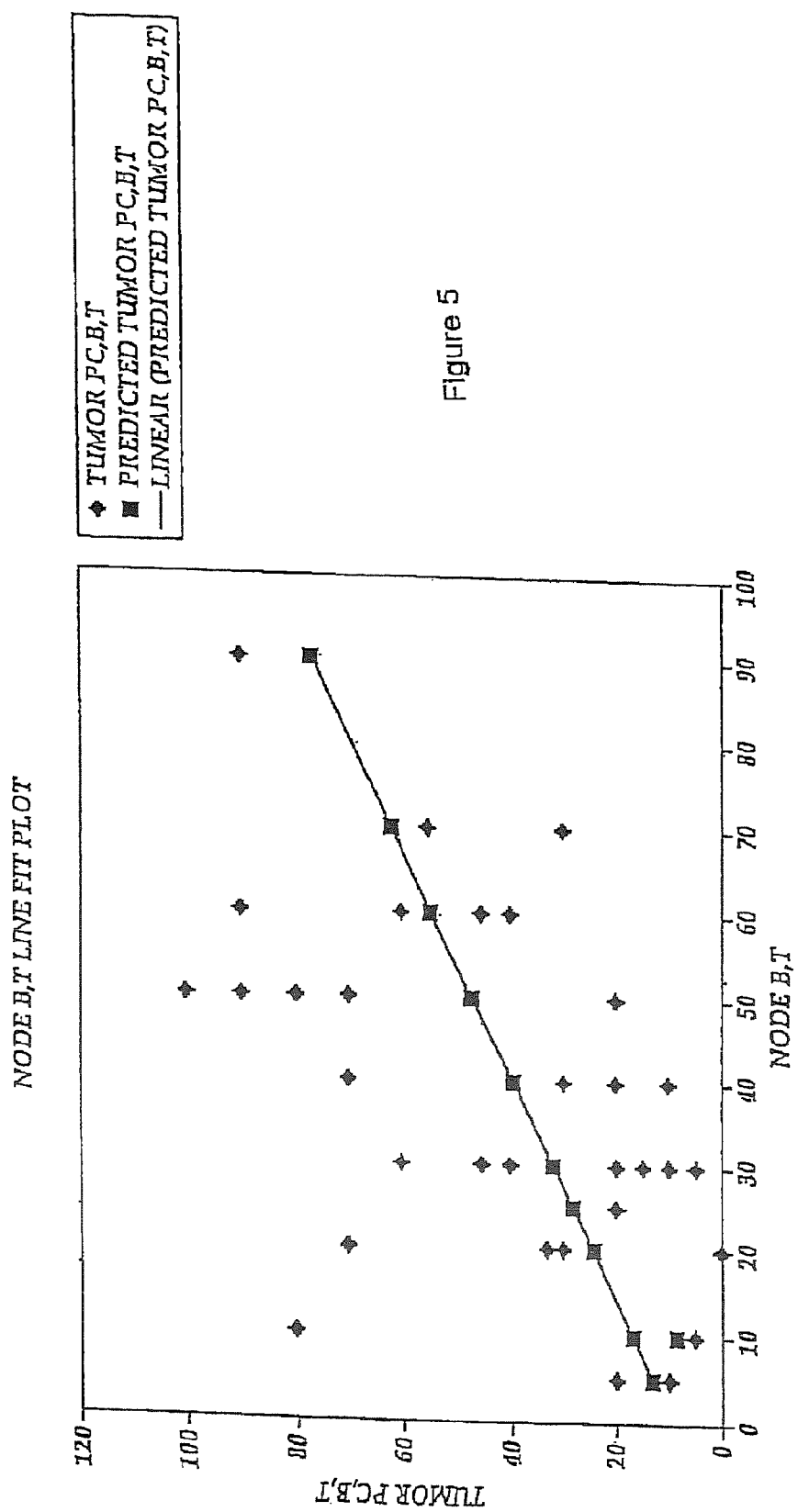
FIG. 5 is a graph showing a Node B&T (B cell and T cell) and Tumor B&T fit plot.

Importantly, when the lymph node changes related to B and T cell areas were correlated with the changes in their tumors reflecting T and B cell infiltration, a high degree of correlation was obtained for T cells (p.<0.01) and B cells (<0.01) and overall lymphoid presence (p.<0.001) (FIG. 5). In turn, these changes correlated with tumor reduction by pathological and clinical criteria. These findings indicate that the tumor reactions are directly and positively correlated with lymph node changes and that the tumor reaction reflects the lymph node changes as the dependent variable. These findings, taken in conjunction with knowledge about how the immune system works in general (Roitt, 1989), and following tumor transfection with a cytokine gene (Maass, 1995), indicate that the IRX-2 protocol immunizes these patients to endogenous tumor antigens at the level of the lymph nodes. No one has previously presented evidence for lymph node changes reflecting immunization with autologous tumor antigens. This confirms that the present invention can induce immunization with previously ineffective or poorly effective tumor antigens in an effect to yield regression of distant metastases.

Example 3

Figure 6:
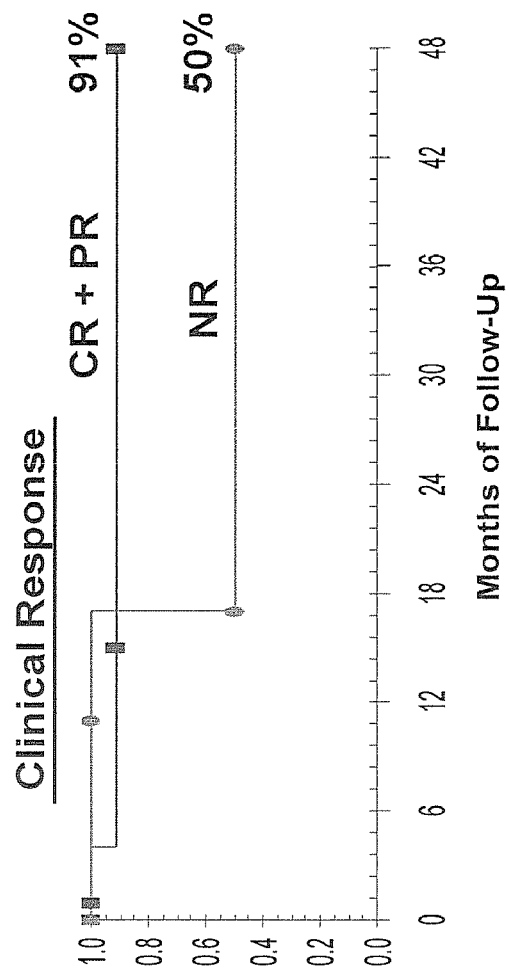
FIG. 6 is a graph illustrating the survival percentage of treated patients at forty-eight months.
Figure 7:
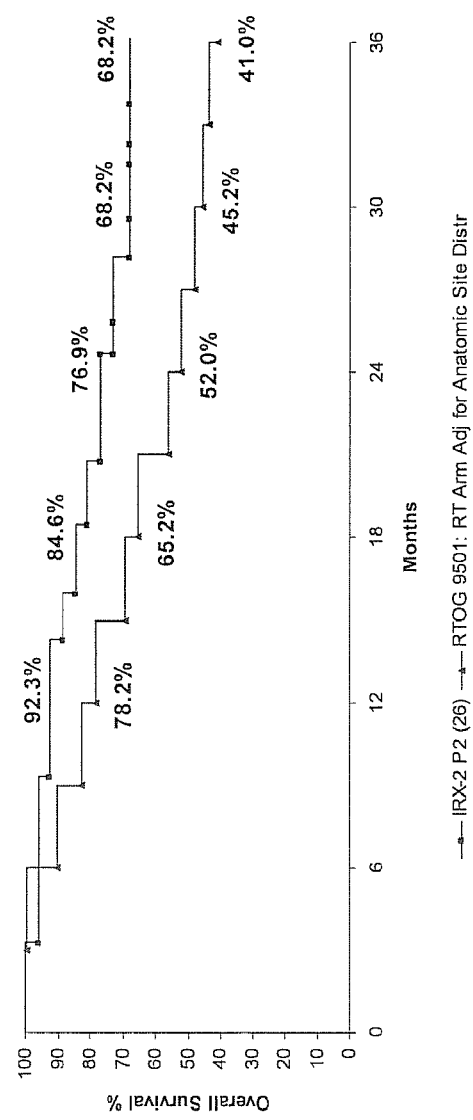
FIG. 7 is a graph illustrating the survival of complete and partial responders compared to minor and non-responders.
Figure 8:
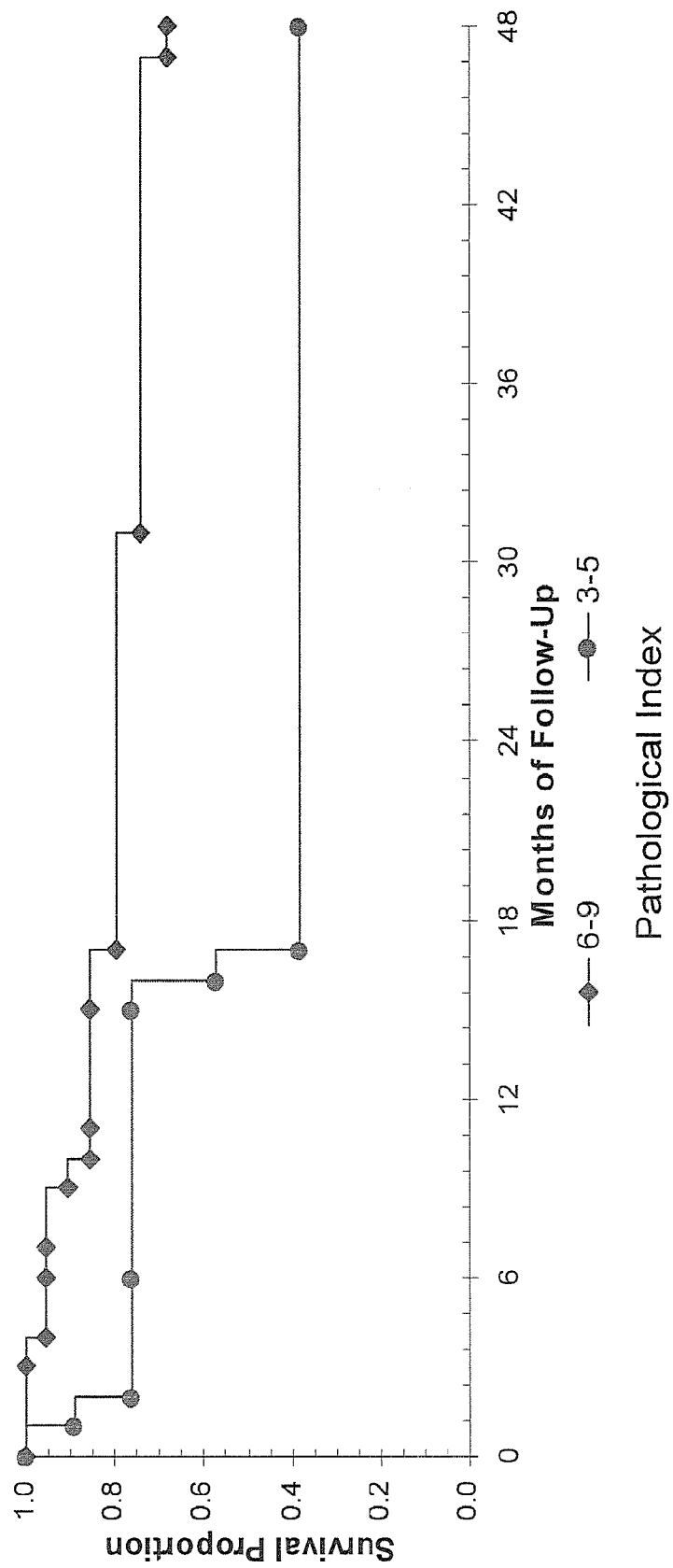
FIG. 8 is graph illustrating the relation of the pathology index to survival.
Figure 9:
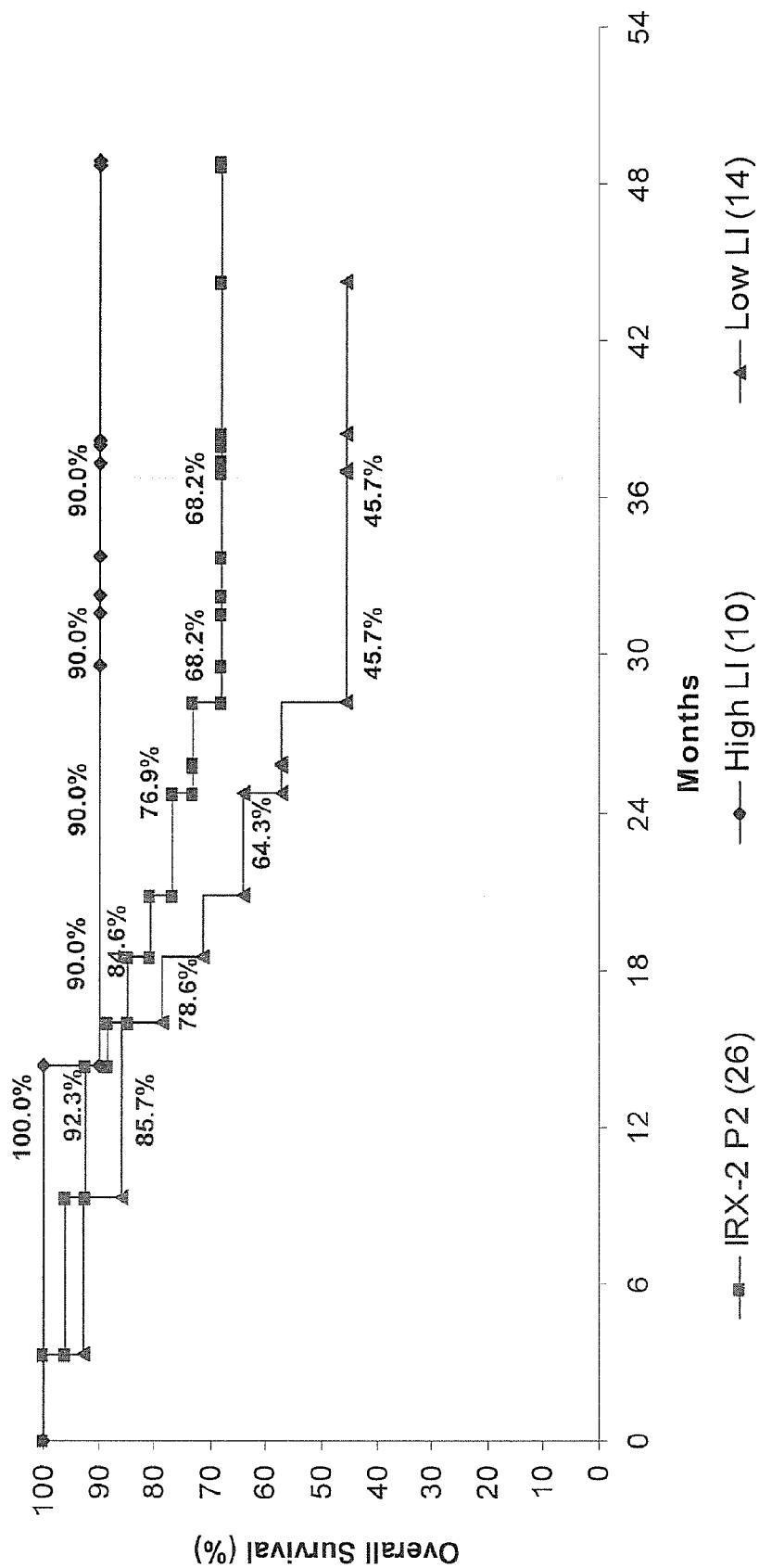
FIG. 9 is a graph showing the relationship of lymphocyte infiltration to survival.

Further analysis of the clinical, pathological and survival data of the aforementioned clinical trial study offer more insights into the nature of the invention as it relates to immunization of cancer patients to their own autologous tumor antigens and the resulting immune regression of their tumors. FIG. 6 shows that the treatment with the IRX-2 protocol is associated with increased survival at 48 months ($p<0.01$). FIG. 7 shows that positive clinical responses correlate with survival, i.e., patients with complete responses (CR) or partial responses (PR)(>50% tumor reduction) have a better survival than those with minor responses (MR) (<50%, but >25% tumor reduction) or no response (NR)(<25%)($p<0.01$). FIG. 8 shows that patients with stronger pathological responses (index of 6-9) have a better survival than those with weaker pathological responses (<6) ($p<0.02$). FIG. 9 shows that lymphoid infiltration into the tumor as a single variable predicts survival ($p<0.01$). Chi Square analysis of the relationship of clinical response to the pathological response shows a highly significant relationship ($p<0.01$) indicating that the two correlate with each other as well as to survival, thus providing a statistical triangulation of the data interrelating clinical responses, immune regression parameters, and survival. Such relationships have never been shown for immunotherapy of a human cancer.

Figure 10:
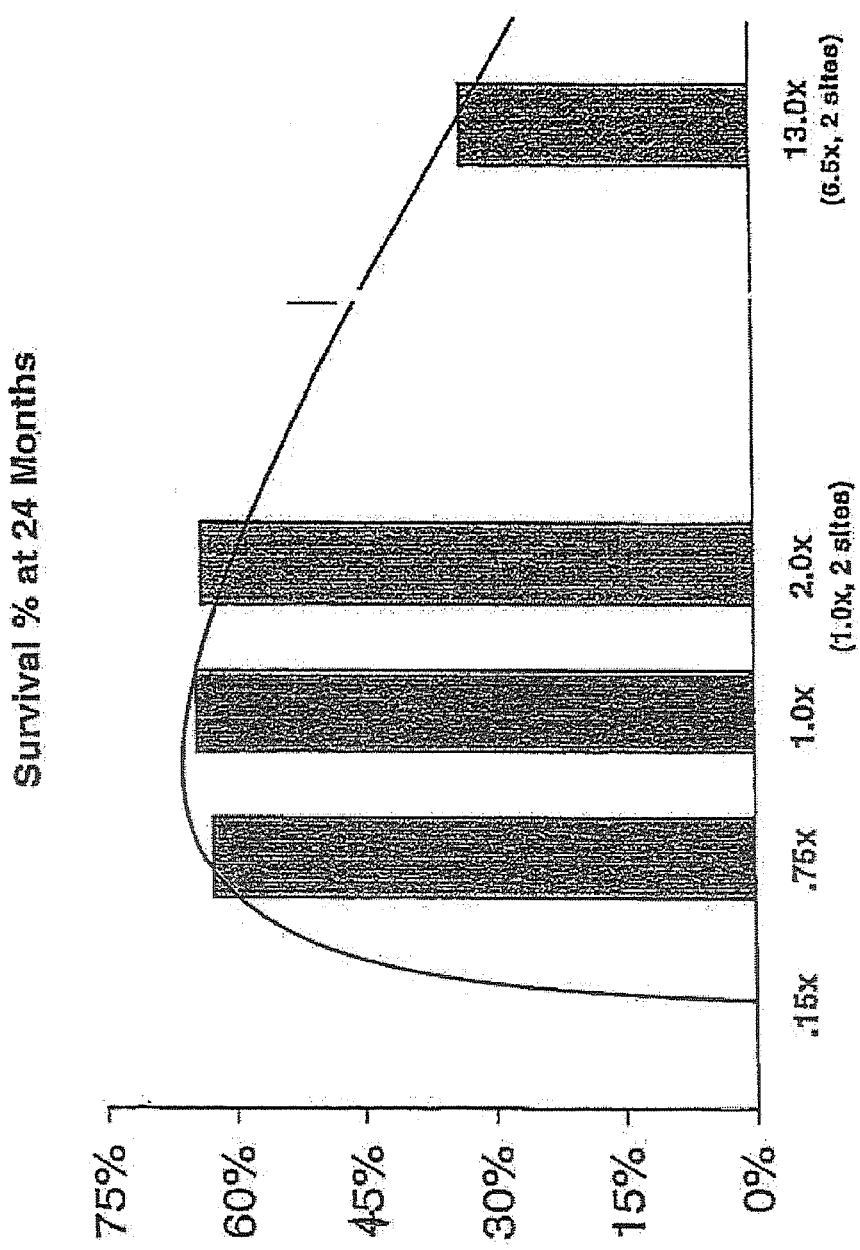
FIG. 10 is a graph illustrating the survival percentage (dose response) of treated patients at twenty-four months, wherein "x" is equal to about 100 IU/ml of IL-2.

Finally, FIG. 10 presents a dose response curve for the IRX-2 of the present invention, relating dose to overall survival at twenty-four months. IRX-2 treatment has an optimal impact on survival at about 100-233 international units of IL-2 equivalence.

Example 4

Two patients with lymphoma of the head and neck were treated according to the protocol as described above. The following scheme was followed.

Before treatment, the patients were skin-tested with IRX-2 at 0.1 ml injected subcutaneously in the forearm, the region was marked, and 24 hours later, the test was read. The test was considered positive if the induction and erythema was equal or larger than 3 mm.

Case 1:

The patient was a 23-year-old male who presented with a prior history of a three month presence of a tumor on the left submaxillary region, with no other symptoms. In the emergency room, he was found to have lymph adenopathy of the left submaxillary triangle of approximately 6.5 cm in diameter of a hard consistency, partially fixed at deep levels. The rest of the physical exam was normal. The incisional biopsy showed Hodgkin's lymphoma. The lesion was staged ECIIA. A one-cycle treatment of IRX-2 was given, obtaining a minor response, as the adenopathy reduced in size by 1 cm in diameter. The biopsy report obtained after IRX-2 treatment showed 60% of the lesion showed normal lymphocytic infiltration, and the rest of the neoplasia (40%) showed necrosis. No viable tumor cells were found.

Following this, the patient received radiation treatment in the neck of 3600 rads. The patient was free of disease at two years.

Case 2:

The patient is an 82-year-old male, who presented with a two-month history of a painful mid-neck tumor mass, as well as a 10 kg loss of weight. On physical exam, the patient presented with tumor on the right palatine tonsil, which was enlarged to approximately 4×3 cm, with an ulcer in the center of the tonsil. On the neck, a right submaxillary lymph node measured approximately 2×2 cm and a lymph node mass at level II and III of approximately 5×5 cm. The rest of the exam was normal. The incisional biopsy of the tonsil and one of the neck lymph nodes demonstrated defined non-Hodgkin's lymphoma mixed, of intermediate grade.

The patient was subjected to two cycles of IRX-2 at the end of which a 1 cm reduction in the diameter of the tonsil and neck adenopathy was observed. The pathological report post-IRX-2 treatment showed 20% live tumor, 30% tumor fragmentation and necrosis, and 50% normal lymphocyte infiltration.

The patient was given chemotherapy (CHOP) for 6 cycles and later external radiotherapy (RT) at a total dose of 4600 rads. He recurred at eight months post RT with adenomegaly at the occipital level. The patient died three months later with evidence of neck disease.

Example 5

Ten patients with untreated early stage cervical cancer, clinically staged IB1, IB2 and IIA, were treated with local perilymphatic injections of IRX-2 (10 daily injections) followed by radical hysterectomy at day 21. One day before starting the IRX-2 treatment, patients received a single IV dose of CY at 300 mg/m. Oral INDO or ibuprofen and zinc sulfate were administered from days 1 to 21. The clinical and pathological response, toxicity and disease-free survival were evaluated.

All patients completed IRX-2 treatment and were evaluated for response and toxicity. Clinical response was seen in 50% of patients (3 partial response (PR), 2 minor response (MR) (>25%<50% reduction)). Seven patients underwent surgery. Pathologically, tumor reduction associated with tumor fragmentation was found in five cases. There was a heterogeneous pattern of cell types infiltrating the tumor, which included lymphocytes, plasma cells, neutrophils, macrophages and eosinophils. Treatment was well-tolerated except for mild pain and minor bleeding during injection and gastric intolerance to INDO. At 24 months of follow-up, nine patients were disease-free.

This study shows that IRX-2 treatment induces immune-mediated tumor response in early stage untreated cervical carcinoma.

Example 6

Two patients with liver metastasis from primary hepatocellular carcinoma were treated with intrasplenic IRX-2 (1 or 3 injections). The protocol was as previously described for the H&NSCC, cervical, or lymphoma cases. One patient with advanced hepatocellular carcinoma had a partial response confirmed by tomography. The other had a partial response confirmed by surgery. Histological exam showed tumor reduction, fragmentation, and lymphoid infiltration.

Example 7

Four patients with squamous cell carcinoma of the penis (human papiloma virus associated) were treated with the IRX-2 protocol as described above; all four had partial responses clinically and the surgical specimens showed tumor reduction and fragmentation and lymphoid infiltration characteristic of the H&N SCC cancer patients.

Example 8

Correction by IRX-2 of T Lymphocytopenia

The objective of the following experiment was to assess the effect of a 10-daily injection treatment of IRX-2 containing the six cytokines of IL-1, IL-2, IL-6, IL-8, IFN-γ, and TNF-α (115 units IL-2 equivalence/day) on lymphocyte counts (LC) of lymphocytopenic patients. These patients had recovered from prior surgery and radiotherapy for head and neck cancer, and had persistent lymphocytopenia with mean counts of 441 cells/mm3. Normal levels of LC are 2000 cells/mm3. The patients were free of cancer at the time of treatment. LC were obtained at day 0 and day 13. T lymphocytes (CD3+) and T cell subsets (CD4+ or CD8+) were assessed by cytofluorometry. Table II presents the data for five responding patients. Significant increases were observed for LC, CD3+, and CD4+ T cells.

TABLE II

| Pt. Number | TLC* | CD3* | CD4* | CD8* |
|---|---|---|---|---|
| 1 | 100 | 83 | 28 | 40 |
| 2 | 136 | 62 | 52 | 55 |
| 3 | 100 | 63 | 24 | 3 |
| 4 | 100 | 74 | 331 | −20 |
| 5 | 100 | 166 | 173 | −16 |
| Mean ± SEM | 107 ± 7 | 90 ± 19 | 122 ± 59 | 12 ± 15 |

*Changes in number of cells per mm$^3$ from day 0 to day 13.

These changes compare favorably to those achieved by much higher doses of pegylated interleukin 2 ($3\times10^6$ units of recombinant IL-2) in lymphocytopenic AIDS patients (T. Merigan, personal communication) but with less toxicity. They are less than those achieved with 8-day infusions of $>10\times10^6$ units/day of IL-2 in AIDS patients; however, the latter required great expense, inconvenience, and had significant toxicity (Kovaks, 1997). These results with IRX-2 were obtained in the absence of INDO and CY and thus show that the effect of the regimen on LC is that of the IRX-2 composition of the invention.

Example 9

Figures 11A, 11B:
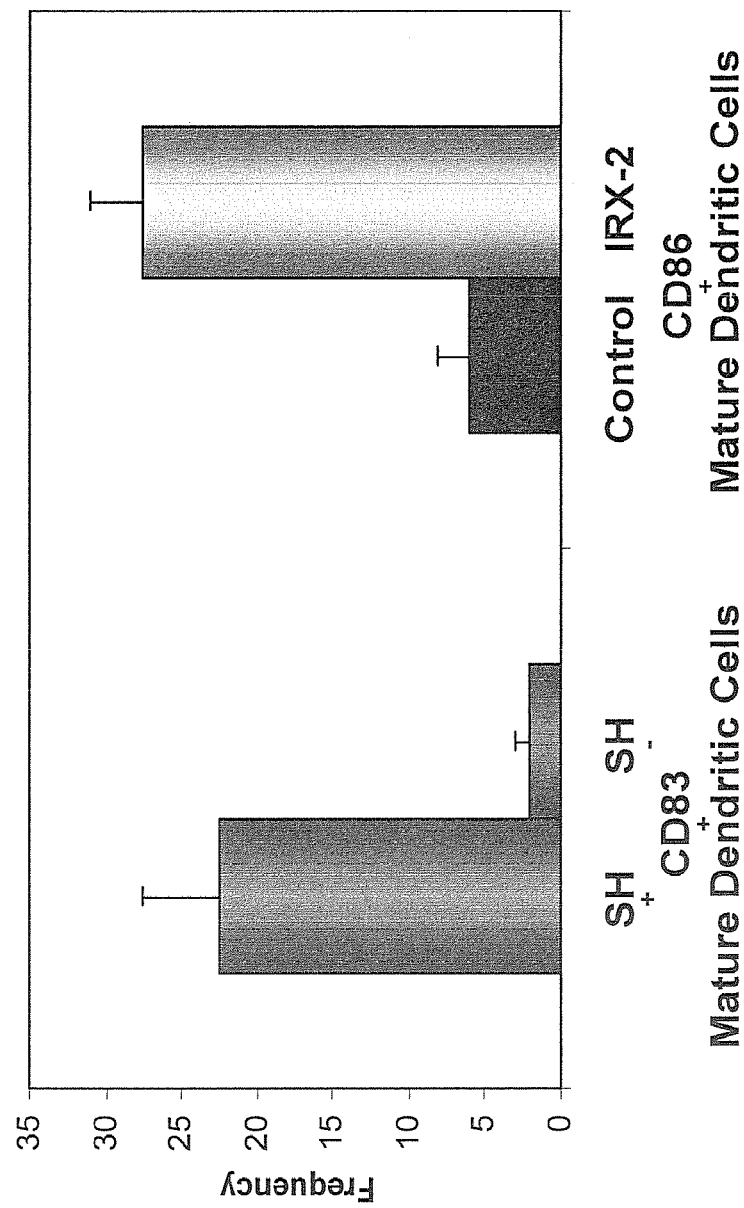
FIG. 11A is a bar graph illustrating the accumulation of partially mature CD83+ dendritic cells (DCs) in the lymph nodes of SH+ cancer patients.
FIG. 11B is a bar graph showing an increase in the number of CD86+ activated DCs upon treatment with IRX-2 (IRX-2)

IRX-2 Stimulates Dendritic Cell Maturation and Activation:

In previous experiments, lymph nodes from five IRX-2-treated H&NSCC patients and five untreated H&NSCC control patients were isolated and cellular constituents analyzed by flow cytometry using a panel of cell surface markers for dendritic cells (i.e., CD83+, CD86+, and CD68+). As noted above, sinus histiocytosis is a lymph node pathology seen in some cancer patients that is characterized by the accumulation in the lymph nodes of large histiocytes which represent immature dendritic cells. As demonstrated in FIG. 11A, patients with SH(SH+) have an accumulation of CD68+, CD83+, CD86− DCs in their lymph nodes, while those without noticeable SH have few CD83+ cells. However, IRX-2 treatment resulted in a five-times increase in the number of CD86+ (concomitant with CD68+, CD83+) DCs compared to non-treated cancer controls, indicating a conversion to an "activated" DC phenotype. Controls are untreated H&NSCC patients compared to IRX-2-treated cancer patients (see FIG. 11B).

Since sinus histiocytosis represents an accumulation of partially matured DCs presumed to be bearing endogenous tumor peptides, full maturation and activation with expression of the co-stimulatory receptor CD86 reflects use of the IRX-2 of the present invention to correct this defect on maturation and to allow effective antigen presentation to T cells. The IRX-2 of the present invention thus reverses sinus histiocytosis and leads to effective immunization of naïve T cells.

The data described above and subsequent data contained in Meneses et al. (2003) showed that the treatment of patients with H&NSCC using perilymphatic IRX-2, low dose CY, and INDO reversed the sinus histiocytosis frequently evident in the lymph nodes in this and other cancers. However, it was not apparent from this data which of the above agents, IRX-2, CY, and/or INDO, corrected this defect.

The following data present evidence that IRX-2 containing the six cytokines of IL-1, IL-2, IL-6, IL-8, IFN-γ, and TNF-α induces DC maturation and activation in the absence of CY and/or INDO. The IRX-2 used in these experiments contains the six cytokines listed above. For the purposes of these experiments, IRX-2 concentrations are expressed as the concentration of TNF-α contained in IRX-2. The cytokine concentration in IRX-2, including TNF-α, was measured by ELISA and the recombinant TNF-α purity is >95%. For all experiments, except titrations, IRX-2 was used at a concentration of 1 ng/ml.

The medium used was RPMI 1640, supplemented with 2 mM L-glutamine, 50 μg/ml streptomycin, 50 U/ml penicillin and 10% FBS (all reagents purchased from Cellgro, Herndon, Va.). GM-CSF, TNF-α and VEGF165 were purchased from Peprotech (Rocky Hill, N.J.). X-VIVO 10 was purchased from BioWhittaker (Walkersville, Md.). LPS was purchased from Sigma (St. Louis, Mo.). All reagents were tested for endotoxin contamination with the sensitive *Limulus amebocyte* lysate assay (LAL assay; BioWhittaker) according to the manufacturer's instructions and were found to be negative. All solutions were found to contain less than 0.06 EU/ml, the lowest detection limit. Additionally, all plastic ware was pyrogen-free.

PBMCs used in these experiments were obtained from 30 ml of leukocyte enriched buffy coat of healthy donors by centrifugation with Ficoll-Hypaque centrifugation (Cellgro, Herndon, Va.), and the light density fraction from the 42.5-50% interface was recovered. The cells were resuspended in culture medium and allowed to adhere to 6-well plates (Costar, Cambridge, Mass.). After 2 hours at 370 C, nonadherent cells were removed by washing and adherent cells (~90% CD14+ cells, i.e., monocytes) were cultured in 3 ml of medium supplemented with 50 ng/ml GM-CSF (500 U/ml) and 50 ng/ml IL-4 (500 U/ml).

For surface marker analysis, the following fluorochrome-conjugated mAbs (all from BD Pharmingen, San Diego, Calif.) were used: CD86-PE, CD80-FITC, CD54-APC, CD83-PE, HLA-DR-FITC, CD1a-APC, CD40-FITC and appropriate isotype controls. Immunophenotypic analysis was performed using FACS. Cells (0.25×106) were washed in PBS supplemented with 2% FBS and 0.1% NaN3 (FACS wash buffer) and incubated for 30 min at room temperature with APC-, PE-, or FITC-conjugated mAbs or with the corresponding isotype-matched mAb. Excess mAb was removed by washing in FACS wash buffer. Results were expressed as either mean fluorescence intensity or percentage of cells expressing the specified antigen. Fluorescence analysis was performed on a FACSCalibur flow cytometer (BD Biosciences, Rockville, Md.) after acquisition of 10,000 events and analyzed with BD Biosciences CellQuest software (Rockville, Md.).

Figure 12:
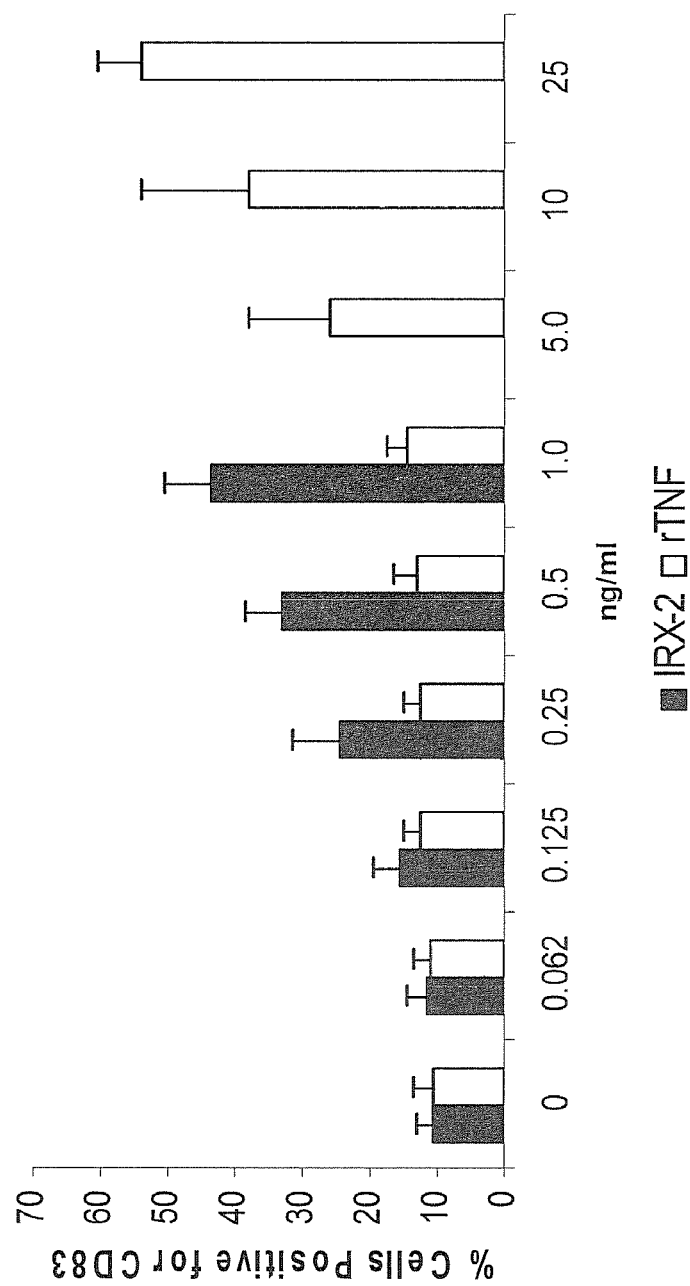
FIG. 12 is a graph showing that IRX-2 (IRX-2) induces DC maturation as detected by increased CD83 expression on DCs.

As demonstrated in FIG. 12, the IRX-2 composition of the invention increased the number of DCs bearing the CD83 antigen, a key marker of DC maturation. More specifically, adherent PBMCs were cultured for 7 days in the presence of GM-CSF and IL-4 as described above and then stimulated with increasing amounts of either recombinant TNF-$\alpha$ (PeproTech) or IRX-2. After 48 hrs, the cells were washed and analyzed for CD83 expression by flow cytometry. FIG. 12 indicates that IRX-2 is active at inducing DC maturation, as evidenced by an increase in CD83+ cells. Moreover, IRX-2 was more active at inducing DC maturation than an equivalent dose of TNF-$\alpha$ alone. The data in FIG. 12 are represented as the mean of 5 individual experiments −/+SEM ($p<0.0001$, by ANOVA).

These data indicate that IRX-2 promotes the maturation of DCs and does so in a way that cannot be accounted for by any single cytokine contained in the IRX-2 mixture that is known to act on DC maturation. For example, normal in vitro differentiation of PBMCs requires the presence of 100-500 U/ml GM-CSF (approximately 10-50 ng/ml) and 500-1000 U/ml IL-4 (50-100 ng/ml). This generates a population of cells committed to the DC lineage but in a relatively immature state (low/moderate CD86, CD40, HLA-DR expression, null for CD83). Undiluted IRX-2 has undetectable quantities of IL-4 and contains 10 to 50-fold lower concentrations of GM-CSF (approximately 1.1 ng/ml) than is required for in vitro differentiation of DCs. Thus, the individual IL-4 and GM-CSF cytokines in the IRX-2 cannot account for the CD83+ cells produced in the cultures of FIG. 12.

TNF-$\alpha$ can induce such cells but at concentrations well above those contained in the IRX-2 of the invention (see FIG. 12). For example, after initial commitment to the dendritic cell lineage (by several days of GM-CSF+IL-4 in vitro), subsequent addition of a "danger signal" such as that derived from a pathogen (e.g., LPS) induces a fully mature dendritic cell phenotype including high/strong expression of CD86, CD40, HLA-DR, and the presence of CD83. TNF-$\alpha$ in the range of 20-50 ng/ml can largely mimic such a pathogen-derived danger signal resulting in upregulation of the same markers. However, the undiluted IRX-2 mixture has only 2.8 ng/ml of TNF-$\alpha$ on average, far below the TNF-$\alpha$ concentrations required for full DC maturation. Thus, the results depicted in FIG. 12 clearly demonstrate that, at the TNF-$\alpha$ equivalent concentrations used in this experiment, the induction of the CD83 marker by IRX-2 could not be due solely to the presence of the TNF-$\alpha$ in the IRX-2 mixture.

Figure 13A:
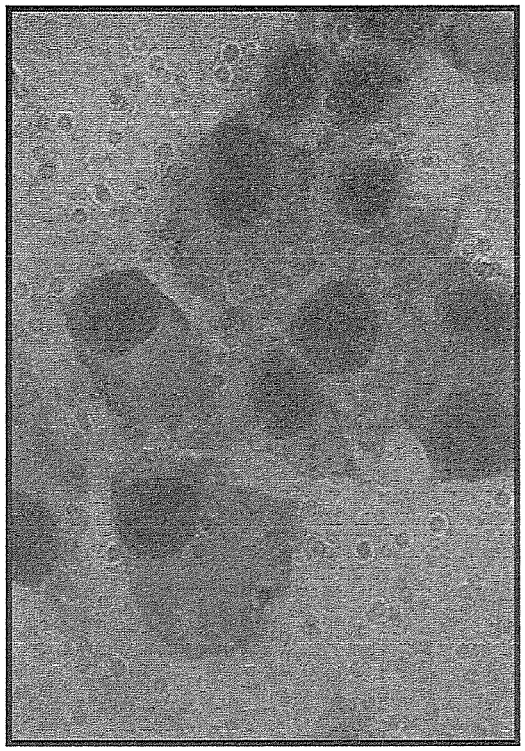
FIGS. 13A-B depicts the effect of IRX-2 on the morphology of monocyte-derived DCs in cytospin preparations. The cells treated with IRX-2 (FIG. 13B) exhibited the morphological characteristics of mature DCs such as cellular projections and large irregular shaped nuclei.
Figure 13B:

Since it is known that DCs undergo distinct morphological changes as they progress from immature to mature cells, immature DCs were treated with IRX-2 to determine if IRX-2 treatment changed the morphology of the cells. More specifically, adherent PBMCs were grown in the presence of GM-CSF (500 U/ml) and IL-4 (500 U/ml) for 4 days as described above (which treatment is known to yield immature DCs) and then were either treated with IRX-2 or left untreated as controls. After 3 days, the cells were visualized by Wright staining and microscopy. As shown in FIG. 13, the cells treated with IRX-2 (FIG. 13B) exhibited the characteristic cellular projections and motility of mature DCs, and continually extended and retracted their cellular processes and veils. These cells had large irregular shaped nuclei, numerous vesicles, relatively few cytoplasmic granules, and noticeable and abundant cellular projections as compared to the untreated controls (FIG. 13A). Thus, IRX-2 treatment resulted in DCs that possessed typical mature DC morphology.

In addition, it is known that the prototypical transition from immature to mature DCs results in well characterized increases and decreases in certain cell surface antigens. For example, immature DCs express high levels of CD1a, and upon encounter with stimuli such as cytokines or bacterial products, this marker is down-regulated. Thus, to determine if IRX-2 treatment resulted in the gain or loss of cell surface markers associated with the activation and maturation of DCs, GM-CSF and IL-4-treated adherent PBMCs (monocytes) (as described above) were grown for 7 days and then incubated for 48 hrs with or without IRX-2. Expression of CD1a, HLA-DR, CD86, CD40 and CD54 was examined by flow cytometry and expressed as mean fluorescence intensity.

Figure 14:
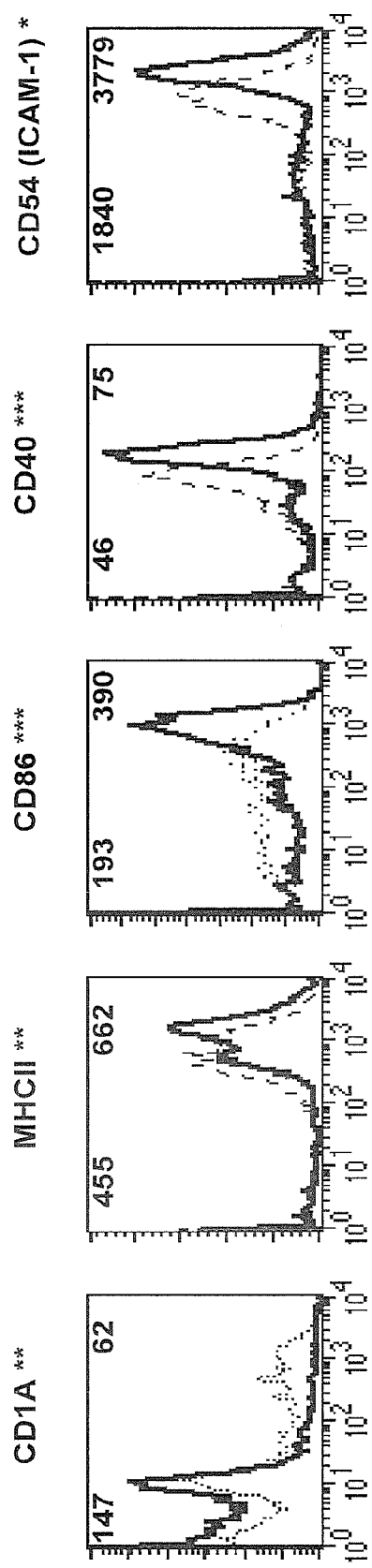
FIG. 14 contains histograms showing down-regulation of CD1a antigen and up-regulation of MHCII, CD86, CD40, and CD54 (ICAM-1) antigen expression by peripheral blood mononuclear cells (PBMCs) incubated with IRX-2 (IRX-2). These changes indicate that IRX-2 stimulates the maturation of DCs.

As demonstrated by the histograms of FIG. 14, IRX-2 treatment of immature DCs (indicated by solid lines in the histograms) resulted in the down-regulation of CD1a expression (147 vs. 62) as well as the up-regulation of MHCII expression (455 vs. 662). In addition, IRX-2 treatment led to an increase in cell size and a decrease in granularity (data not shown). Untreated controls are indicated by dashed lines in each histogram. The mean values for untreated DCs are shown in the left upper corner of the panels; the respective values for DCs treated with IRX-2 are shown in the upper right corner. Histograms shown are from a representative experiment and the values represent mean results from at least 10 individual experiments (*=$p<0.05$, =$p<0.002$, *=$p<0.00005$, paired Students t-test). As further indicated by FIG. 14, IRX-2 treatment enhanced the expression of co-stimulatory surface molecules CD86 (also known as B7-2) (193 vs. 390), CD40 (46 vs. 75), and CD54 (also known as intercellular adhesion molecule 1 or ICAM-1) (1840 vs. 3779). All of these changes in surface marker expression indicate that the IRX-2 of the invention is a potent effector of DC activation.

Consistent with their role as antigen-presenting cells, immature DCs have a high endocytic activity and actively take up antigens. Upon maturation, this activity is down-regulated, whereupon the DC is engaged in antigen processing and presentation. Under physiological conditions, the down-regulation of APC endocytosis is associated with an increase in peptide/MHC complexes on the surface leading to enhanced stimulation of T cells. To test the influence of IRX-2 on endocytosis, DCs were incubated with increasing amounts of IRX-2 and the ability to internalize FITC-dextran was determined. More specifically, adherent PBMCs (monocytes) were treated with GM-CSF and IL-4 (as described above) for four days and then stimulated with TNF-$\alpha$ (at 1 µg/ml) or with increasing concentrations of IRX-2 (IRX-2) up to the equivalent of 1 ng/ml TNF-$\alpha$. After 18 hrs, the cells were incubated with FITC-Dextran (Sigma, St. Louis, Mo.), which was added to a final concentration of 1 mg/ml. The cells were cultured for 30 min at 370 C. After incubation, the cells were washed four times with ice-cold PBS and analyzed by flow cytometry as described above.

Figure 15:
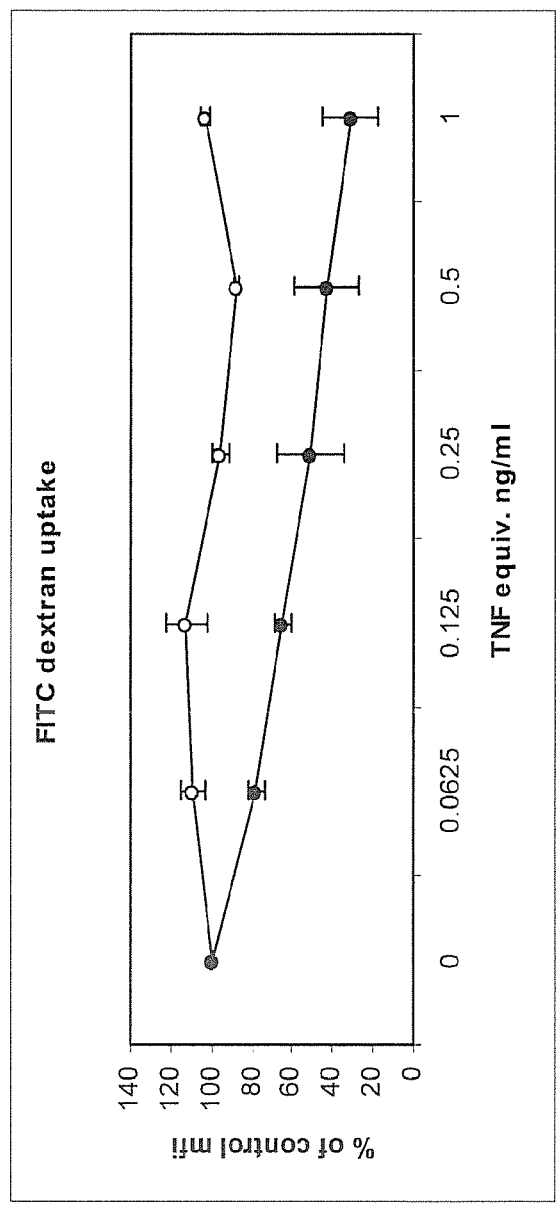
FIG. 15 is a graph showing that IRX-2 (IRX-2) reduces the endocytic activity of immature DCs, which reduced activity is indicative of DC maturation.

As shown in FIG. 15, immature DCs incubated with IRX-2 (closed circles) down-regulated endocytosis in a dose-dependent manner. TNF-$\alpha$ treatment (open circles) at the corresponding dose found in the IRX-2 had minimal effects. Treatment of immature DCs with higher amounts of TNF-$\alpha$ (10-25 ng/ml) did result in the down-regulation of endocytic activity as expected (data not shown). The data of FIG. 15 are shown as the percentage of mean fluorescence intensity of the stimulated versus the unstimulated DCs and are the mean of 4 independent experiments −/+SEM (p<0.00001, by ANOVA). These experiments indicate that the IRX-2 of the invention down-regulates the endocytic activity of DCs, an indication of DC maturation.

Next, the ability of IRX-2 to enhance the T cell stimulatory capacity of DCs was evaluated. Activated, mature DCs are potent stimulators of naïve T cells. In order to show that IRX-2 treatment was translated into functional effects as well as the phenotypic and morphologic changes noted above, the influence of IRX-2 on the T cell stimulatory capacity of DCs was assessed in a mixed lymphocyte reaction (MLR) proliferation assay.

More specifically, adherent PBMCs (monocytes) were first treated with GM-CSF and IL-4 (as described above) for seven days and then stimulated with or without IRX-2. After 48 hrs, the IRX-2-treated or untreated DCs were collected and assayed in an MLR as follows: purified DCs were co-cultured with $1 \times 10^5$ T cells from an unrelated donor at ratios of 1:5, 1:10, 1:30, and 1:100 DC: T cells. Allogeneic T-cells were prepared by running PBMCs purified from buffy coats by Ficoll-Hypaque gradient centrifugation over a nylon wool column. The assays were performed in triplicate in round-bottom 96-well plates. No IRX-2 was present during the MLR assay. After 5 days of DC-T cell co-culture, the wells were pulsed for 18 hours with BrDU. BrDU incorporation was measured using a colorimetric BrDU incorporation assay (Roche Diagnostics, Indianapolis, Ind.).

Figure 16:
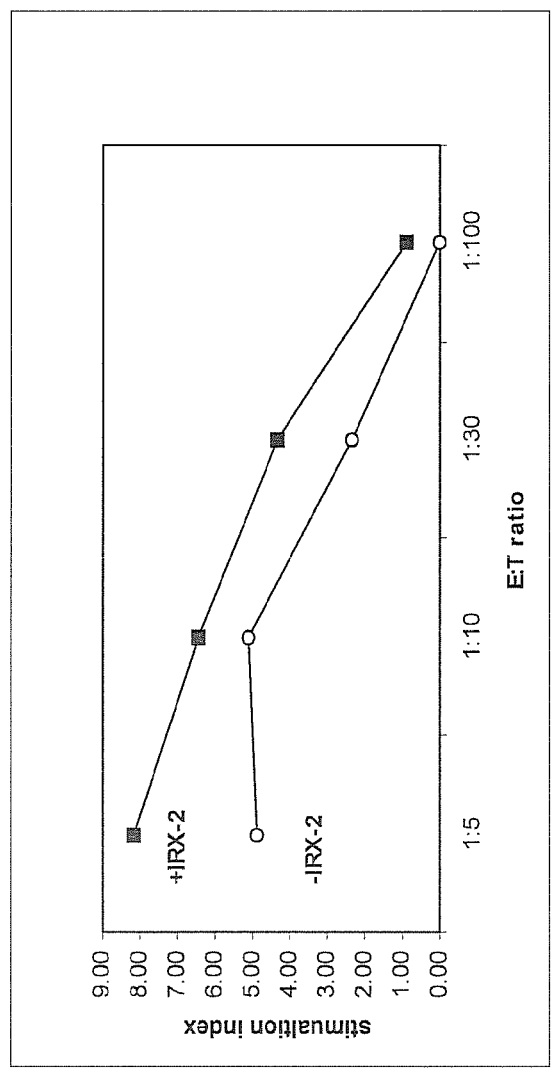
FIG. 16 is a graph showing that IRX-2 (IRX-2) enhances the T cell stimulatory capacity of DCs, which enhancement is indicative of DC maturation and activation.

As shown in FIG. 16, DCs exposed to IRX-2 (closed squares) two days before co-culture were more potent in inducing a T cell proliferation response than untreated DCs (open circles), confirming that IRX-2-treated DCs are functionally competent. The data in FIG. 16 are expressed as stimulation index which is defined as ((o.d. DC stimulated T cell−o.d. DC alone)/o.d. resting T cell)−/+SEM and are the mean result of 4 individual experiments (p<0.05, by ANOVA).

It is important to note that there was no IRX-2 in the co-cultures and the observed increase in T cell stimulation was due to the stimulatory effects of IRX-2 on DCs, rather than a direct effect of the IRX-2 on T cells. Thus, the IRX-2 of the invention enhances the T cell stimulatory activity of DCs as shown by enhanced proliferation in allogenic MLR reactions. Moreover, IRX-2 was shown above to increase the expression of ICAM-1 (CD54). This cell surface accessory ligand has been shown to be involved in signaling through LFA-1 and results in a bias towards a Th1 phenotype (Rogers, 2000). In a cancer setting, the functional consequence of these effects is that IRX-2-treated DCs would polarize the T cell response towards a Th1 phenotype and favor the activation of tumor-specific CTL activity, thus promoting tumor rejection.

Our data also demonstrate that IRX-2 stimulates the production of IL-12 from DCs. IL-12 is a potent Th1 polarizing cytokine secreted by DCs in response to pathogens during infection. However, one of the most important roles of DCs in mediating tumor rejection is to effectively and efficiently stimulate Th1-biased anti-tumor T cell responses and one of the critical cytokines in directing this response is IL-12. IL-12 is produced by activated DCs and is an essential factor involved in the differentiation of naïve CD4+ helper T cells into Th1 cells. Th1 cells secrete IFN-γ and IL-2 and these cytokines along with IL-12 mediate the activation and proliferation of cellular and phagocytic components of the immune system, such as CD8+ cytotoxic T lymphocytes (CTL).

To determine whether IRX-2 can induce IL-12 production in DCs, GM-CSF/IL-4 cultured monocytes were stimulated with IRX-2 for 18 hours and assayed for intracellular IL-12 p70 production. More specifically, adherent PBMCs were grown for 4 days in GM-CSF and IL-4 (as described above) and then treated with or without IRX-2 or LPS for 18 hours. Brefeldin A (BFA; 10 µg/ml; Sigma, St. Louis, Mo.) was added during the last 4 hours to accumulate most of the cytokine in the Golgi complex. Cells were fixed and permeabilized using Fix and Perm (Caltag, Burlingame, Calif.), according to the manufacturer's instructions, and were then labeled with FITC-labeled mAb against IL-12 p70 (BD Pharmingen, San Diego, Calif.) or the appropriate isotype control (BD Pharmingen, San Diego, Calif.). Cells were analyzed by flow cytometry.

Figure 17A:
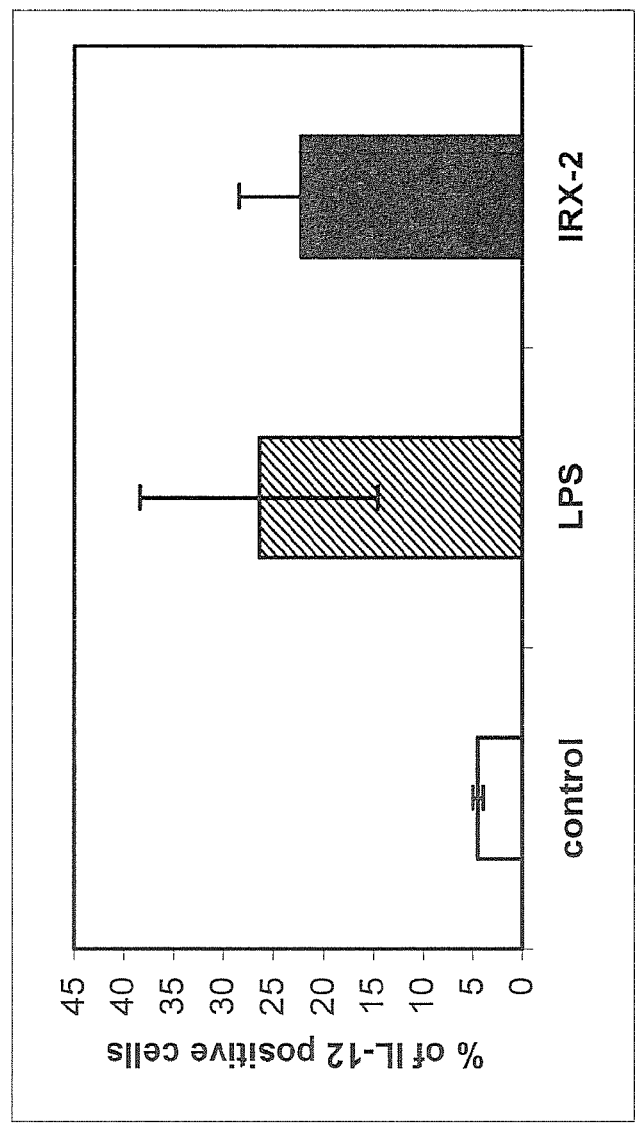
FIG. 17A is a bar graph showing that IRX-2 (IRX-2) increases the number of DCs producing IL-12 intracellularly. IL-12 is a cytokine produced by mature activated DCs.
Figure 17B:
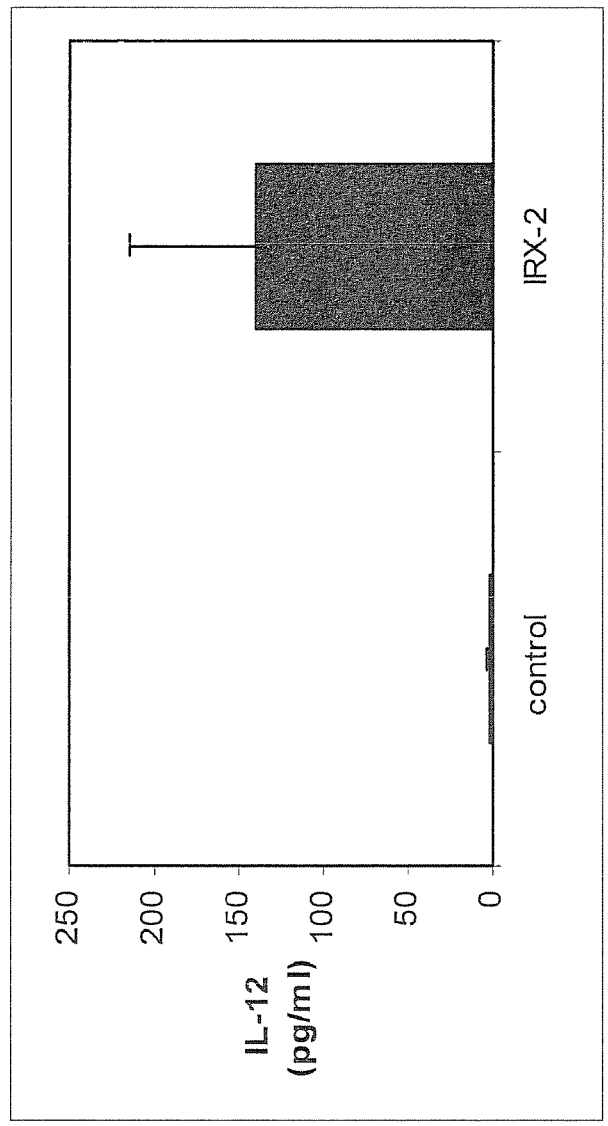
FIG. 17B is a bar graph showing that IRX-2 (IRX-2) increases the total amount of bioactive IL-12 secreted by DCs.
Figure 48:
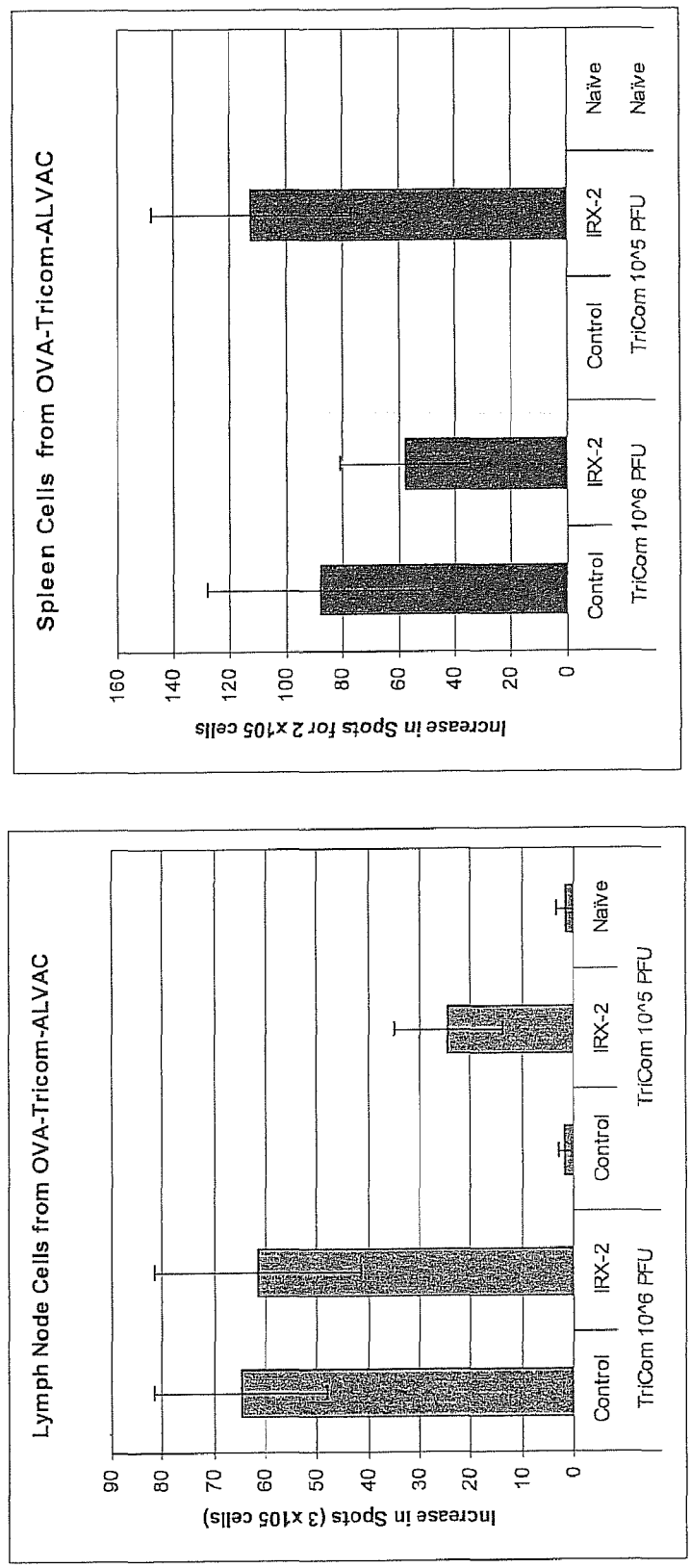
FIG. 48 is a graph of IFN-γ responses of T cells after vaccination with a viral-based vaccine that expresses TRI-COM and IRX-2.

As shown in FIG. 17A, IRX-2 increased the percentage of DCs producing IL-12 from 4.5% positive to 22.5% on average. LPS, a stimulator of IL-12 production in DCs, was used as a positive control and gave similar levels of induction relative to IRX-2 (27%±11). The data of FIG. 17A are the mean of 4 independent experiments and are expressed as the percentage of cells staining positively for IL-12−/+SEM (p<0.05 Students t-test). To confirm that the increased intracellular production of IL-12 corresponded to increased secretion of bioactive IL-12, the concentration of bioactive IL-12 in the supernatant of IRX-2-treated DCs (cultured initially for 4 days with GM-CSF and IL-4 as described above and incubated with IRX-2 for 48 hrs) was measured using a commercial ELISA kit (R&D Systems, Minneapolis, Minn.) that detects the bioactive p70 heterodimer. Thus, as shown in FIG. 17B, 48 hours after exposure to IRX-2, DC supernatants contained significantly more bioactive IL-12 than control-treated DCs. The data of FIG. 17B are the mean (−/+SEM) of 6 independent experiments (p<0.05, Students t-test).

Finally, our data indicated that IRX-2 reduces VEGF-induced apoptosis in DCs. VEGF is an inhibitor of DC maturation and has been shown to increase apoptosis levels in maturing DCs. To determine if IRX-2 was able to mitigate the effects of VEGF, DCs were treated with VEGF with or without IRX-2 and the level of apoptosis was determined by Annexin-FITC V binding. More specifically, adherent PBMCs were treated with GM-CSF and IL-4 for 7 days and then incubated in the presence or absence of VEGF (100 ng/ml) with or without IRX-2 (1:3) for 2 additional days. The cells were harvested and washed 2 times in ice-cold PBS and resuspended in Annexin binding buffer (BD Pharmingen, San Diego, Calif.). Annexin-V FITC (BD Pharmingen, San Diego, Calif.) and propidium iodide was added and the cells were incubated at 4° C. for 30 minutes. Cells were analyzed by flow cytometry.

Figure 18:
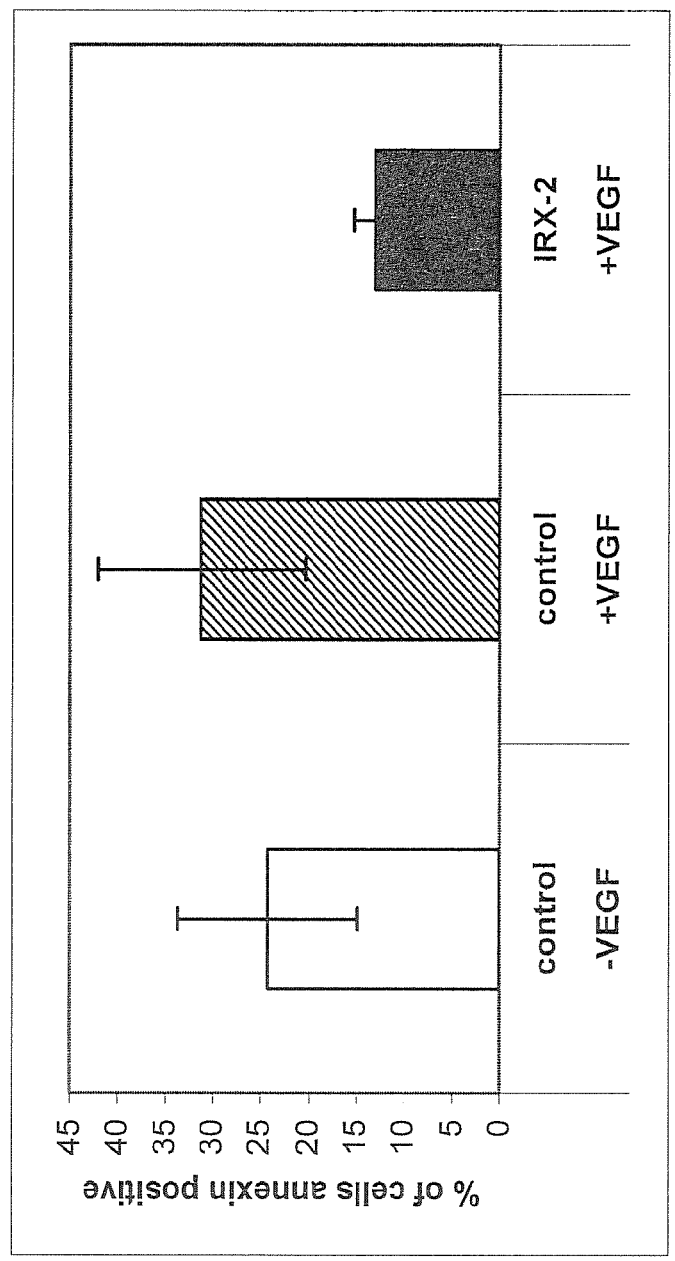
FIG. 18 is a bar graph showing that IRX-2 (IRX-2) decreases VEGF-mediated apoptosis in DCs, indicating a protective effect of IRX-2 on DC survival.

As shown in FIG. 18, apoptosis levels increased in VEGF-treated cells as compared to controls; however, IRX-2 reduced the level of apoptosis in VEGF-treated cells. The data of FIG. 18 are the result of 4 independent experiments and is expressed as the percentage of cells staining positively for Annexin V-FITC (−/+SEM). The data suggest that, in addition to its stimulatory capacity, IRX-2 also has a protective effect on mature DCs. Moreover, defective DC function and number may be mediated in part by aberrant VEGF expression by the tumor (Gabrilovich, 1996b; Saito, 1999; Takahashi, 2004). VEGF production by tumors was shown to be a predictor for poor prognosis in several cancers including H&NSCC, lung cancer, gastric cancer, and osteosarcoma (Gallo, 2001; Kaya, 2000; Miyake, 1992; Saito, 1998; Smith, 2000). The data contained herein indicate that IRX-2 can reverse VEGF-mediated apoptosis of DCs, thus promoting the survival of mature DCs within a tumor environment and allowing for prolonged antigen presentation and activation of tumor antigen-specific cytotoxic T lymphocytes.

Previous studies with DCs have employed natural cytokine mixtures such as monocyte-conditioned media (MCM) or mixtures of recombinant inflammatory cytokines containing TNF-α, IL-1β, IL-6, and PGE2 to mature DCs for use in ex vivo generated DC-based cancer vaccines (Romani, 1996; Bender, 1996; Sorg, 2003). A critical difference between IRX-2 and the cytokine mixtures used in other studies is that the level of cytokines used in this study were 10-100 fold lower, suggesting a significant synergism between the unique cytokine components of IRX-2. In addition, there are significant problems involved in the use of DCs matured by these other mixtures. For example, DCs matured in the presence of TNF-α, IL-1β, IL-6, and PGE2 have low or absent production of IL-12 and if improperly activated, may be tolerogenic (Steinman, 2002; Langenkamp, 2000). Additionally, there is a concern that fully mature DCs generated ex vivo might be "exhausted" and unable to efficiently prime an effective T cell response (Kalinski, 2001). The low levels of clinical responses seen in patients treated with DCs matured by the ex vivo method lends support to these concerns (Holtl, 2002; Schuler-Thurner, 2002; Thurner, 1999).

The evidence presented herein confirms that IRX-2 is a potent activator of dendritic cells. This data combined with the known effects of IRX-2 on T cells (Hadden, 1995b) suggests that IRX-2 is able to overcome the APC and T cell defects found in cancer patients and provides a mechanistic explanation for the successful clinical outcomes seen in Applicant's clinical trials. While DCs are now recognized as central players in cancer-directed immunotherapy, it is becoming increasingly clear that manipulating single elements of the immune system individually, e.g., tumor-specific T cell vaccination strategies or reintroduction of tumor-antigen pulsed DCs alone, is failing to produce significant clinical improvements for patients (Ridgway, 2003; Rosenberg, 2004). A more beneficial treatment plan may be to enhance the activities of several coordinating cell types concomitantly, e.g., T cells and DCs, allowing reinforcing interactions and a better likelihood that functional cascades are perpetuated rather than blocked by the tumor's various immunosuppressive strategies. In this setting, the IRX-2 of the invention may be acting to stimulate both endogenous DCs loaded with tumor antigen and tumor antigen-specific cytotoxic T cells, resulting in an effective immune response and tumor rejection. Taken together, these results indicate that the cytokine composition of the present invention can be a powerful clinical tool for eliciting an immune response against endogenous tumor antigens or could be used in conjunction with exogenously added tumor antigens in a cancer vaccine setting.

Example 10

IRX-2 Stimulates Monocyte/Macrophage Activation

Figure 19A:
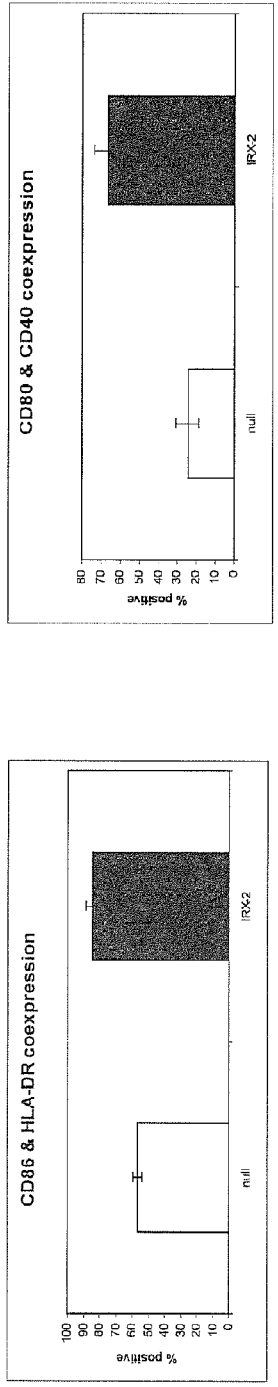
FIG. 19A contains two bar graphs depicting the increase in percentage of monocytes/macrophages staining positive for the combination of activation markers, CD86, HLA-DR, CD80 and CD40, after treatment of adherent PBMCs with IRX-2, as determined by flow cytometry.
Figure 19B:
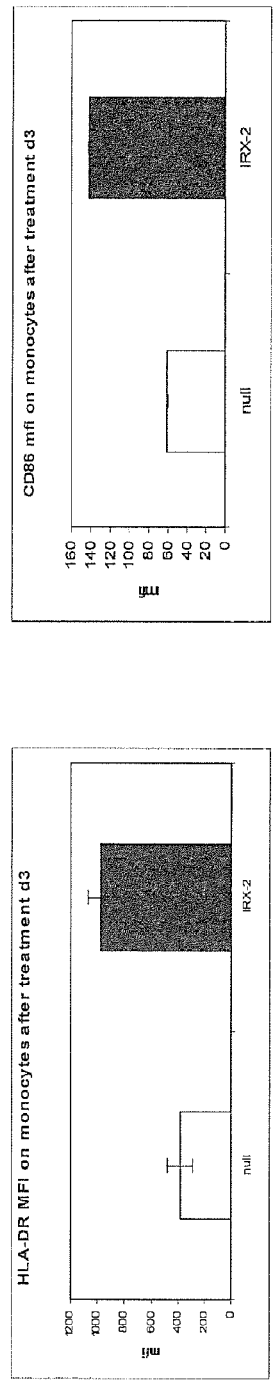
FIG. 19B is a series of bar graphs depicting the increase in mean fluorescence intensity (MFI) for the activation markers, CD86, HLA-DR, CD80 and CD40, after treatment of adherent PBMCs with IRX-2, as determined by flow cytometry.
Figure 19C:
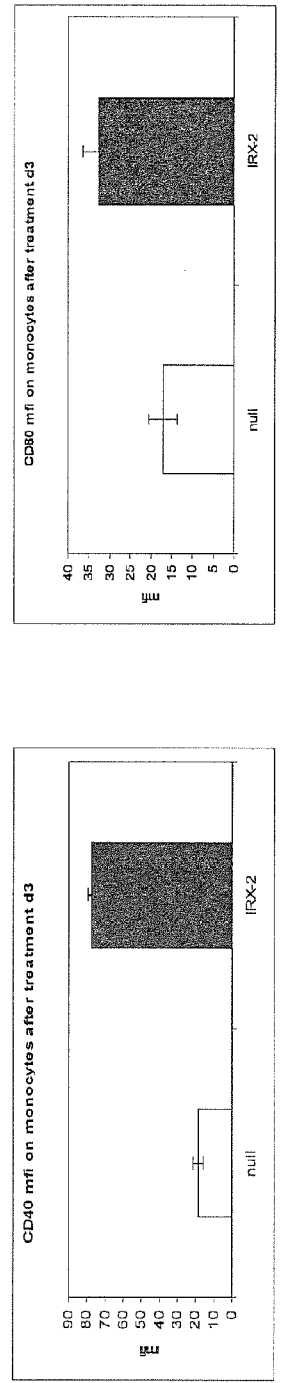
FIG. 19C shows two bar graphs showing the effect of IRX-2 on CD40 and CD 80 from monocytes/macrophages.

The IRX-2 of the invention containing the cytokines IL-1, IL-2, IL-6, IL-8, IFN-γ, and TNF-α is also a potent activator of monocytes/macrophages. More specifically, adherent PBMCs (~90% monocytes) were grown overnight in X-VIVO 10 media (BioWhittaker Bioproducts), stimulated for 24 hr with IRX-2 (at a 1:3 final concentration) and assayed for the expression of various activation markers typically found on activated macrophages by flow cytometry. As a control, cells were incubated for 24 hr in media lacking IRX-2. As demonstrated in FIG. 19, the treatment of the cells with IRX-2 versus no added cytokines produced a statistical increase in the percentage of cells staining positively (FIG. 19A) and an increase in mean fluorescence index (MFI) (FIG. 19B) for HLA-CR, CD86, CD40 and CD80, all activation markers of monocytes/macrophages (p<0.03). The data shown in FIG. 19 represent the mean value+/−SEM from three independent experiments/donors.

Figure 20:
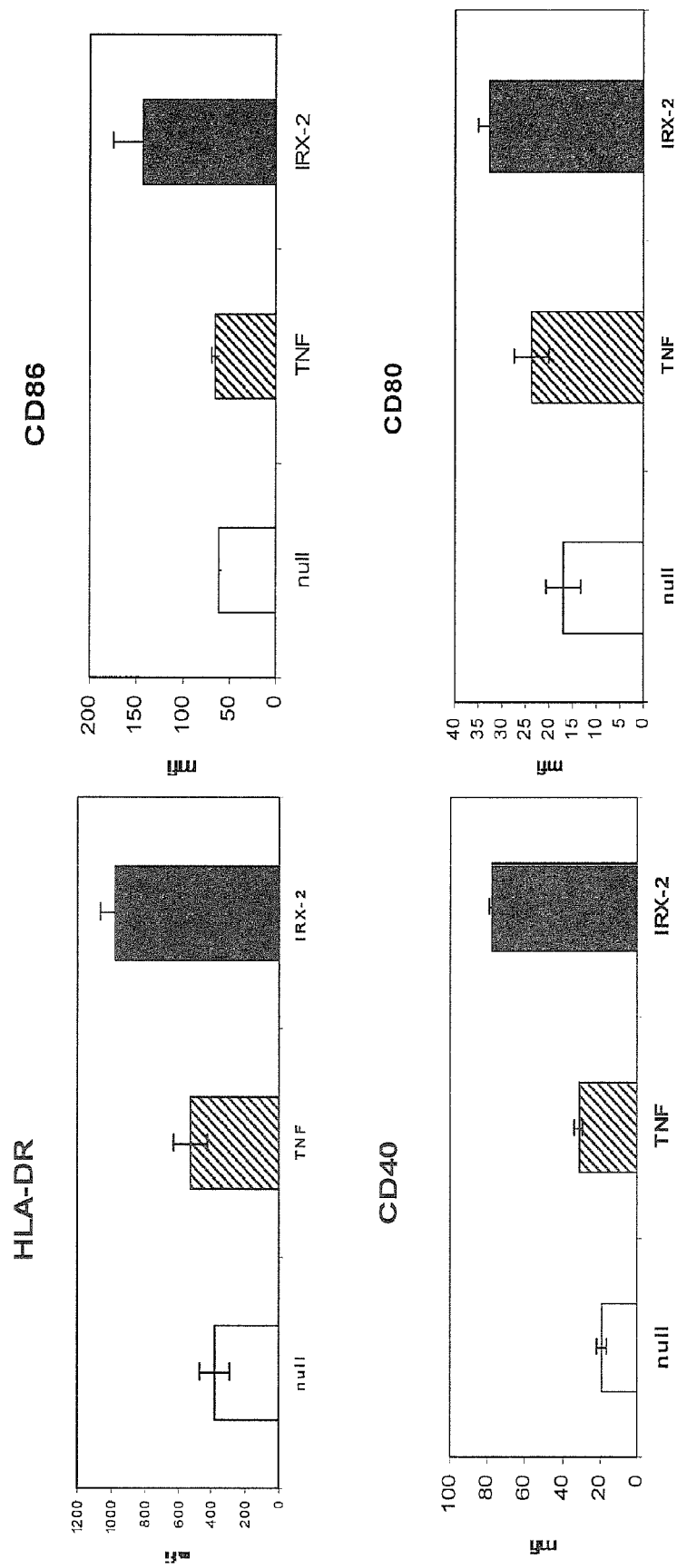
FIG. 20 contains bar graphs demonstrating that the IRX-2 of the invention activates monocytes/macrophages, i.e., induces the expression of activation markers, CD86, HLA-DR, CD80 and CD40, to a greater degree than TNF-α.

In addition, it was found that the IRX-2 of the invention activates monocytes to a greater degree than TNF-α. More specifically, adherent PBMCs were stimulated with either IRX-2 (IRX-2) (at a 1:3 final concentration; approximately 1 ng/ml TNF-α) or TNF-α (10 ng/ml) and assayed for the expression of activation markers by flow cytometry. As shown in FIG. 20, IRX-2 induced statistically greater expression of HLA-DR, CD86, CD40 and CD80 than TNF-α (p<0.03). The data shown in FIG. 20 represent the mean value+/−SEM from three independent experiments/donors.

Figure 21:
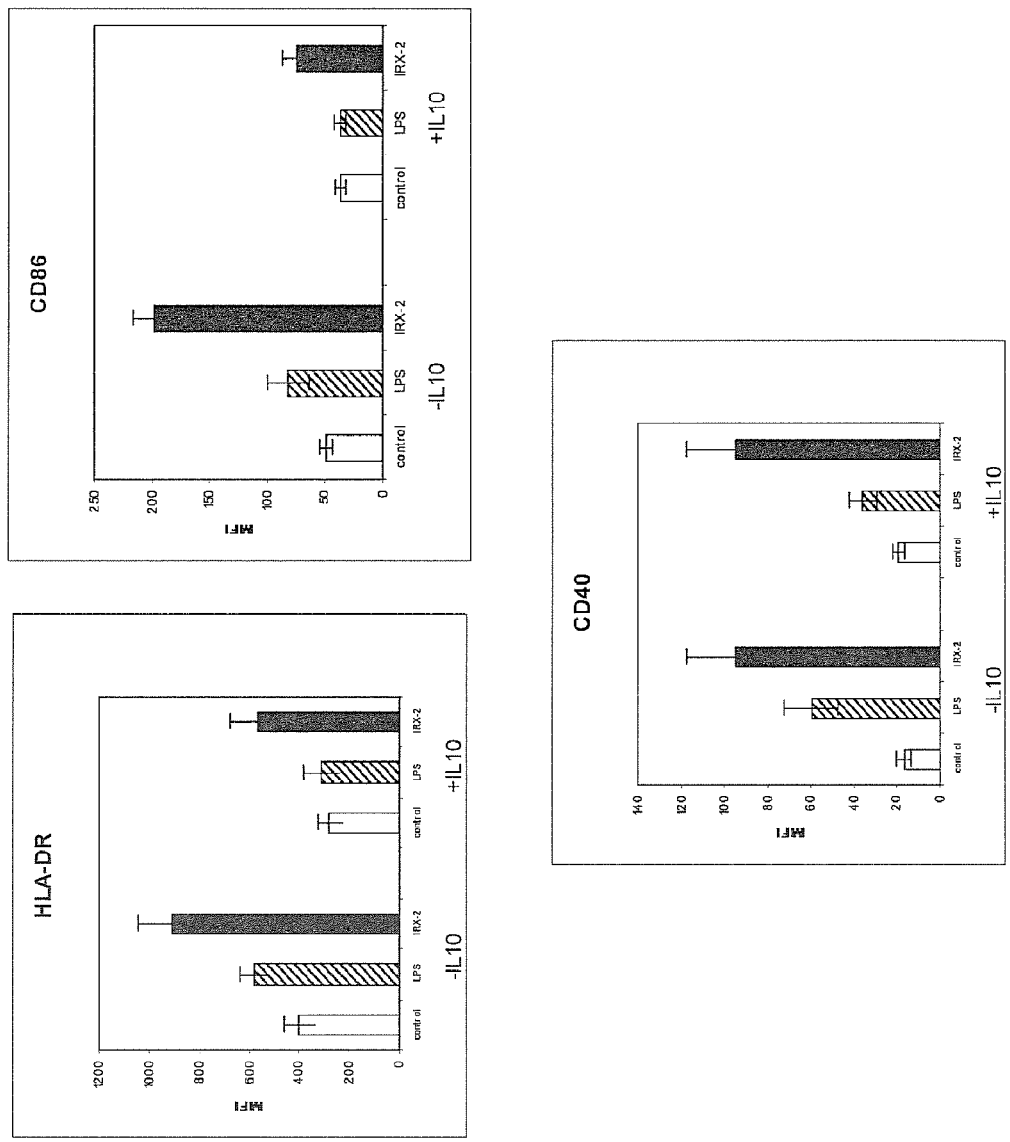
FIG. 21 contains bar graphs demonstrating that the IRX-2 of the invention activates monocytes/macrophages, i.e., induces the activation markers, HLA-DR, CD86 and CD40, even in the presence of the immunosuppressing cytokine IL-10. The IRX-2 is better at activating monocytes/macrophages than LPS, both in the presence and absence of IL-10.

Similarly, studies performed using LPS in modest doses (activating but not maximal) also indicated that IRX-2 was a comparatively stronger activation signal. More specifically, adherent PBMCs were stimulated in the absence or presence of IL-10 (5 ng/ml) with either IRX-2 (IRX-2) (at a 1:3 final concentration) or LPS (10 ng/ml) and assayed for the expression of activation markers by flow cytometry. As shown in FIG. 21, IRX-2 caused a greater increase in the expression of the monocyte/macrophage maturation markers HLA-DR, CD86, and CD40 than LPS. Moreover, in the presence of the immunosuppressing cytokine, IL-10, the IRX-2 was still able to stimulate the monocytes, whereas LPS failed to do so (p<0.02). The data shown in FIG. 21 represent the mean value+/−SEM from three independent experiments/donors.

Figure 22:
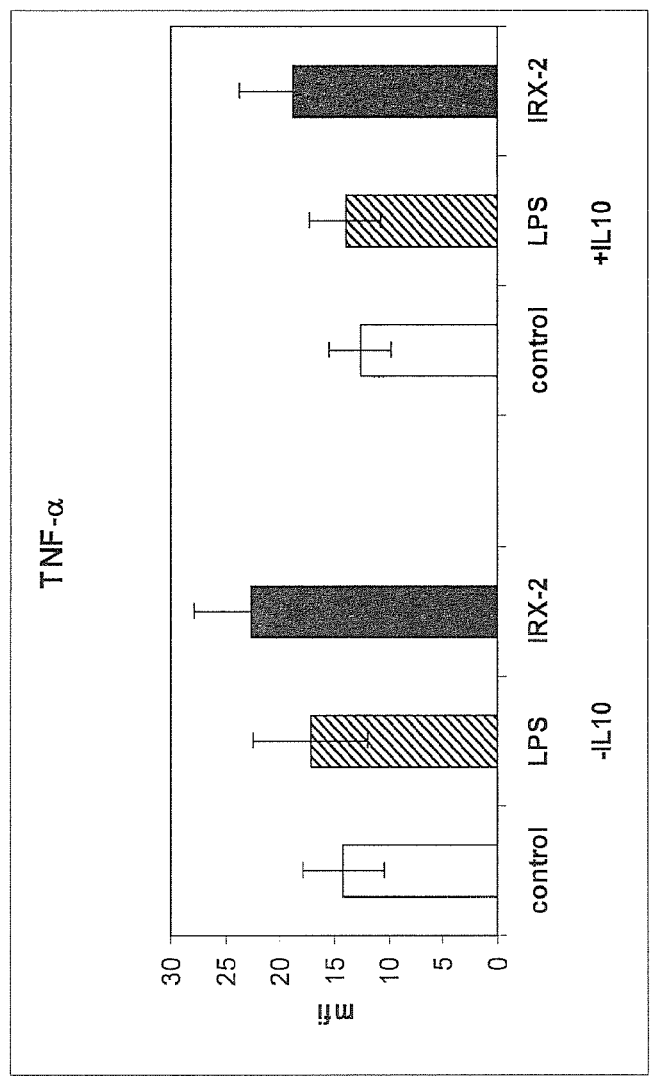
FIG. 22 is a bar graph demonstrating that the IRX-2 of the invention stimulates the production of TNF-α from activated monocytes/macrophages and overcomes the immunosuppressive effects of IL-10, the IRX-2 stimulated the production of TNF-α to a greater extent than LPS.

Finally, it is known that monocytes secrete TNF-α in response to activating signals, which secretion is associated with the non-specific killing activity of the monocytes/macrophages. The data shown in FIG. 22 demonstrate that the IRX-2 of the invention stimulates the production of TNF-α from monocytes and overcomes the immunosuppressive effects of IL-10. More specifically, adherent PBMCs were stimulated in the absence or presence of IL-10 (5 ng/ml) with either IRX-2 (IRX-2) (at a 1:3 final concentration) or LPS (10 ng/ml) and assayed for TNF-α production by intracellular staining and flow cytometry. As shown in FIG. 22, IRX-2 caused a greater increase in the production of TNF-α than LPS or controls. In the presence of IL-10, the IRX-2 was still able to stimulate the monocytes to produce TNF-α, whereas LPS was no longer able to do so (p<0.05). The data shown in FIG. 22 represent the mean value+/−SEM from five independent experiments/donors.

Example 11

The experiments detailed below demonstrate the ability of the IRX-2 composition of the invention to act in combination with exogenous antigens to elicit an improved immune response (both cellular and antibody-based) against the antigen in mice.

Administration of Exogenous Tumor Antigens

Mice:

The procedure was to immunize mice with prostate-specific membrane antigen (PSMA) peptides based on predicted T cell epitopes of PSMA (LLH &ALF) (100 μg@)

were conjugated to either ovalbumin (OVA) or Keyhole Limpet Hemocyanin (KLH). Previous attempts with isolated unconjugated peptides were not successful in mice. IRX-2 (0.1 ml) was given as a single immunization with both conjugated antigens, preceded by low dose CY (400 µg/mouse) and followed by 9 daily injections of IRX-2 (0.1 ml) without antigens, while CpG, alum, or RIBI-Corixa adjuvants were a single primary immunization with the OVA conjugate. Two booster immunizations (conjugate plus adjuvant as above) were given at day 21 and 28 to each group of mice. The DTH reaction to the T cell peptides was measured 9 days after the final boost and serum was taken at sacrifice on days 15-21.

Figure 23:
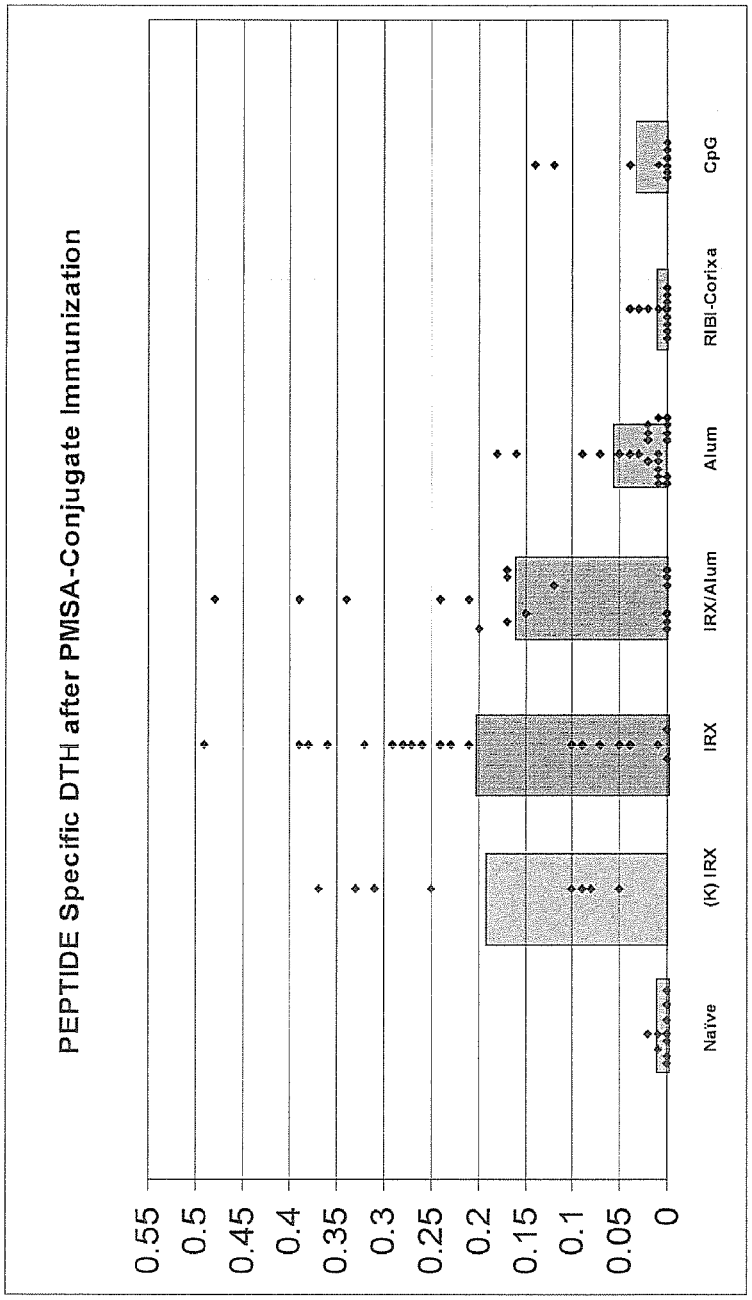
FIG. 23 is a chart illustrating the prostate-specific membrane antigen (PSMA) peptide-specific DTH response of mice immunized with various conjugates and adjuvants, including the IRX-2 of the invention (IRX), wherein the response is indicated as swelling in mm for individual mice (dots) and for the average (bar), the adjuvant is listed on the x-axis, naïve indicates mice not immunized, and all other mice are immunized with Ovalbumin-PSMA peptide conjugates except where indicated (KLH)

FIG. 23 shows the DTH results to skin testing of mice, using the individual ALF and LLH peptides (10 µg@), i.e., without conjugate, as the antigen challenge. As indicated by the Figure, IRX-2 induces significant DTH responses to the antigens following immunization with both conjugates and also when given with alum for the OVA conjugate. Alum, RIBI-Corixa, and CpG showed negligible activity.

Serum Antibody Results:

Serum was diluted as indicated and added to the wells of a microplate coated with either peptide (ALF or LLH) or ovalbumin. Results are expressed as the average OD at 405 for 5 mice groups. Data are presented in Table IV below.

More specifically, mice immunized with the KLH conjugate in combination with IRX-2 were negative for ovalbumin antibodies, but positive for the peptides. Mice immunized with the OVA conjugates and IRX-2 were positive for antibodies for both OVA and the peptides, while those immunized with the OVA conjugate+CpG were positive for OVA only. These results indicate that IRX-2 acts as an adjuvant in enhancing the ability of conjugated PSMA peptides to stimulate both DTH and IgG responses specific for the peptides, while other adjuvants like alum, RIBI-Corixa, and CpG were inactive or poorly active.

Tx). Ovalbumin and cyclophosphamide were obtained from Sigma and KLH from Pierce Biochemicals. The RIBI adjuvant system (R-700), also termed RAS, was purchased from Corixa and alum (40 mg/ml each of aluminum hydroxide and magnesium hydroxide) was purchased from Pierce Chemicals. RAS consisted of Monophosphoryl Lipid A (0.5 mg) and synthetic Trehalose Dicorynomycolate (0.5 mg), and 44 µl Squalene and Tween-80. CpG oligonucleotides (mouse specific sequence) were synthesized by BioSynthesis. The CpG sequence was TCCATGACGTTCCT-GACGTT (SEQ ID NO: 3) and was the phosphothionate derivative. The bioactivity of the CpG in the mouse was confirmed by measuring proliferation of mouse spleen cells and production of TNF-α by mouse adherent cells (data not shown).

IRX-2 (also referred to herein as IRX-2) is a defined mixture of cytokines produced over a 24 hr period following stimulation of human peripheral blood mononuclear cells by PHA and ciprofloxacin. The PHA is removed prior to collecting the supernatant containing the cytokines. Two virus removal steps are included in the subsequent processing (ion exchange and dual nanofiltration). Stringent QC testing that includes both bioassay and ELISA determination of cytokine levels assures the consistency of the IRX-2 (IRX-2). Safety testing with respect to sterility, DNA, micoplasm, endotoxin and virus testing for CMV and EBV are also part of the process. Several lots of IRX-2 were used over the course of these studies. The level of a number of cytokines contained in the IRX-2 (IRX-2) lots are listed in Table V below. In the table, * represents the mean cytokine level for the 5 lots of IRX-2 used in these studies and ** represents levels not measured in all lots but for the most recent lot only. Additional cytokines present in pg/ml ranges include G-CSF, IL-12, and IL-10. Not present are typical Th2-biasing cytokines such as IL-3, IL-4, IL-5, IL-7 and IFN-α. When two lots were tested in the same experiment, they were always similar in activity (data not shown).

TABLE IV

| Dilution IRX-2 | OVA-PSMA IRX-2 | KLH-PSMA-IRX-2 | OVA-PSMA-CpG |
|---|---|---|---|
| A: Serum IgG to ALF Peptide ||||
| 1/200 | 0.929 | 0.692 | 0.241 |
| 1/400 | 0.989 | 0.518 | 0.208 |
| 1/800 | 0.695 | 0.351 | 0.144 |
| 1/1600 | 0.309 | 0.191 | 0.120 |
| B: Serum IgG to LLH Peptide ||||
| 1/200 | 0.950 | 0.720 | 0.277 |
| 1/400 | 1.013 | 0.502 | 0.200 |
| 1/800 | 0.607 | 0.327 | 0.157 |
| 1/1600 | 0.316 | 0.201 | 0.125 |
| C: Serum IgG to Ovalbumin ||||
| 1/500 | 0.920 | 0.269 | 1.050 |
| 1/1500 | 0.632 | 0.185 | 0.955 |
| 1/3000 | 0.457 | 0.146 | 0.813 |
| 1/6000 | 0.259 | 0.104 | 0.537 |

Additional experiments were performed to confirm the above results and to demonstrate that the IRX-2 composition of the invention enhances T cell-specific immune responses in both young and old mice. In the experiments described below, the following methods and materials were used:

Reagents:

Prostate-Specific Membrane Antigen Peptides (Peptide 1: Leu-Leu-His-Glu-Thr-Asp-Ser-Ala-Val (SEQ ID NO: 1); Peptide 2: Ala-Leu-Phe-Asp-Ile-Glu-Ser-Lys-Val (SEQ ID NO: 2)) were synthesized by BioSynthesis Inc. (Lewisville,

TABLE V

| Cytokine Levels in IRX-2 ||
|---|---|
| Cytokine (pg/ml) | Mean* (n = 5) |
| IL-2 | 4.72 |
| IL-1 | 0.45 |
| IFN-γ | 1.28 |
| TNF-α | 1.5 |
| IL-8** | 53.5 |
| IL-6** | 1.1 |
| GM-CSF** | 0.58 |

Conjugation of Antigen Peptides:

Peptides 1 and 2 described above were conjugated to a carrier molecule such as ovalbumin or KLH carriers as described above. Both peptides were conjugated to each carrier, i.e., as a single agent. For example, the OVA-PSMA conjugate or KLH-PSMA conjugate used in these studies contained both peptides linked to the carrier molecule. The peptides were conjugated to the respective carriers using the carbodiimide method (ODC; Pierce EDC kit 77502, Rockford, Ill.). In early studies, gluteraldehyde (Sigma, St. Louis, Mo.) was utilized but there was no difference in immunogenicity between the two methods (data not shown), so the carbodiimide coupling was chosen for subsequent studies as the more controlled method. Conjugation was characterized by measuring OD 280 and 215 in fractions from a Sephadex purification column. The 280 OD peak from the columns represents the ovalbumin or KLH conjugate and was collected as the conjugate. Dosing was based on the carrier concentration as recovered from the column. Monitoring the 215 showed a tailing peak representing the free peptides and provided confirmation that excess peptide was present during the conjugation procedure.

Immunization:

Balb/c mice were purchased from either Charles River or Harlan and were under the care of the Cold Spring Harbor Animal Facility (CSHL). All procedures were approved by the ALAC committee of the CSHL. In several experiments, cyclophosphamide (400 or 2000 µg/100 µl, IP) was injected three days prior to IRX-2 treatment. Subsequent studies demonstrated that cyclophosphamide did not have a statistically significant effect on the IRX-2 (IRX-2) enhancement of the response in mice (data not shown). Immunizations were performed as follows: 200 µl/mouse containing 100 µg of PSMA conjugate with 100 µl adjuvant, e.g., IRX-2 or alum, or PBS were injected subcutaneously at the base of the tail to provide for rapid draining to the regional lymph nodes. Nine additional injections of IRX-2 (100 µl=6-8 IU of IL-2 equivalence) always followed the primary immunization (on days 2, 3, 4, 5, 8, 9, 10, 11, and 12). Unlike alum or RIBI, even repeated injections of IRX-2 (IRX-2) into the same site did not result in significant inflammation at the site (unpublished observation). Two booster immunizations with conjugate plus adjuvant (at day 14 and 28) were performed prior to assessing DTH activity. Additional IRX-2 was not given at the booster immunizations.

In the comparative adjuvant studies in young mice, the RAS (R-700=MPL+TDM in squalene/Tween 80) was reconstituted with 1 ml of PBS (as per the recommended protocol) and then mixed with 1 ml conjugate (1 mg/ml). Alum was mixed 1:1 with antigen. CpG oligonucleotides were mixed with the conjugate as per the published protocols for mice (100 µg conjugate with 20 µg CpG per mouse).

DTH Assay:

The in vivo antigen challenge for the DTH assay was with either a mixture of the two PSMA peptides (without carrier) (100 µg in 20 µl) or carrier alone (ovalbumin or KLH) (50-100 µg in 20 µl). Mice received subcutaneous injections of the challenge antigen in the left footpad and PBS in the right footpad at 9 days after booster immunization. After 24 hrs, the right and left footpad thicknesses were measured using a digital readout caliper (Preisser DIGI-MET Model 18314, Stofiting Co., Wooddale, Ill.). The swelling response was calculated by subtracting the right footpad thickness (baseline) from the left footpad thickness (experimental response). The data were expressed as individual mice swelling as well as mean+/−standard error of the mean. Statistical analysis was via Student's t-test or ANOVA.

Antigen/Mitogen-Induced Cytokine Production and Measurement:

For these studies, the spleens were harvested 14-21 days after the booster immunization and isolated via dispersing through a wire screen. Adherent cells were obtained by taking spleen cells and allowing them to adhere to plastic for 90 minutes. The isolated adherent cells were pooled prior to addition to the cultures to provide for additional antigen-presenting cells. Approximately 6×I05 lymphocytes per well were supplemented with 2×104 adherent cells.

Cytokine release from antigen or mitogen-induced activation of lymphocytes was measured in supernatants using Duo-Sets ELISA reagents from R and D Systems (Minn., MN). The optimal day for harvesting supernatants from antigen-stimulated cells was day 6 (for IFN-γ), while the PHA-stimulated IL-2 production was optimal at day 3 (data not shown).

Serum Antibodies to Ovalbumin and Peptides:

Serum at sacrifice was frozen for later use in ELISA assays. ELISA plates (Immunolon-4, Nunc, Denmark) were coated with the antigen of interest (ovalbumin, KLH, conjugate or individual peptides) overnight. Dilutions of serum were added to the blocked and washed wells and incubated overnight. Anti-mouse biotin and biotin-alkaline phosphatase (Southern BioTech, Birmingham, Ala.) were added sequentially and following addition of pNPP substrate, OD was measured and plotted vs dilution of serum.

The results of these studies as detailed below demonstrate that the IRX-2 of the invention stimulates tumor antigen-specific immune responses in both young and old mice in vivo. More specifically, in the experiments described below, the in vivo DTH (delayed type hypersensitivity) assay was utilized as an indicator of T cell activation. The DTH response to cancer antigens correlates well with elimination of tumor in animal models and clinical trials, and thus provides a useful in vivo correlate of T cell immune responses (see, e.g., Stuart, 1987; Sweat, 1998). As demonstrated by the present experiments, the IRX-2 composition of the invention acts as an adjuvant with prostate-specific tumor antigens in stimulating T cell immune responses in young mice in vivo. Moreover, the present experiments demonstrate that IRX-2 not only increases the immune response to T cell peptides in young mice but also restores T cell immune responses in T cell-impaired old mice. Thus, in the experiments detailed below, old mice were used as a model of immune dysfunction, an age-related decline in immune function that occurs in both mice and men. Furthermore, it is believed that this immune dysfunction is a major reason for the increased cancer incidence that occurs with increasing age in humans.

IRX-2 Enhancement of Peptide-Specific DTH Response in Young Mice:

Young mice were immunized with either IRX-2 (or PBS as a negative control) in combination with an OVA-PSMA or KLH-PSMA conjugate as described above (e.g., 200 µl/mouse, containing 100 µg of conjugate with 100 µl IRX-2 or PBS). Immunizations were administered as subcutaneous injections at the base of the tail to provide for rapid draining to a regional lymph node. The mice were later challenged in a DTH assay as described above, using either the PSMA peptides (FIG. 24A) or the carrier used in the respective conjugate immunizations (FIG. 24B) as the challenge antigen.

Figure 24A:
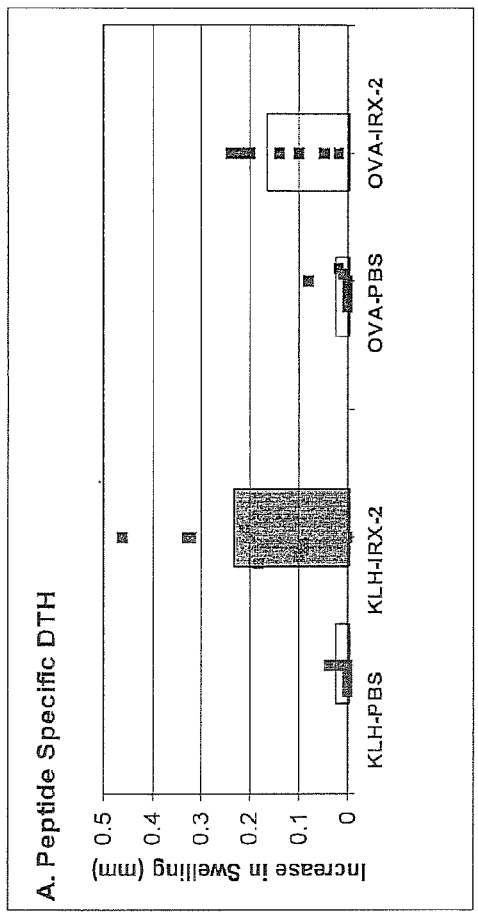
FIG. 24A depicts the enhanced peptide-specific DTH immune response in mice immunized with the IRX-2 of the invention (IRX-2) in combination with either an OVA-PSMA or a KLH-PSMA conjugate and then challenged with the PSMA peptides (used for generating the conjugate) in a DTH assay: the increase in swelling for individual mice is represented by the data points, with the average increase in swelling being represented by the shaded boxes.
Figure 24B:
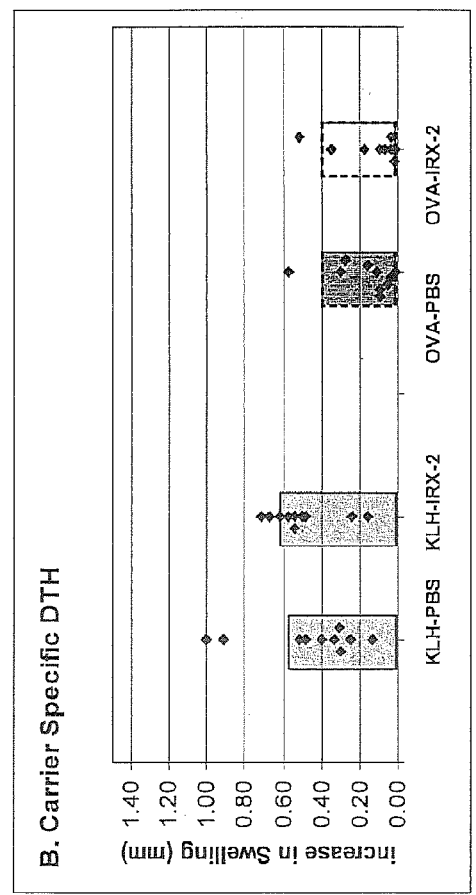
FIG. 24B depicts the DTH response to challenge with only the carrier used in the conjugate immunization.

As demonstrated in FIG. 24A, immunization of young mice (6-8 weeks old) with IRX-2 (IRX-2) in combination with an OVA-PSMA or KLH-PSMA conjugate enhanced the peptide-specific DTH response, regardless of the carrier. When the peptides were co-administered with IRX-2 but without conjugation, no peptide-specific DTH response was measured (data not shown). The DTH response to the carriers (either ovalbumin or KLH) was stronger than to the peptide, and administration with IRX-2 did not enhance the DTH activity (FIG. 24B). Addition of alum to the IRX-2-peptide conjugate immunization did not modify the positive peptide-specific DTH response (data not shown).

The initial studies used IRX-2 (IRX-2) in combination with a single pretreatment with cyclophosphamide three days before immunization. More specifically, mice were immunized with the OVA-PSMA conjugate and IRX-2 (IRX-2) either with or without the administration of cyclophosphamide (either 400 µg/mouse or 2 mg/mouse) 3 days prior to the primary immunization. After two boosts (at day 14 and 28), a DTH assay was performed as described above.

Figure 25:
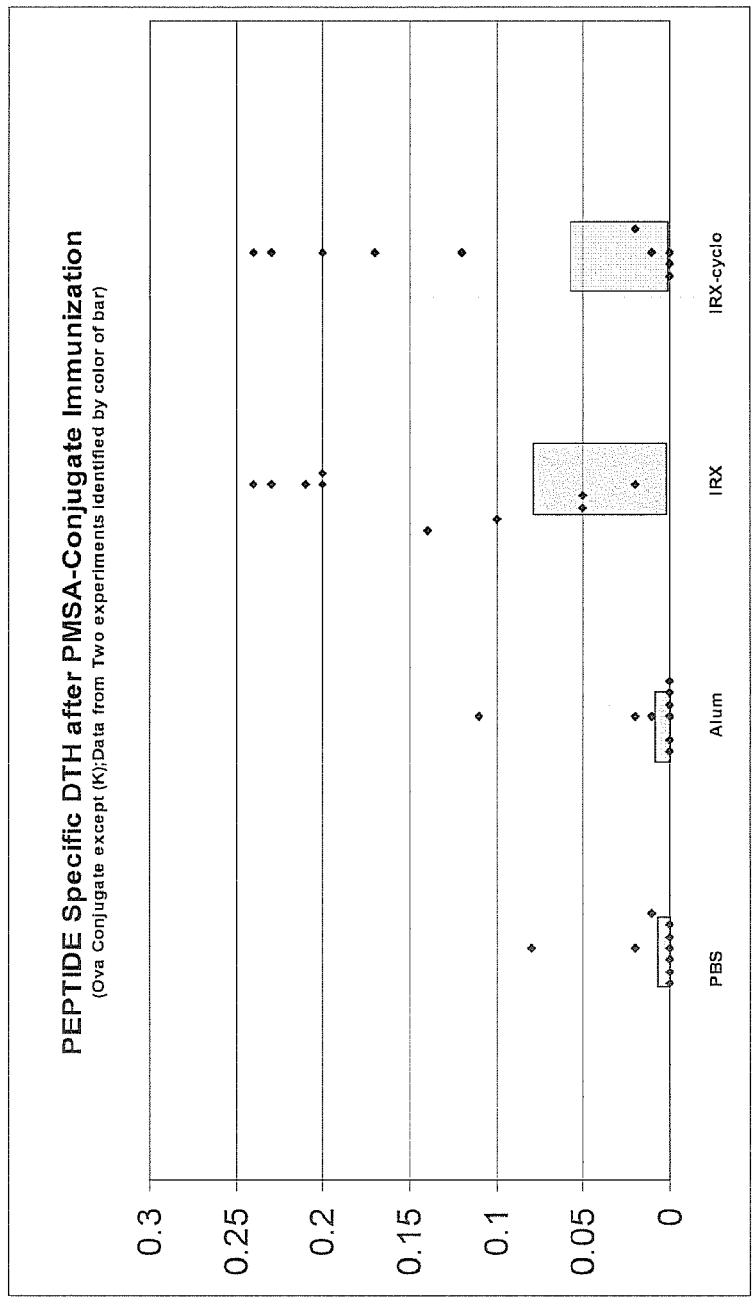
FIG. 25 depicts the influence of cyclophosphamide treatment on the peptide-specific DTH response in mice immunized with the OVA-PSMA conjugate and IRX-2: cyclophosphamide treatment had no effect on the DTH response.

As shown in FIG. 25, the pretreatment with cyclophosphamide was not required for the peptide-specific response and it was not used in subsequent experiments. Moreover, this experiment confirmed that IRX-2 treatment in combination with the peptide-conjugate enhanced the peptide-specific DTH response to a significantly greater extent (p<0.05) than the use of alum or PBS, regardless of whether the mice were pre-treated with cyclophosphamide or not. The results of this assay were expressed as average swelling (bars in FIG. 25) and as the swelling for individual mice (diamond data points in FIG. 25). In addition, all of the results of these mouse studies utilized 9 days of additional IRX-2 (IRX-2) injections after the primary immunization, although 4 additional treatments was not statistically different from 9 (data not shown).

Further, the ability of IRX-2 to stimulate a peptide-specific immune response to the PSMA conjugates was compared to that of three other adjuvants: alum, the RIBI Adjuvant System (or RAS), and CpG. More specifically, mice were immunized with the OVA-peptide conjugate in combination with these different adjuvants. After two boosts (on day 14 and 28), a DTH assay was performed as described above (on day 9 post-boost). The results of this study are indicated in FIG. 26 and are expressed as the average swelling (bars) and as the swelling for individual mice (diamond data points).

Figure 26:
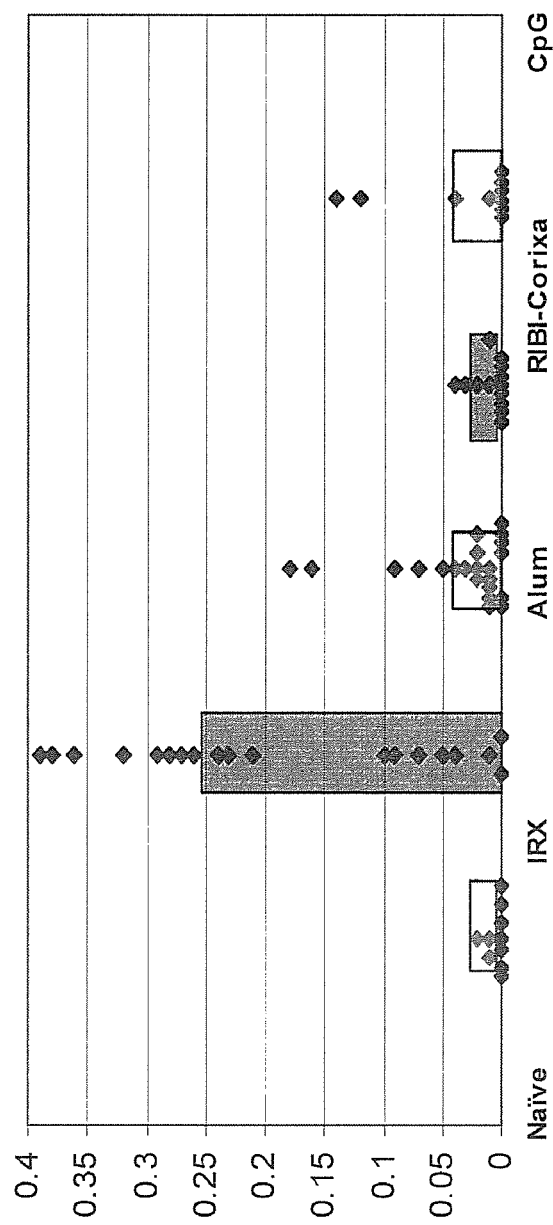
FIG. 26 depicts a comparison of the effects of various adjuvants, including the IRX-2 of the invention (IRX), on the peptide-specific DTH response in mice immunized with a PSMA conjugate in combination with the respective adjuvants: the adjuvant effect of IRX-2 was greater than the other adjuvants tested, and naïve mice, i.e., non-immunized mice, represent a negative control.

As depicted in FIG. 26, the adjuvant effect of IRX-2 (IRX-2) was greater than those of the other adjuvants tested (p<0.001). Although all of the adjuvants enhanced the response to the carrier protein compared to naïve mice (data not shown), only IRX-2 (IRX-2) enhanced the tumor peptide-specific immune response.

IRX-2 Enhancement of Peptide-Specific Immune Response in Aging Mice

We first confirmed that the T cell immune response in old mice (>18 months old) was deficient as compared to the response in young mice (8-16 weeks old) by demonstrating that spleen cells from old mice stimulated with mitogen (PHA) were impaired with respect to secretion of two primary T cell cytokines, IL-2 and IFN-γ, as compared to the response from young mice (IL-2: 285 vs 75 pg/ml and IFN-γ: 1535 vs 128 pg/ml).

We then tested the DTH response in old versus young mice that had been immunized with PSMA conjugates and either IRX-2 or alum as adjuvant, followed by antigen challenge using the DTH assay described above. More specifically, old mice (18-20 months at the start of the study) and young mice (6-8 weeks at the start of the study) were immunized with the PSMA conjugate, OVA-PSMA, in combination with IRX-2 or alum as adjuvant, as described above. The mice were then challenged with antigen according to the DTH assay described above.

Figure 27A:
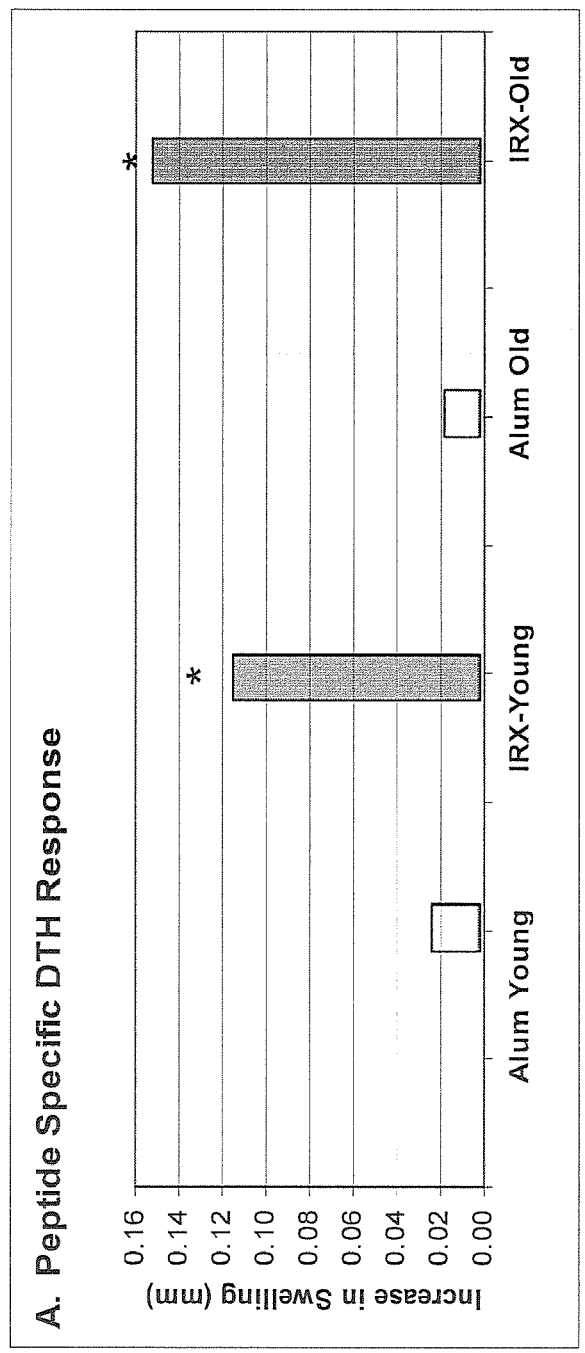
FIG. 27A depicts the peptide-specific DTH response of old versus young mice immunized with an OVA-PSMA conjugate in combination with either IRX-2 (IRX) or alum as adjuvant: the IRX-2 of the invention stimulated a greater peptide-specific DTH response in both old and young mice as compared to alum.

As indicated by FIG. 27A, IRX-2 (IRX-2) restored the immune activity of old mice to that of young mice with respect to the peptide-specific DTH response. The results are expressed as difference in swelling between a PBS-injected paw and an antigen-injected paw for the mean of 9-15 mice per group. The average swelling for the IRX-2-treated old and young groups was not statistically different with respect to the peptide-specific response. However, the DTH responses of both the IRX-2-young and IRX-2-old groups were significantly greater than that seen from the alum-treated mice (* p<0.005, Student's t-test).

Figure 27B:
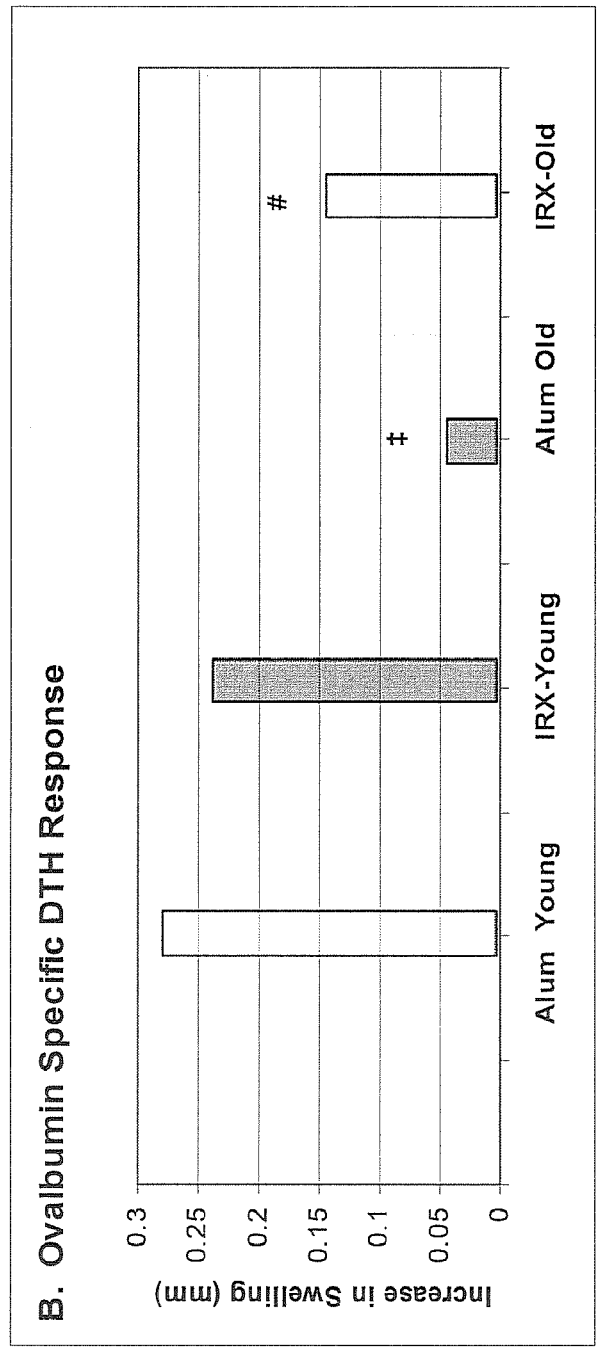
FIG. 27B depicts the carrier-specific DTH response of old versus young mice immunized with a PSMA conjugate in combination with either IRX-2 (IRX) or alum as adjuvant: the IRX-2 of the invention restored the carrier-specific DTH response in the old mice to that observed in the young mice.

With respect to the OVA carrier-specific DTH response, FIG. 27B demonstrates that the old mice were deficient compared to the young mice for this response (p<0.05) but IRX-2 treatment restored the ovalbumin-specific DTH response in the old mice (FIG. 27B). The response of young mice to ovalbumin was optimal in alum and was therefore not improved by IRX-2.

These experiments demonstrated the adjuvant effect of the IRX-2 composition of the invention in stimulating specific anti-tumor antigen T cell immune responses in both old and young mice in vivo. In fact, the IRX-2 of the invention provided a greater tumor antigen-specific T cell immune response compared to other adjuvants tested.

Further experiments, as described below, were carried out to measure the effect of IRX-2 treatment on the production of the T cell cytokine, IFN-γ, which production is another indicator of immune stimulation.

Effect of IRX-2 on the Spleen T Cell Ex vivo Response

Figure 28:
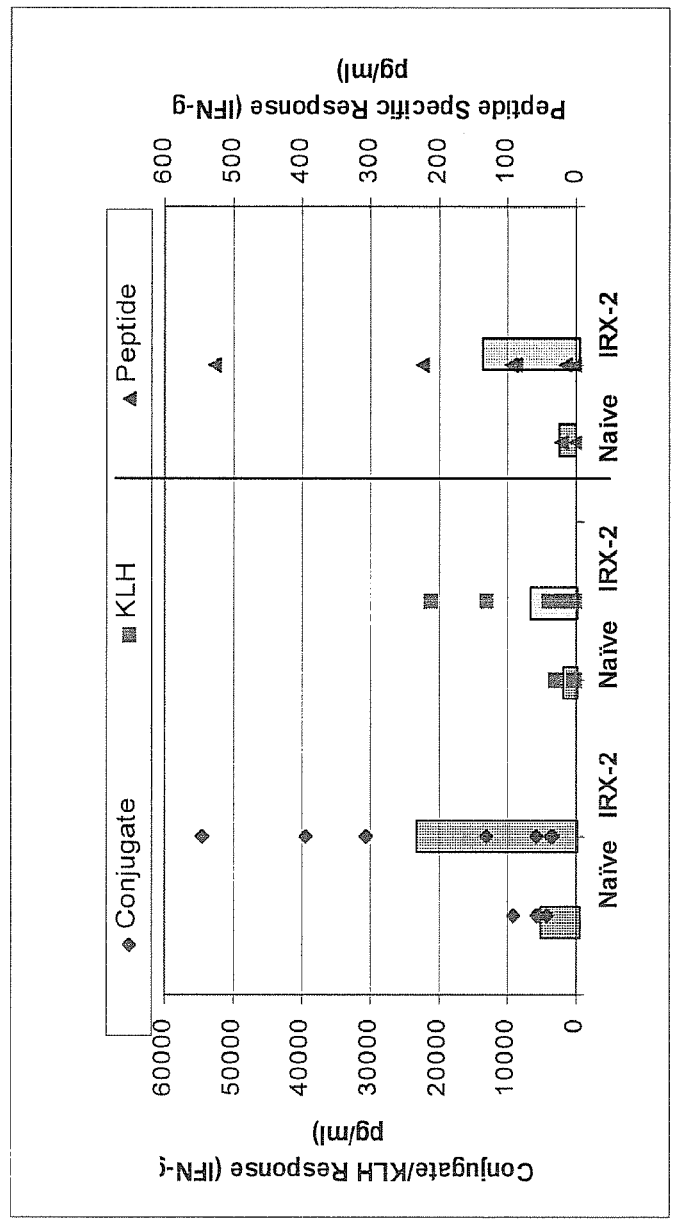
FIG. 28 depicts the enhanced T cell response in the form of IFN-γ secreted by spleen cells from mice immunized with a KLH-PSMA conjugate and the IRX-2 of the invention (IRX-2), the results are expressed for individual mice (data point markers) as well as the average response (shaded bars): all increases in IFN-γ secreted were statistically significant compared to naïve controls.

Thus, the adjuvant effect of IRX-2 treatment on mice immunized with IRX-2 and a PSMA conjugate was determined by measuring the secretion of IFN-γ by spleen cells from the immunized mice. More specifically, spleen cells from mice immunized with the KLH-PSMA conjugate (as described above) and IRX-2 (IRX-2) were harvested and incubated ex vivo with the conjugate (KLH-PSMA), the carrier (KLH) or the peptides (PSMA). The supernatants from the spleen cells were collected after 6 days of culture and measured for IFN-γ secretion as described in the methods and materials section above. As shown in FIG. 28, the T cell response, in the form of production of IFN-γ (in pg/ml), was greater for all three antigens in mice immunized with the conjugate and IRX-2 as compared to naïve mice.

Effect of Adjuvants on the Serum Antibody Titer

Figure 29A:
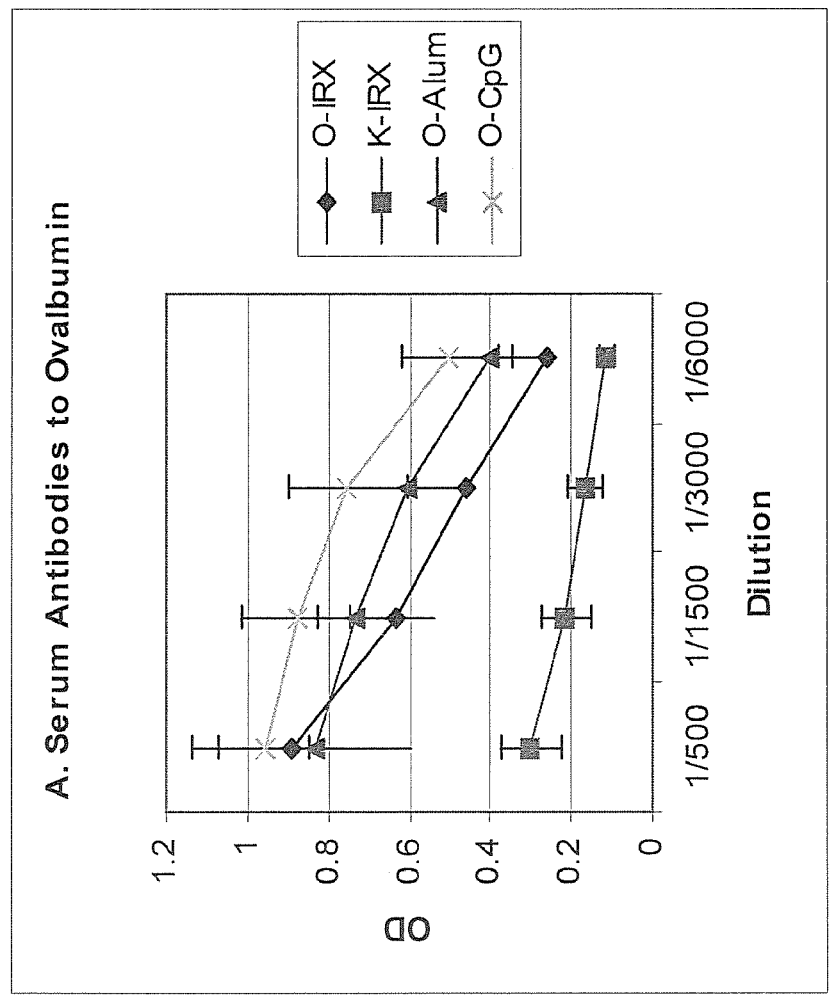
FIGS. 29A-C depicts serum antibody responses observed in mice immunized with the PSMA conjugates in combination with the IRX-2 of the invention compared to other adjuvants, i.e., alum and CpG.
Figure 29B:
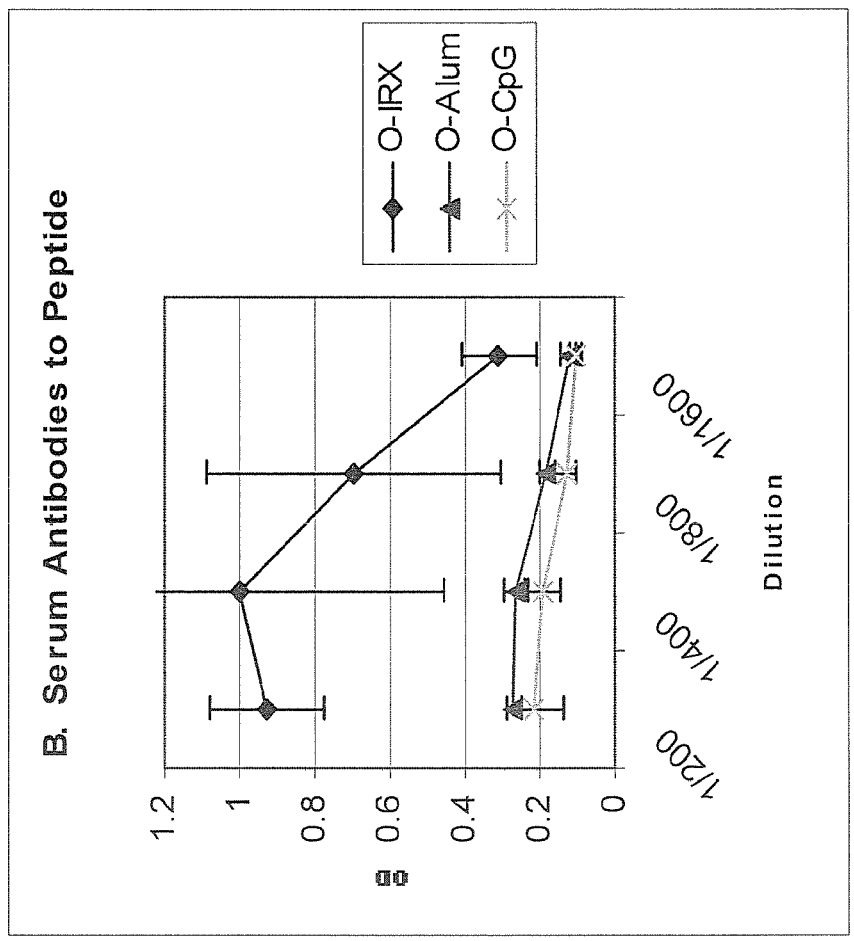
Figure 29C:
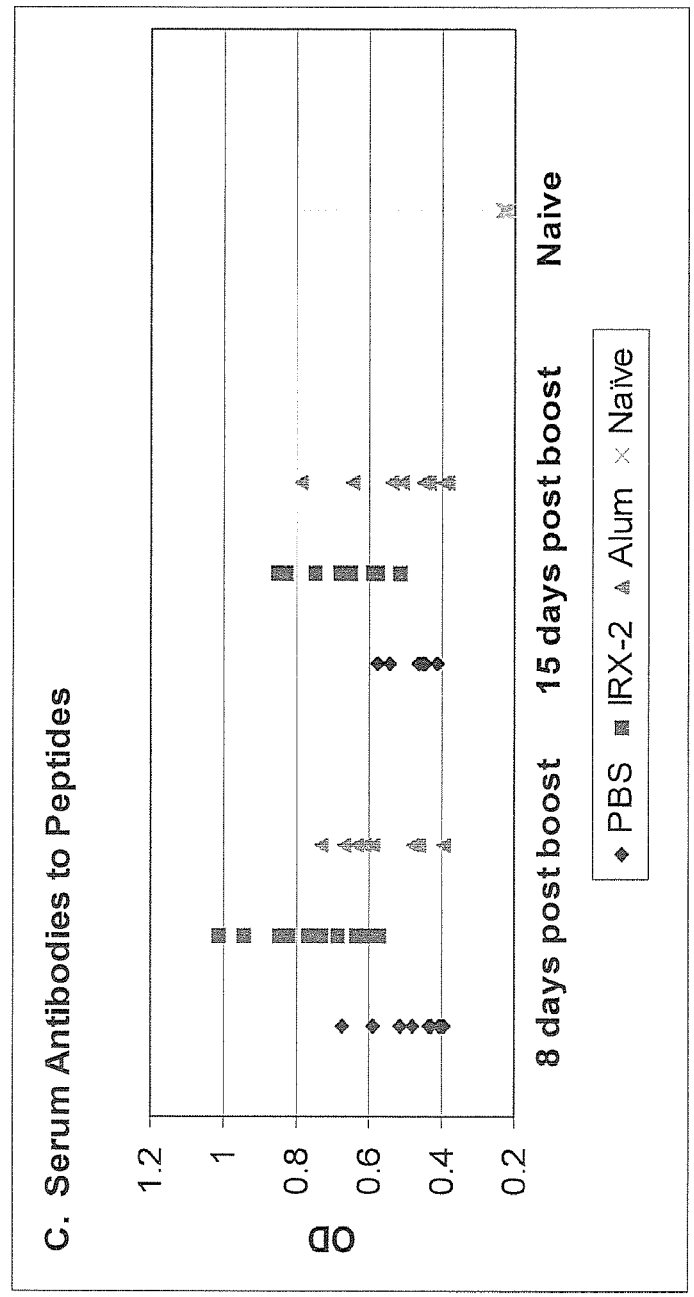

In addition, experiments were performed to determine whether IRX-2 treatment had an adjuvant effect on antibody production in vivo. More specifically, mice were immunized with the PSMA-conjugates as described above and the following adjuvants: IRX-2, alum or CpG. PBS was used as a negative control for adjuvant. Serum from the mice was obtained at sacrifice, either at 15 days after the third immunization (data depicted in FIGS. 29A and B) or at 8 and 15 days after the third boost (data of FIG. 29C)). Serum was assayed for antibodies by ELISA and the results expressed as dilution vs optical density (FIGS. 29A and B) or as optical density at the optimal dilution, 1/400 (FIG. 29C).

Serum antibody titers to the carrier (whether ovalbumin or KLH) were measured and indicated that IRX-2 (IRX-2), alum and CpG induced similar titers to ovalbumin, with the response being: CpG>alum>IRX-2 (IRX-2) (FIG. 29A and data not shown). Mice immunized with the KLH conjugate, as predicted, did not generate titers to ovalbumin, confirming the specificity of the ELISA assay (see, e.g., FIG. 29A). However, as to the peptide-specific antibody response as depicted in FIG. 29B, IRX-2 in combination with the OVA-PSMA peptide conjugate induced serum antibodies to both peptides, in contrast to alum and CpG. The data in FIG. 29B are for the ALF peptide with a p<0.05 by ANOVA for IRX-2 vs. alum and CpG. Similar responses were measured for the LLH peptide (data not shown). As depicted in FIG. 29C, when KLH was used in the conjugate as the carrier for the peptides, IRX-2 (IRX-2) induced a higher peptide antibody response than no adjuvant (PBS) or alum (p<0.001 for IRX-2 vs. alum and PBS). The markers in FIG. 29C indicate individual mice. The antibody response was measured on an ELISA plate coated with both peptides in the assay method as described above.

The studies described above indicate that the IRX-2 of the invention enhances the T cell peptide-specific DTH response in vivo and the T cell response of spleen cells ex vivo in a prototype prostate peptide vaccine model. The critical nature of the mixture of cytokines (as opposed to the activity of just a few) is confirmed by the observation that preparations made from cell cultures lacking monocytes and therefore deficient in monocyte-derived cytokines failed to enhance the peptide-specific DTH response or the in vitro T cell response of spleen cells. The novel nature of the IRX-2 was further demonstrated by comparing it to other adjuvants selected to represent various mechanisms of action. For example, CpG is a TLR agonist for APCs and is representative of TLR activating adjuvants, whereas the RAS system is representative of adjuvants with oil and bacterial components and is a safer alternative to Freund's adjuvant in mouse models. Alum is the adjuvant utilized in the majority of FDA-approved vaccines. In the present studies, IRX-2 enhanced the peptide-specific DTH response but alum, CpG and RAS did not. Moreover, the IRX-2 enhancement of the in vivo T cell peptide-specific DTH response correlated with an enhanced T cell response by spleen cells ex vivo as defined by antigen-specific secretion of IFN-γ. Finally, while all of the adjuvants enhanced the antibody response to the carrier (as compared to PBS), only IRX-2 enhanced the antibody response to the peptides conjugated to the carrier.

The mechanism(s) through which the cytokines in IRX-2 act to enhance the peptide-specific immune response as defined by the DTH assay is most likely complex since the recruitment, engulfment, proliferation, activation, maturation and migration of APCs and recruitment, proliferation, differentiation and maturation of T cells are all influenced by cytokines. However, the peptide-specific nature of the DTH response observed in these studies is believed to be a result of the influence of IRX-2 on antigen presentation as well as subsequent T cell proliferation and migration to the periphery. It is also believed that the cytokines of the IRX-2 shift the DC tolerance or T regulatory balance towards activation of the response to T cell epitopes. IRX-2 may also be enhancing the T cell helper epitopes in the carrier providing additional stimulation of the development of an effective T cell immune response. As demonstrated herein (see Examples 9 and 10), the IRX-2 of the invention stimulates the maturation and activation of dendritic cells, which promotes antigen presentation and the secretion of IL-12 (by the dendritic cells), IL-12 being a potent Th1 polarizing cytokine. The IRX-2 is also a potent activator of monocytes and macrophages.

The IRX-2 has further effects on T cells based on the known influence of the cytokines present in the IRX-2. As demonstrated in Examples 2 and 8 above, the IRX-2 of the invention increases T lymphocyte counts in lymphocytopenic patients, including the production of naïve T cells. In addition, it is known that IL-1 (present in the IRX-2) is a chemoattractant for lymphocytes as well as a stimulator of the production of other cytokines. Known activities include increase in the proliferation and activation of resting T cells by inducing IL-2 secretion and, more importantly for the activity of IRX-2, up regulation of IL-2 receptor. In addition, TNF-α (also present in IRX-2) enhances the activity of IL-1 as do other cytokines such as IL-8 and the CSFs. IL-8 also acts as a chemoattractant for multiple cells including T cells, basophils and neutrophils. IL-2 acts to enhance proliferation of activated cells by not just stimulating through the receptor but also by up-regulating additional IL-2 receptors as well as receptors for additional cytokines. Thus, the cytokines of the IRX-2 compositions of the invention are pleotropic, influencing monocytes, dendritic cells and T cells.

The site of activity for the cytokines, present in physiological levels in the IRX-2 of the invention, is local and includes both the injection site as well as the lymph nodes associated with the injection site. Since the IRX-2 can be administered daily, elevated local levels of all the cytokines can be maintained. The peptide-specific nature of the DTH response using the IRX-2 of the invention as an adjuvant argues for the use of the IRX-2 in future T cell vaccines.

In addition, the present studies indicate that the IRX-2 of the invention corrects a T cell cytokine deficit in aging mice. It is important to note that cancer more often occurs in older individuals who are known to have a declining immune system. Moreover, many of the current therapies for tumors (irradiation and chemotherapy) may themselves be immune suppressive, further reducing the immune competence of the patient. Thus, a cancer vaccine for many patients may benefit from an agent with the potential to restore the immune deficiency associated with aging, cancer treatments and cancer defense mechanisms. Given this potential obstacle to the use of a vaccine in the elderly, IRX-2 was evaluated in the present studies for efficacy in aging as well as young immune competent mice. Spleen cells from old mice were first ascertained to be deficient in cytokine production of both IL-2 and IFN-γ when compared to young mice. The DTH response was also impaired with respect to ovalbumin. Not only was IRX-2 composition of the invention capable of restoring the weak response to the carrier, it was also effective in restoring the peptide-specific response to levels similar to that of young mice.

The protocol for the use of IRX-2 in a vaccine model is based on phase I/II clinical studies using the IRX-2 (IRX-2) in patients with head and neck cancer and the known kinetics of the immune response (see, e.g., Meneses, 2003; Hillman, 1995). In clinical trials, targeting the tumor draining lymph node combined with a pre-injection of low dose cyclophosphamide and a 10 day IRX-2 (IRX-2) administration results in enhancement of lymphocyte infiltration of the tumor, fragmentation of the tumor architecture and reduction in tumor size (see Examples 2-7 above). As described above, in the vaccine model in mice, initial studies used a pre-injection with cyclophosphamide but subsequent studies confirmed that this was not necessary in healthy non-tumor bearing mice (FIG. 25). Moreover, the daily administration of IRX-2 after the primary immunization (for 4-9 days) appears to be important because it assures that the site of the injection and subsequently the draining lymph nodes have sufficient cytokine levels for optimal stimulation of the T cell immune response during the activation to memory transition period. Since the levels of the cytokines are low, there is no overt inflammatory response at the site of injection. This is in contrast to both alum and the RIBI Adjuvant System where swelling and inflammation were noted at the injection site (unpublished observation).

The proposed peptide-carrier vaccine described herein has significant clinical promise as a therapeutic vaccine based on data reported for Phase I/II studies using the PSMA peptides without conjugation to a carrier (Toja, 2000; O'Hagan, 2001; Katsuyuki, 2000; and Naylor, 1991). The two peptides are T cell epitopes based on both computer modeling and the response of lymphocytes from prostate cancer patients. When patients were treated with peptides alone or with peptide-pulsed dendritic cells, improved clinical and T cell responses were seen in the Phase I/II trials. In the phase I trials, however, the peptides without an adjuvant were less effective than the peptide-pulsed dendritic cells. Given the enhanced peptide-specific response observed when IRX-2 was administered with the peptide-conjugate and the safety of KLH-conjugates in a wide variety of clinical trials, clinical trials with the peptides and IRX-2 (IRX-2) are warranted.

The studies presented herein using a cancer peptide vaccine mouse model and the human clinical data showing a vigorous anti-tumor response to endogenous antigens using the IRX-2 of the invention, support the use of the IRX-2 composition of the invention in a tumor vaccine for the generation of an immune response sufficient to mediate tumor-specific destruction. In addition, since IRX-2 acts to enhance T cell-specific responses in both young and old mice, IRX-2 is a candidate for inclusion in any cancer vaccine, especially for elderly cancer patients, that has as its goal the enhancement of T cell immune responses.

Humans:

Three patients with advanced prostate cancer received unconjugated ALF & LLH peptides (100 µg @) with IRX-2 (1 ml-100 units IL-2 equivalence) preceded by low dose CY (300 mg/m2) and daily INDO (25 mg tid) plus 9 additional injections of IRX-2 (1 ml). On day 15, a booster of IRX-2 plus peptides was given. An additional patient (#4) received OVA-conjugated peptides in this regimen. Delayed hypersensitivity reactions (DTH) were measured with IRX-2 (0.1 ml), ALF or LLH (10 µg) by intradermal skin test read at 24 hours in centimeters of erythema and in duration. The results are presented in Table VI.

TABLE VI

DTH to PSMA peptides & IRX-2

|  |  | Time 0 | 1 month |
|---|---|---|---|
| IRX-2 | 1) 0 | 0.5 |
|  | 2) 1.0 | 1.0 |
|  | 3) 0.5 | 1.0 |
|  | 4) 0.3 | 0.3 |
| ALF Peptide | 1) 0 | 0.5 |
|  | 2) 0 | 0.1 |
|  | 3) 1.0 | 1.0 |
|  | 4) 0 | 0.4 |
| LHH peptide | 1) 0 | 0.5 |
|  | 2) 0 | 0.3 |
|  | 3) 1.5 | 2.0 |
|  | 4) 0 | 0.5 |

These data indicate that the IRX-2 regimen is effective in inducing DTH reactions to unconjugated and conjugated PSMA peptides in humans with advanced prostate cancer. This result is different from results of most prior attempts that have failed with isolated peptides.

Further experiments demonstrated the ability of the IRX-2 of the invention to act as an adjuvant with PSMA peptide antigens, resulting in the stabilization of disease. More specifically, three HLA-A2 positive males with advanced prostate cancer were treated with IRX-2 (IRX-2) (115 units IL-2 equivalence) and the two PSMA peptides described above (100 µg each). The initial immunization was via injection in the neck, followed by nine injections of IRX-2 (IRX-2) (plus low dose cyclophosphamide, indomethacin and zinc as in the protocol of Example 2 above), and then followed by five monthly boosters of IRX-2 plus the two peptides.

Table VII summarizes briefly the clinical history (Hx) and responses to therapy (Rx). All three patients had received prostatectomy and orchiectomy 4 to 10 years before (in addition to other meds) and had relapsed. All were in a doubling phase of the rise in PSA ranging from 4 to an estimated 6 months. Two were symptomatic with bone pain. The immunization with IRX-2 plus peptides and follow up booster injections induced no symptoms.

Figure 30:
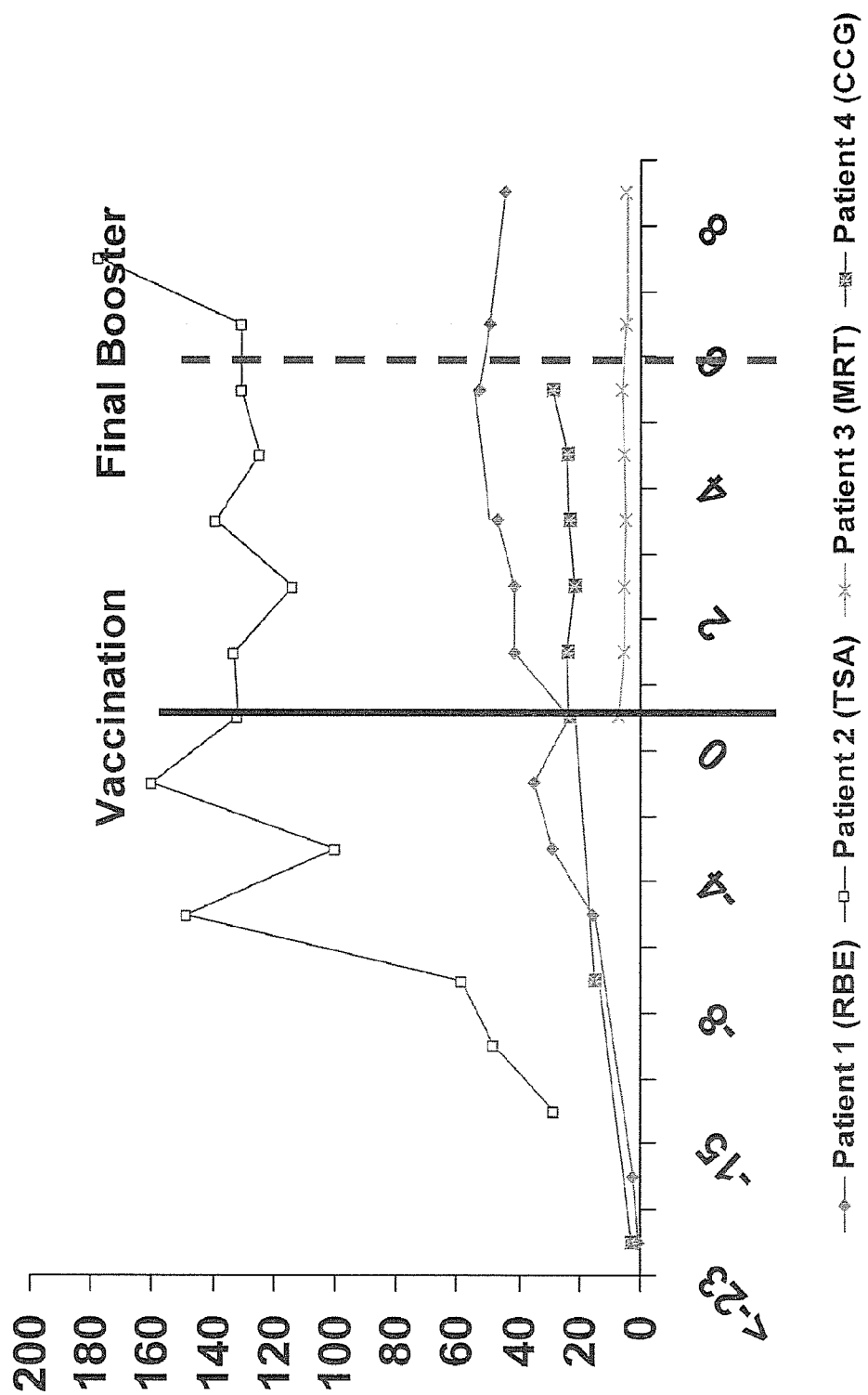
FIG. 30 depicts the stabilization of PSA levels over a 6 month period in three prostate cancer patients treated with the IRX-2 of the invention in combination with PSMA peptide antigens.

The two patients with bone pain had a clearing of pain. All three patients were stable clinically (except that patient #2 suffered a fracture of the femur with a transient exacerbation). All three developed transient dermal reactivity to skin tests with the isolated PSMA peptides (A and B; 10 µg each). All three showed increased reactivity to skin tests with IRX-2 or PHA. These results indicate that the IRX-2 of the invention immunized these patients to the PSMA peptides and stabilized disease during the period of immunization and boosting. See also FIG. 30, which depicts the stabilization of PSA antigen levels in these three patients over a six month period. The additional patient #4 described above showed transient PSA and clinical stabilization but clinical information is incomplete. A further additional patient with an early recurrence of PSA level (7) showed reversion to a normal level which has persisted for two years of follow-up without additional therapy (a complete response).

TABLE VII

|  | Prostate Rx | PSA Hx | IRX-4 Rx | Clinical Response |
|---|---|---|---|---|
| Patient 1 | Prostatectomy 1999 | 2x increase in last 6 | 2003 | PSA stable 5 months; 29 at end |
|  | Orchiectomy 2002 | months (est.) |  | IRX-2 skin test 0.4 1.0 cm |
|  | Bone metastases | Last PSA 24 |  | Peptide A 0 → 0.2 cm |
|  |  |  |  | Peptide B 0 → 0.1 cm |
|  |  |  |  | Stable clinically 6 months |
| Patient 2 | Prostatectomy 1998 | 4x increase in last 12 | 2003 | PSA stable 7 months; 131 at end |
|  | Orchiectomy 1998 | months |  | IRX-2 skin test 1.0 1.0 cm |
|  | Anti-androgens 1999 | Last PSA 160 |  | Peptide A 0 → 0.2 cm |
|  |  |  |  | Peptide B 0 → 1.0 cm |
|  |  |  |  | Decreased pain |
|  |  |  |  | Stable clinically 6 months |
| Patient 3 | Prostatectomy 1993 | 15x in last 20 months | 2003 | PSA stable 7 months; 44 at end |
|  | Orchiectomy 1993 | 2x in last 4 months |  | IRX-2 skin test 0.0 0.5 cm |
|  |  | Last PSA 35 |  | Peptide A 0 → 0.5 cm |
|  |  |  |  | Peptide B 0 → 0.5 cm |
|  |  |  |  | Decreased pain |
|  |  |  |  | Stable clinically 6 months |

Example 12

In the following study, IRX-2 was shown to amplify the T cell response to two T cell-specific peptides from prostate-specific membrane antigen (PSMA). IRX-2 enhanced the PSMA peptide-specific delayed-type hypersensitivity "DTH" response of mice immunized with irradiated 3T3 cells expressing PSMA (cell based vaccine) as well as to a peptide-carrier conjugate vaccine. This was in contrast to adjuvants such as alum, RIBI Adjuvant System (RAS®, RIBI ImmunoChem Research, Inc.) and CpG which were not active in generating T cell responses to the PSMA peptides. T cell-specific in vivo activity was confirmed by demonstrating peptide-specific increases in IFN-γ secretion by spleen cells harvested from immunized mice. IRX-2 in contrast to other adjuvants also enhanced B cell responses to the peptides.

Materials and Methods

Reagents and Cells

Prostate Specific Membrane Antigen Peptides (Peptide 1=Leu-Leu-His-Glu-Thr-Asp-Ser-Ala-Val (SEQ ID NO: 1); Peptide 2=Ala-Leu-Phe-Asp-Ile-Glu-Ser-Lys-Val (SEQ ID NO: 2)) were synthesized by BioSynthesis Inc. (Lewisville, Tex.). Ovalbumin, cyclophosphamide and RIBI adjuvant system (RAS; R-700) was purchased from Sigma (St Louis, Mo.). KLH and alum (40 mg/ml each of aluminum hydroxide and magnesium hydroxide) were from Pierce Biotechnology (Rockford, Il). The RAS consisted of Monophosphoryl Lipid A (MPL; 0.5 mg) and synthetic Trehalose Dimycolate (TDM; 0.5 mg), and 44 ul squalene and Tween-80. CpG oligonucleotides (mouse specific sequence) were synthesized by BioSynthesis (Lewisville, Tex.). The CpG sequence was TCCATGACGTTCCTGACGTT (SEQ ID NO: 3) and was the phosphothionate derivative. The bioactivity of the CpG in the mouse was confirmed by measuring proliferation of mouse spleen cells and production of TNF-α by mouse adherent cells (data not shown).

NIH 3T3 cells that were stably transfected with a PSMA insert were cultured with 10% FBS supplemented MEM. The expression of the insert was confirmed by demonstrating geneticin resistance and expression of PSMA by immunohistochemistry and flow cytometry. Cell were irradiated with 800 Gy using a Cesium source and frozen at −20 C until use as a cell based vaccine.

IRX-2 is a primary cell-derived biologic consisting of multiple active cytokines as described above. IRX-2 dosing is based on the IL-2 content. When two lots were tested at equivalent IL-2 content in the same experiment they were always equal in activity (data not shown). Several lots of IRX-2 were used over the course of these studies. The average levels of the potential immune enhancing cytokines in the lots of IRX-2 used in these studies were IL-2 (5.5 ng/ml), IL-1 (0.5 ng/ml), IFN-γ (1.5 ng/ml), TNF-α (2.7 ng/ml), IL-6 (1 ng/ml) and IL-8 (46.2 ng/ml).

Conjugation

Peptides were conjugated to ovalbumin or KLH using the carbodiimide method (ODC; Pierce EDC kit 77502, Rockford, Ill.). Conjugation was characterized by measuring optical density at 280 nm and 215 nm in fractions from a Sephadex purification column. The 280 nm peak from the columns identifies the carrier and was collected as the conjugate. Monitoring the optical density at 215 nm showed a tailing peak representing the free peptides and provided confirmation that excess peptide was present during the conjugation procedure. Dosing was based on the carrier concentration as recovered from the column.

Immunization

Balb/c female mice (6-8 weeks of age) were purchased from either Charles River Laboratories (Wilmington, Mass.) or Harlan Laboratories (Indianapolis, Ind.) and were housed under the care of the Cold Spring Harbor Laboratory (CSHL) Animal Facility (animal welfare assurance certificate number A3280-01). All procedures were approved by the ALAC committee of the CSHL. Immunizations (200 ul/mouse containing 100 ug of conjugate with 100 ul adjuvant or PBS) were given subcutaneously at the base of the tail to provide for rapid draining to the regional lymph nodes. Nine additional injections of IRX-2 followed the primary immunization (Days 2, 3, 4, 5, 8, 9, 10, 11, 12). Unlike alum or RIBI where a single injection caused inflammation at the site, repeated injections of IRX-2 into the same site did not result in significant inflammation at the site (unpublished observation). Booster immunizations with conjugate plus adjuvant (Days 14 and 28) were performed prior to assessing the DTH activity. Additional daily injections of IRX-2 were not given after the booster immunizations. When irradiated cells were used as the vaccine, the cells were suspended in either PBS or IRX-2 and injected subcutaneously using doses between $10^3$ and $10^5$ cells/mouse. The immunization schedule was identical to that used for the peptide conjugate vaccine.

In the comparative adjuvant studies in mice, the RAS (R 700=MPL+TDM in squalene/Tween 80) was reconstituted with 1 ml of PBS (as per the recommended protocol) and then mixed with 1 ml conjugate (1 mg/ml). Alum was mixed 1:1 with antigen. CpG oligonucleotides were mixed with the peptide conjugate following the published protocols for mice (100 ug conjugate with 20 ug CpG per mouse).

DTH Assay

In vivo antigen challenge for the DTH assay was assessed 9 days after the booster immunization. Mice received subcutaneous injections of the challenge antigen in the left footpad and PBS in the right footpad. The challenge antigen was either peptide (100 μg in 20 μl) or carrier (ovalbumin or KLH) (50 μg in 20 μg). After 24 hours, the right and left footpad thickness were measured using a digital readout caliper (Preisser DIGI-MET Model 18314, Stofiting Co, Wooddale, Ill.). The swelling response was calculated by subtracting the right footpad thickness (baseline) from the left footpad thickness (experimental response). The data are expressed as mean+/−standard error of the mean. Statistical analysis was via Student's t-test.

Antigen Stimulated IFN-γ Assay

Spleens were harvested 7-14 days after the second booster immunization and isolated by dispersing through a wire mesh screen. Adherent cells were obtained by taking spleen cells and allowing them to adhere to plastic for 90 minutes. The isolated adherent cells were added to the cultures to provide for additional antigen presenting cells ($6 \times 10^5$ lymphocytes per well were supplemented with $2 \times 10^4$ adherent cells). Release of IFN-γ by antigen-induced activation of lymphocytes was measured in supernatants harvested on day six using Duo-Sets ELISA reagents from R & D Systems (Minneapolis, Minn.).

Serum Antibodies to Carrier and Peptides

Serum was obtained between 7 and 21 days after the third booster immunization and frozen for later use in ELISA assays. ELISA plates (Immunolon-4, Nunc, Denmark) were coated with the antigen of interest (ovalbumin, KLH, conjugate or peptides) overnight. Dilutions of serum were added to the blocked and washed wells and incubated overnight. Biotin labeled anti-mouse IgG and avidin-alkaline phosphatase (Southern BioTech, Birmingham, Ala.) were added sequentially and following addition of pNPP substrate, the OD was measured and plotted vs the dilution of serum.

Results

IRX-2 Increases the Immune Response to a Whole-Cell Based Vaccine

Figure 31:
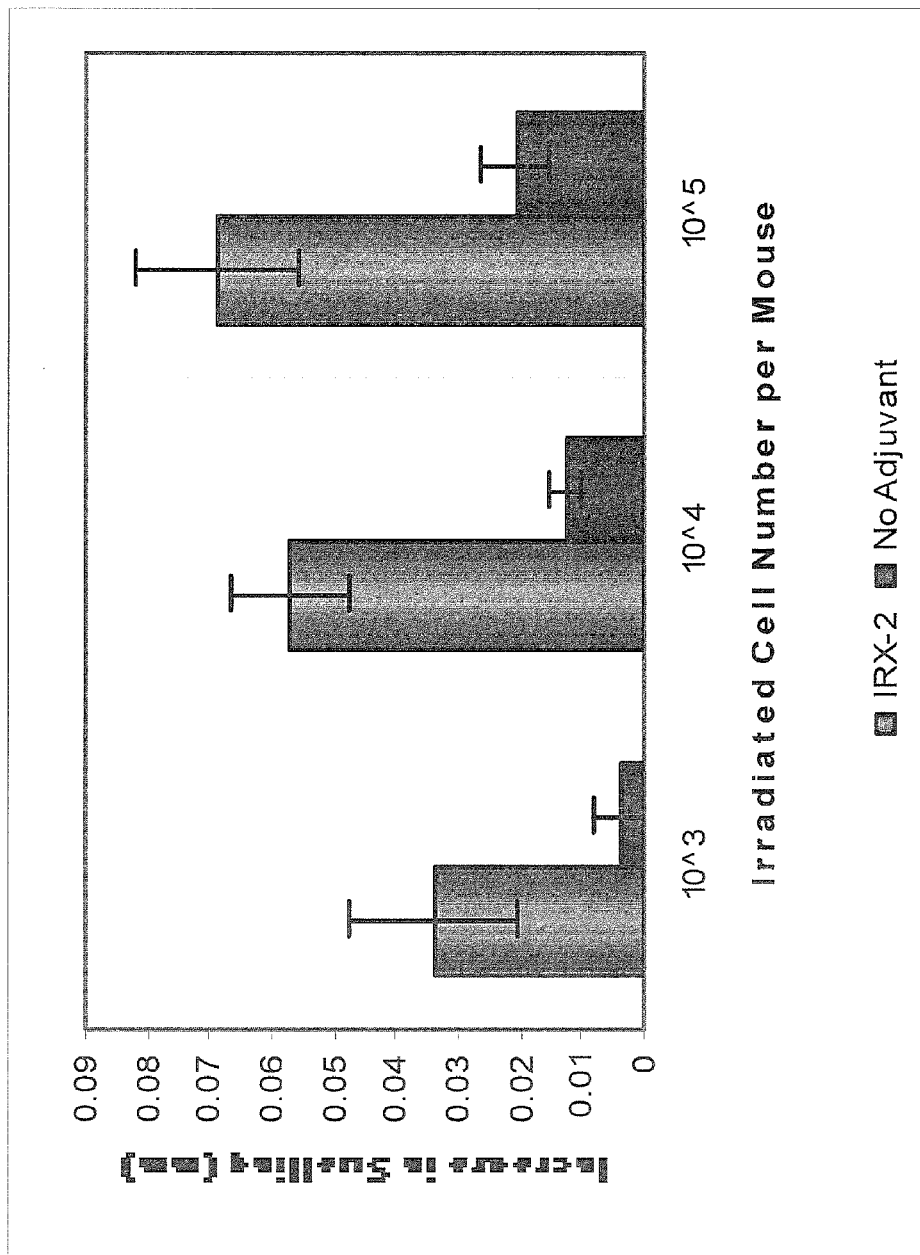
FIG. 31 is a bar graph of peptide-specific DTH responses of mice immunized with irradiated PSMA expressing 3T3 cells.

PSMA transfected 3T3 cells were used to immunize mice and confirm processing and presentation of the PSMA peptides. Immune response to the peptides was assessed by the Delayed Type Hypersensitivity (DTH) assay. As shown in FIG. 31, the irradiated PSMA expressing cells generated a DTH response in mice when challenged with the two PSMA peptides. Mice were vaccinated with doses of irradiated PSMA expressing 3T3 cells and either IRX-2 (blue) or no adjuvant (PBS, magneta) and the DTH response after peptide challenge was measured 9 days after the second booster immunization. The results are expressed as the average (+/−SEM) for the groups of 5-15 mice. The increase in footpad swelling was a function of the dose of the irradiated cells and IRX-2 administered as compared to the no adjuvant (PBS) mice. The determination of statistical difference between the IRX and no adjuvant (PBS) groups was assessed by Student's t-test. The two tailed significance was $=p<0.001$ for $10^4$ and $10^5$ cell/mouse and the one tailed significance was $p<0.05$ for $10^3$. The response was dose related and enhanced when the vaccine was administered with IRX-2 as compared to no adjuvant.

IRX-2 Enhancement of Peptide-Specific DTH in PSMA-Conjugate Immunized Mice: Dosing of Conjugate and IRX-2

Figure 32:
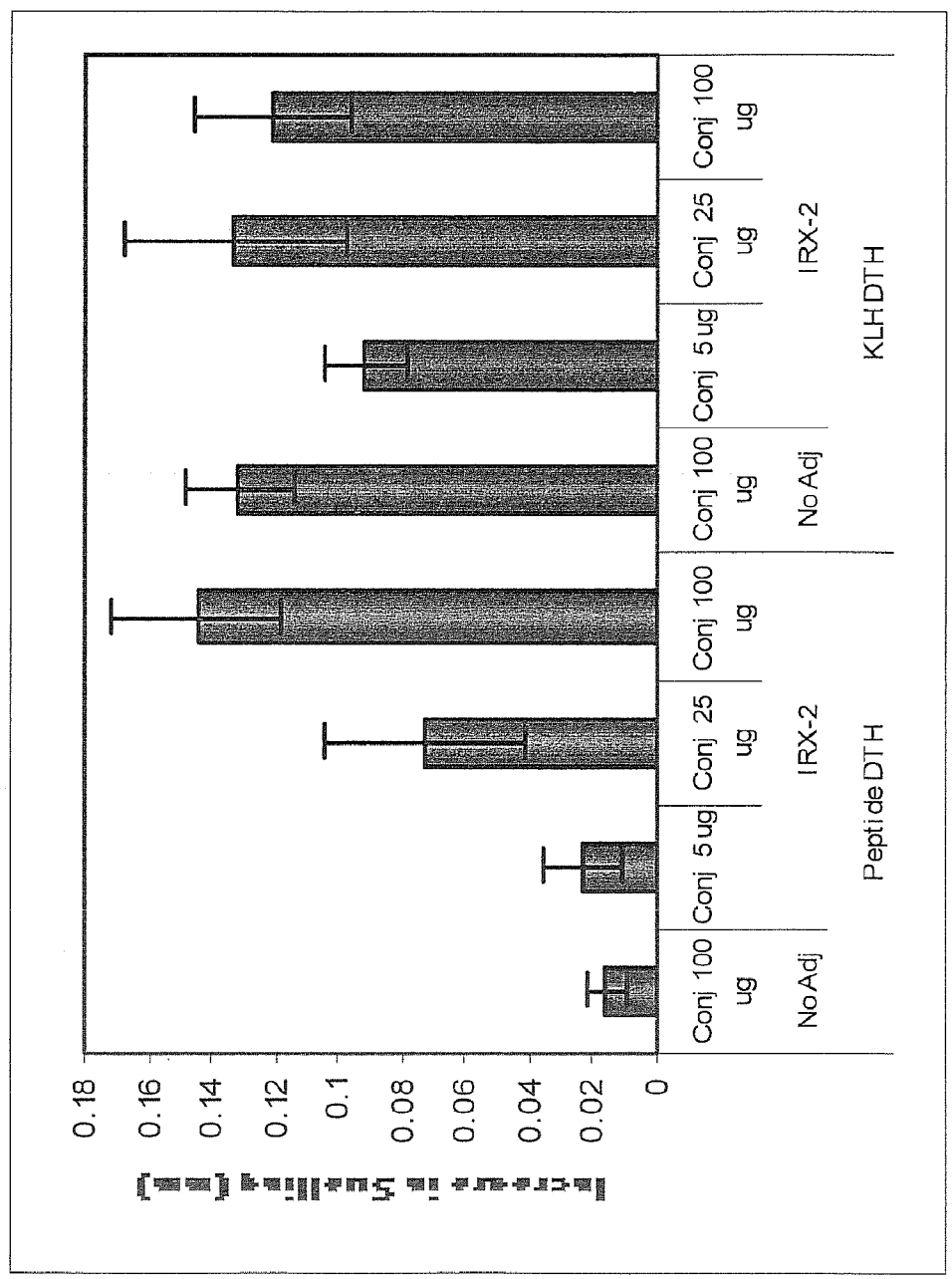
FIG. 32 is a bar graph showing peptide-specific DTH in PSMA-KLH versus no carrier.

Mice were immunized with varying doses of the peptides alone or peptides conjugated to the Keyhole Limpet Hemocyanin (KLH) carrier with and without IRX-2. The T cell response after peptide or conjugate challenge was assessed to define the optimal dose of antigen. There was a dose-dependent response for the peptide specific DTH response but the response to carrier was not influenced by the dose of conjugate (FIG. 32). FIG. 32 presents the DTH response of the immunized mice to the peptide (left side) or KLH (carrier; right side). The response is expressed as the mean+/−the SEM for 5-10 mice per group. No Adj indicates that the response was measured in mice immunized with optimal dose of conjugate and PBS. The peptide response was dose-related but the response to carrier was not. Differences from no adjuvant for peptide-specific response to PSMA-KLH conjugate doses of 100 ug and 25 ug were significantly different from no adjuvant at p<0.05 for Student's t-test. The highest dose of conjugate tested without adjuvant was not active in the peptide specific assay as compared to the KLH response, which was similar to the response with IRX-2. When peptides without conjugation were co-administered with IRX-2, no peptide-specific DTH response was observed (data not shown).

IRX-2 Increases Response to Antigen in a Dose-Dependent Manner

Figure 33A:
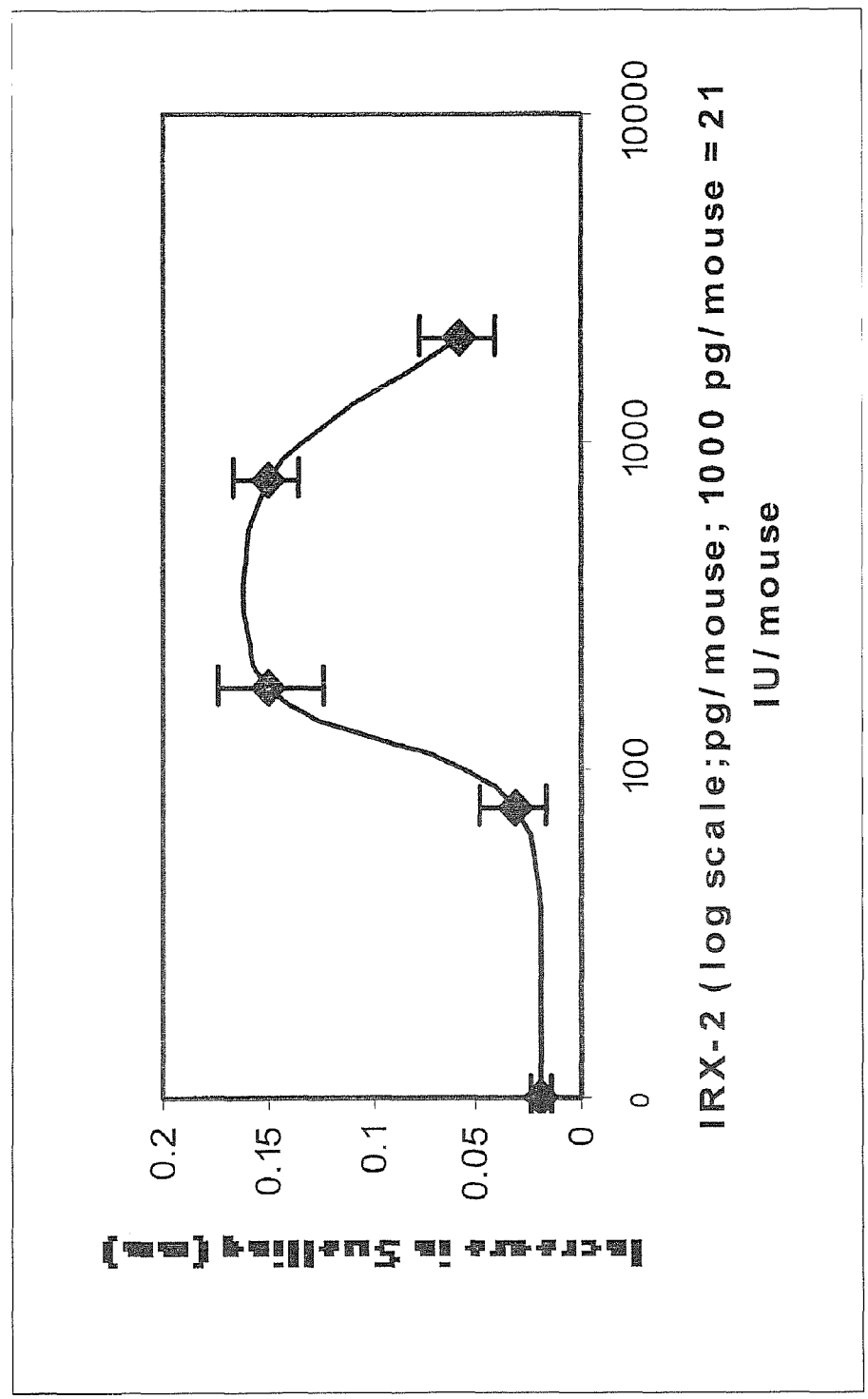
FIG. 33A is a graph showing IRX-2 increasing response to antigen in a dose-dependent manner.
Figure 33B:
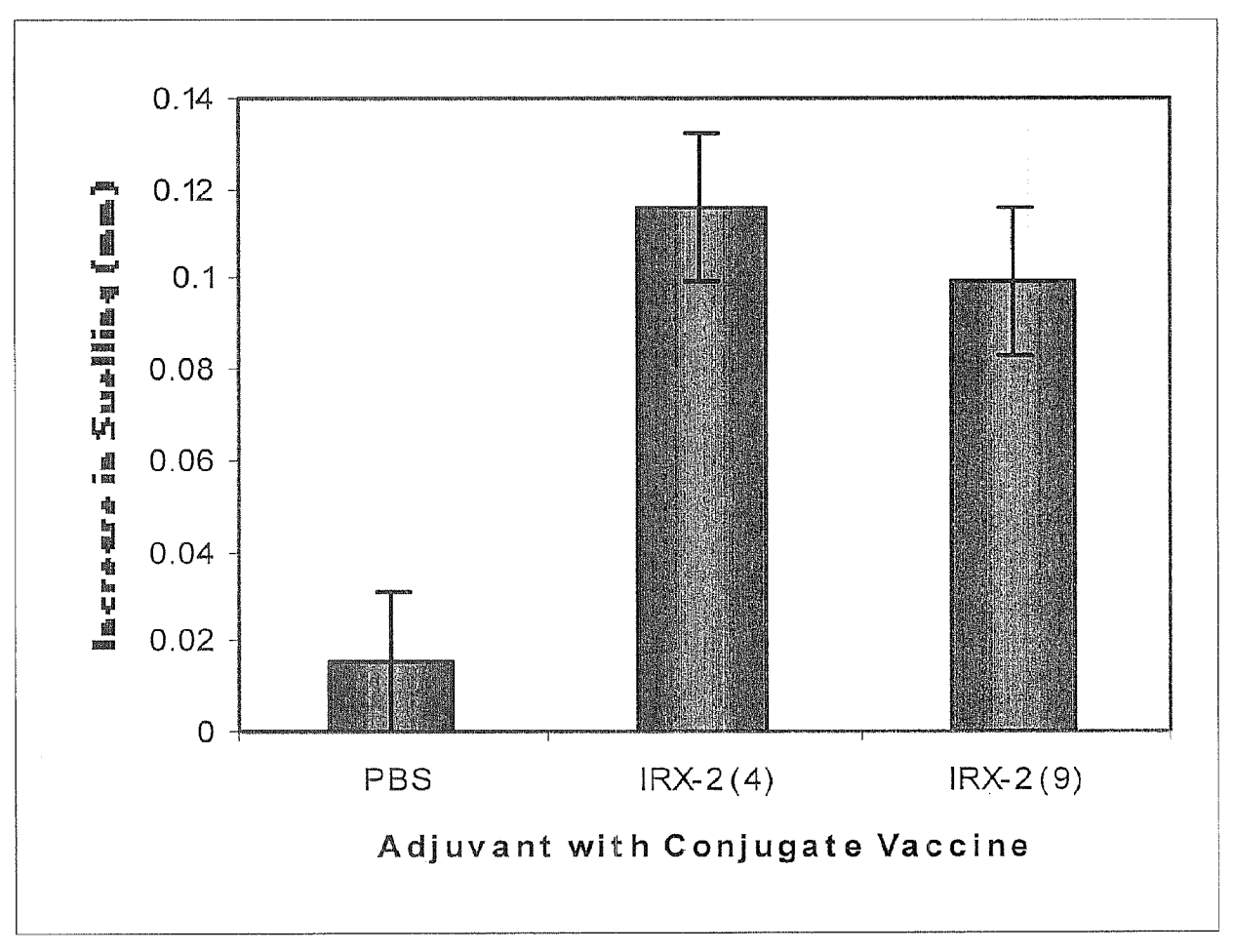

The dose of IRX-2 required to generate the optimal peptide specific DTH response was evaluated (FIGS. 33A and 33B). Mice were immunized with the optimal conjugate vaccine (100 ug/mouse) and various doses of IRX-2. Since IRX-2 contains multiple cytokines, the dose of IRX-2 is plotted as the concentration of IL-2 in IRX-2 per mouse. The concentration of IL-2 is represented by either two interconvertible measurement (IU=international units or pg/ml based on a pure recombinant standard). The T cell-specific peptide response was assessed by the DTH assay and is represented as the increase in swelling (+/−standard error of the mean) due to the peptide challenge. The difference between the response for the optimal doses (between 200 and 800 pg/mouse; 4-16 µl/mouse) was statistically significant (p<0.05 by Student's t test) from no IRX-2 (0) as well as the lowest dose (70 pg/ml) and highest dose (2100 pg/ml) tested in the assay. The dosing of IRX-2 was defined by the levels of IL-2 as measured by ELISA. Doses between 200 and 800 pg of IL-2 equivalents per mouse were effective in enhancing the T cell response in the DTH assay.

Multiple Injections of IRX-2 Improve Immune Response to Antigen

Either 4 or 9 additional injections of IRX-2 were similar with respect to enhancement of the peptide specific DTH but a single administration without the subsequent injections of the IRX-2 alone did not enhance the T cell specific response to antigen (FIGS. 33A and 33B and data not shown).

IRX-2 is Superior to Other Adjuvants in Mediating a T Cell Response to Antigen

Figure 34:
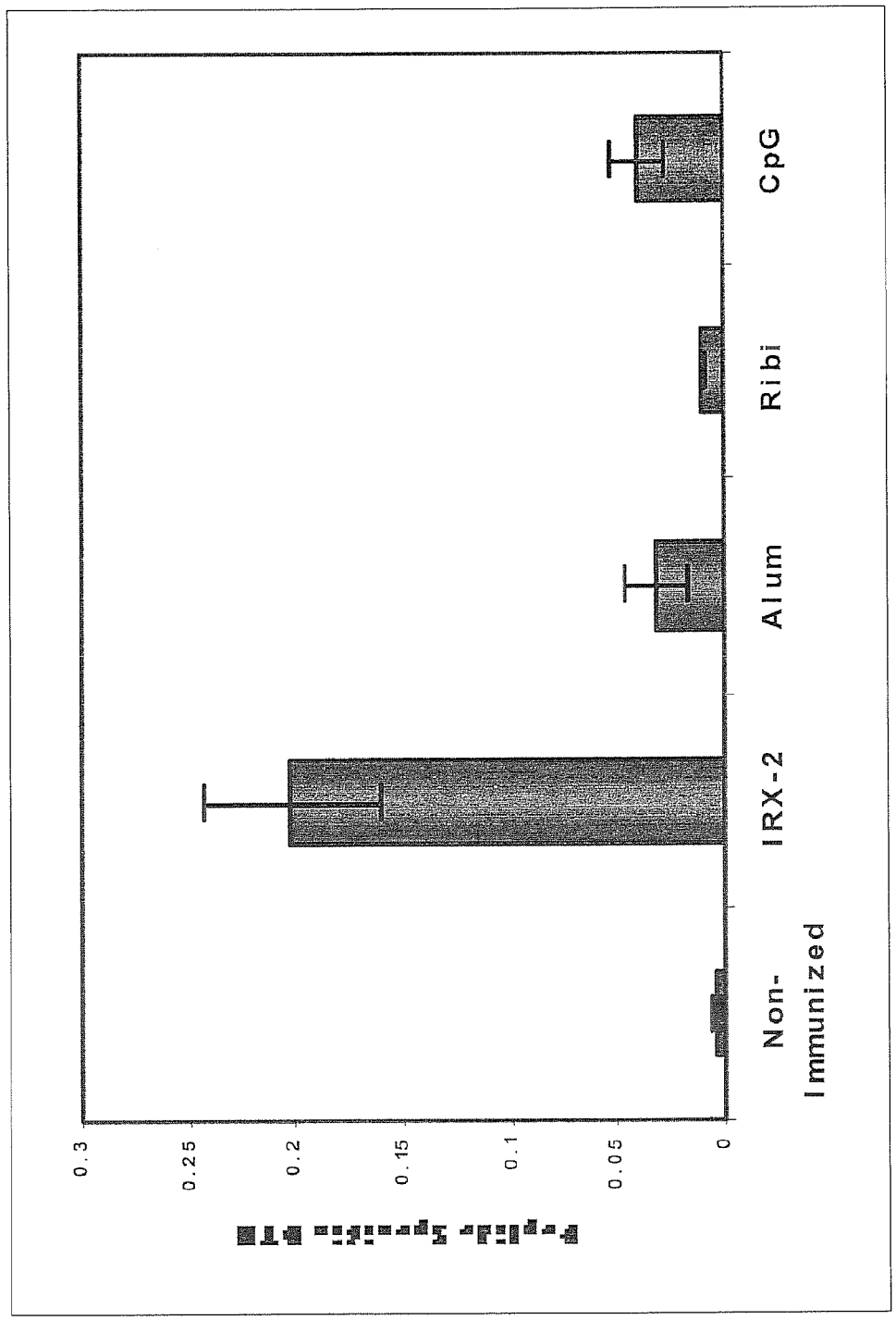
FIG. 34 is a bar graph showing DTH assay of PMSA peptide immunized mice injected with IRX-2 versus other adjuvants.

Three adjuvants with different mechanisms of action were selected for comparison to IRX-2. Alum (the adjuvant utilized in the majority of FDA approved vaccines), Ribi Adjuvant System (representative of adjuvants with oil and bacterial components) and CpG (representative of Toll-like receptor (TLR) activating adjuvants) were administered as per published protocols. IRX-2 enhancement of the T cell peptide-specific response was superior to either Alum, Ribi® or CpG adjuvants (FIG. 34). Mice were immunized with PSMA peptide conjugate and the indicated adjuvants. After two boosts (Day 14 and Day 28), the DTH assay was performed 9 days after the final boost. Results are expressed as the average increase in swelling for peptide injected vs. control paw. (+/−SEM). IRX-2 response was greater than all others at p<0.001 (Student's t test).

IRX-2 Increases IFN-γ Production in Response to Peptide Antigen

Figure 35:
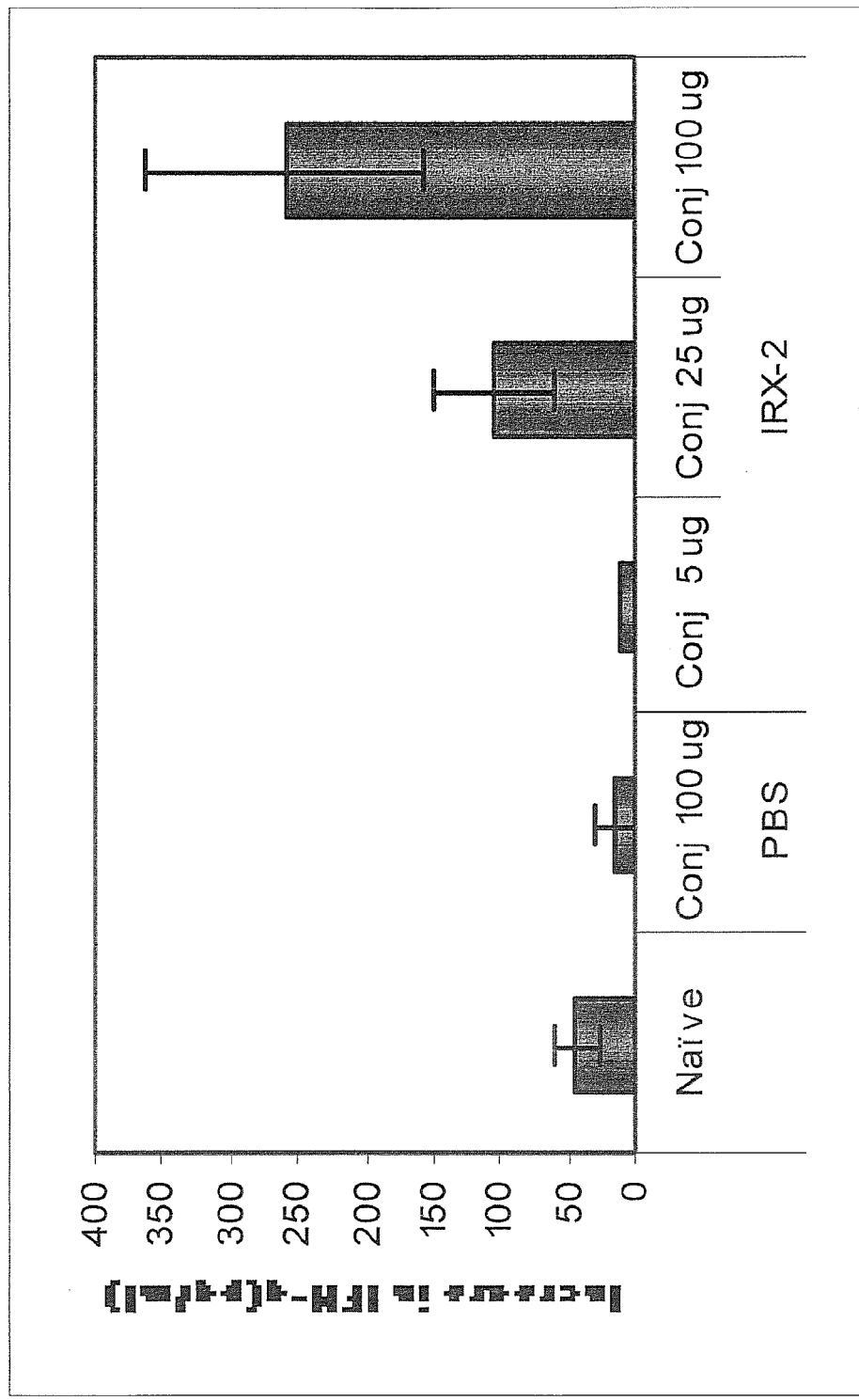
FIG. 35 is a bar graph of IFN-γ production in response to peptide antigen.

Mice were immunized with various doses of the KLH-PSMA conjugate and IRX-2. Spleen cells from immunized mice were evaluated ex vivo for response to stimulation by the peptides by measuring the secretion of IFN-γ. IRX-2 increased the peptide-specific secretion of IFN-γ by spleen cells and the response was dose-dependent with respect to the conjugate concentration used for immunization and the enhancement was significantly different from non-adjuvant treated mice ((PBS) FIG. 35). IFN-γ was measured in the supernatants after 6 days of culture and the results expressed as the average (=/−SEM) for the mice at a given dose of the conjugate vaccine. The increases for 25 and 100 ug conjugate were statistically significant (P<0.05) vs. the no adjuvant control (PBS). For comparative purposes, the lower panel represents the peptide-specific DTH response for similar doses of conjugate.

IRX-2 Enhances Antibody Response to Peptide Antigen

Figure 36:
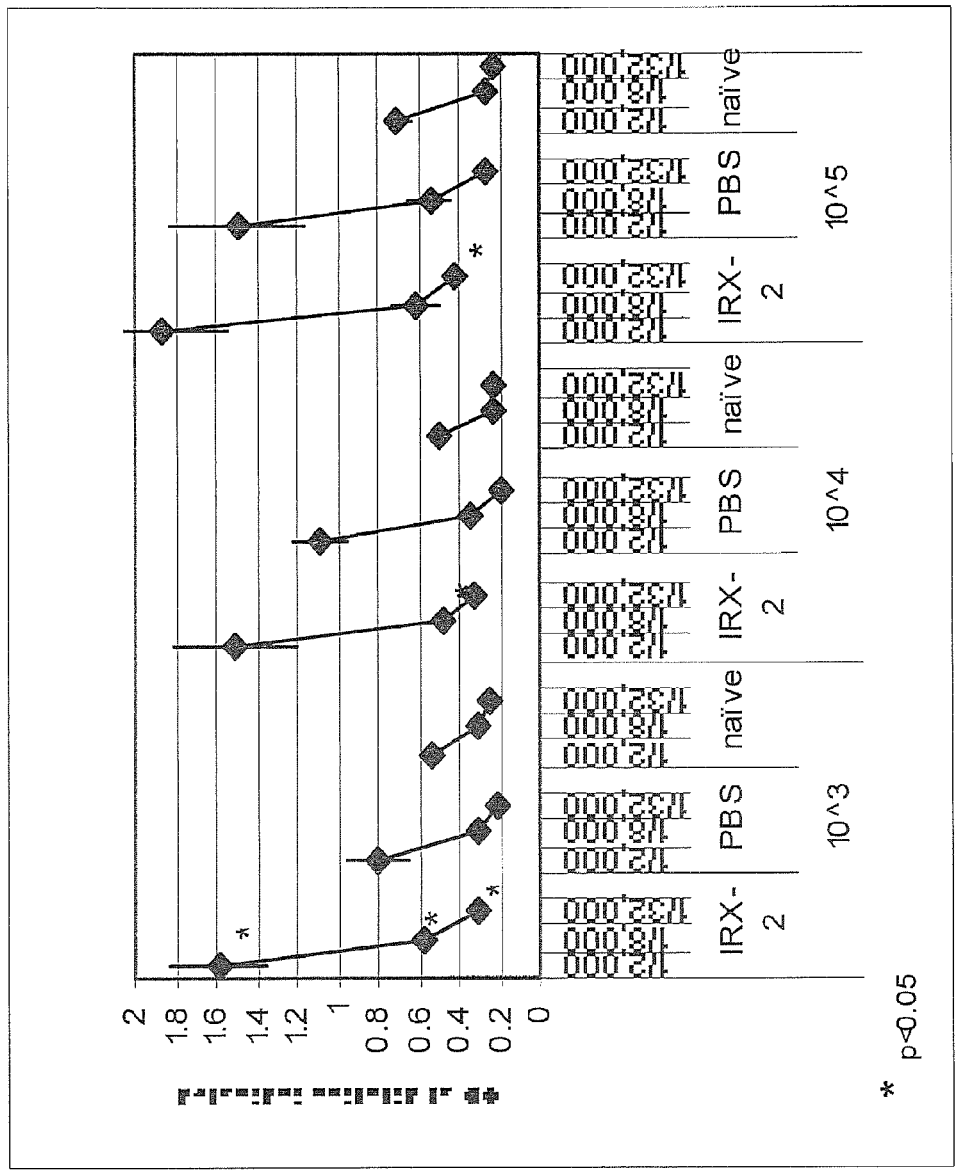
FIG. 36 is a graph of serum antibody responses.

Mice immunized with the irradiated cell-based vaccine show serum antibodies to the peptides and the antibody response of immunized mice was enhanced by IRX-2 at the lower doses of the vaccine (FIG. 36). Peptide-specific serum antibodies from mice immunized with irradiated cell vaccine. Serum antibody responses were measure as optical density at dilutions of serum using a mouse IgG-specific antibody in the ELISA assay as described in the methods. Mice immunized with vaccine plus IRX-2 have an enhanced peptide specific response when the vaccine dose was sub-optimal without adjuvant. The response was also significantly different with IRX-2 for lower serum dilutions at the higher vaccine doses. When the KLH-peptide conjugate vaccine was evaluated, IRX-2 also enhanced the peptide specific response compared to both alum and no adjuvant (data not shown).

Figure 37:
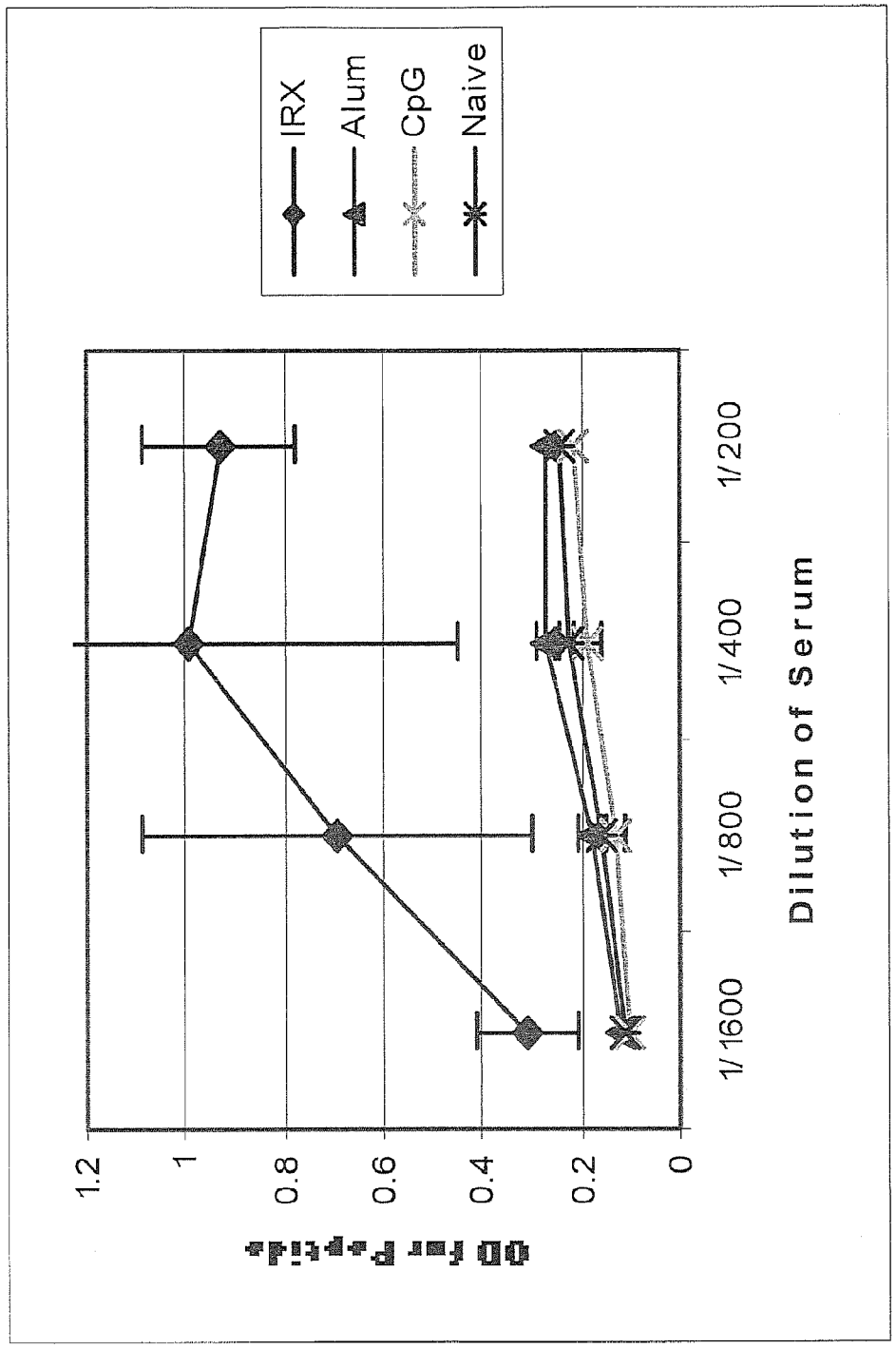
FIG. 37 is a graph of serum antibody response of IRX-2 versus other adjuvants.

IRX-2 Is Superior to Other Adjuvants in Stimulating an Antibody Response to Conjugated Peptides IRX-2 given with ovalbumin-peptide conjugates resulted in antibodies to the peptides while neither CpG nor alum given with the conjugate resulted in antibodies to the peptides (FIG. 37). The data is for the peptide with the sequence beginning with ALF and significance was p<0.05 by ANOVA for IRX-2 versus alum and CpG. These results are consistent with the T cell adjuvant comparison study where only IRX-2 given with the conjugate vaccine resulted in a peptide specific DTH response (see FIG. 34 for comparison).

Example 13

In the following study, IRX-2 was shown to amplify the T cell response to a dominant mouse epitope of PSMA in a vaccine including Incomplete Freund's adjuvant. IRX-2 enhanced the PSMA peptide-specific IFN-γ response of mice immunized with a PSMA peptide in Incomplete Freund's adjuvant. T cell-specific in vivo activity was confirmed by demonstrating the total increases in peptide-specific IFN-γ secretion by spleen cells harvested from immunized mice as well as the number of antigen-specific T cells. IRX-2 in contrast to other adjuvants also enhanced B cell responses to the peptides.

Materials and Methods

Reagents and Cells

The NFT peptide used in these studies was synthesized by BioSynthesis Inc (Lewisville Tx). The NFT peptide sequence was NFTQIPHLAGTEQNF (SEQ ID NO: 17) which is from the human protein. The mouse PSMA has a similar sequence (NFTRTPHLAGTQNNF, SEQ ID NO: 18) but the non-identity as indicated by the non-bold amino acids, means that these studies are not specifically designed to demonstrate breaking of tolerance. The negative control immunization peptide for these studies was a class II influenza epitope for C57b1/6 mice (NGSLQCRICI, SEQ ID NO: 19). Ovalbumin, Incomplete Friends Adjuvant (IFA), and the combination adjuvant (MPL+TDM in squalene/Tween 80, also called Ribi Adjuvant System or Sigma Adjuvant System Catalogue Number 86322) were purchased from Sigma (St Louis, MO). The combination adjuvant consisted of Monophosphoryl Lipid A (MPL; 0.5 mg) and synthetic Trehalose Dimycolate (TDM; 0.5 mg), and 44 ul squalene and 200 ul of Tween-80 in a final volume of 1 ml of PBS (ie oil in water). Freund' Incomplete Adjuvant consists of paraffin oil combined with mannide monooleate (0.85 mL paraffin oil and 0.15 mL mannide monooleate). The adjuvant was selected because it is commercially available and is similar to Freund's complete adjuvant but without the toxicity.

Immunization

Balb/c female mice (6-8 weeks of age) were purchased from either Charles River Laboratories (Wilmington, Mass.) or Harlan Laboratories (Indianapolis, Ind.) and were housed under the care of the Cold Spring Harbor Laboratory (CSHL) Animal Facility (Animal Welfare Assurance certificate number A3280-01). All procedures were approved by the ALAC committee of the CSHL. Immunizations (200 ul/mouse typically containing 100 ug of antigen with 100 ul adjuvant, PBS or X-Vivo 10 media) were given subcutaneously at the base of the tail to provide for rapid draining to the regional lymph nodes. Except where noted, nine additional injections of IRX-2 also at the base of the tail followed the primary immunization (designated as Day 0) so IRX-2 without antigen was administered on days 1, 2, 3, 4, 7, 8, 9, 10, 11. Mice not receiving the IRX-2, received either PBS or X-Vivo 10 media on days 1, 2, 3, 4, 7, 8, 9, 10, 11 to control for potential stress in handling the mice. Both PBS and X-Vivo, when administered with antigen, were non-stimulatory compared to IRX-2. In the text and figures, the mice receiving antigen plus PBS or X-Vivo are referred to as "control" or no-adjuvant mice. Dosing is defined based on the IL-2 levels in IRX-2 and unless otherwise indicated was 700 pg/mouse (15 IU/mouse). Booster immunizations with antigen plus adjuvant were given on day 14 and for the DTH assay repeated on 28. Additional daily injections of IRX-2 were not given after the booster immunizations. When irradiated cells were used as the vaccine, the cells were suspended in either PBS or IRX-2 and injected subcutaneously using doses between $10^3$ and $10^6$ cells/mouse.

The IFA was mixed as 1 part peptide (1 mg/ml), 1 part IFA, and 1 part of either IRX-2 or PBS/X-VIVO. After emulsifying by passage through a female: female leur-lok connecting two syringes, each mouse received 300 ul subcutaneously. The combination adjuvant (MPL+TDM in squalene/Tween 80 was reconstituted with 2 ml of PBS (as per the recommended protocol) and then mixed with 2 ml conjugate (1 mg/ml) and 2 mls of either IRX-2 or control. The combination adjuvant was mixed with IRX-2 by vortexing and each mouse received 300 ul subcutaneously to account for the additional volume of the IFA.

Antigen Stimulated IFN-γ Assay

Lymph nodes and spleens were harvested at the times indicated (3-24 days after the first booster immunization) and cells isolated by dispersing through a wire mesh screen. Red cells in the spleens were lysed using ammonium chloride lysing buffer (Quality Biological Inc, Gaithersburg, Md.)). Adherent cells for addition to the lymph node cell cultures were obtained by plating spleen cells and allowing them to adhere to plastic for 90 minutes. The isolated adherent cells were added to the cultures to provide for additional antigen presenting cells (2-6×$10^5$ lymphocytes per well were supplemented with 2-4×$10^4$ adherent cells). Release of IFN-γ by antigen-induced activation of lymphocytes was measured in supernatants harvested on day six using Duo-Sets ELISA reagents from R & D Systems (Minneapolis, Minn.).

ELISpot Assay

Cells were plated at either 2×$10^5$ lymphocytes per well for spleen cells or 3×$10^5$ lymphocytes per well for lymph node cells. ELISpot plates (Millipore, Billerica, Mass.) were coated with capture antibody (MAB-18 from MabTech (Mariemont, Ohio) in PBS overnight. Plates were washed, antigen and cells added and then incubated for 18 hrs at 37° C. Wells were vigorously washed with PBS to remove cells and biotinylated second antibody (MabTech) added for additional 18 hr incubation. Plates were developed using sequential biotin-AP and DAB substrate. Plates were read using a microscope with digital conversion software by ZellNet (Fort Lee, N.J.)

Results

T Cell Peptide Immunization in IFA to Define IRX-2 Activity

Figure 38:
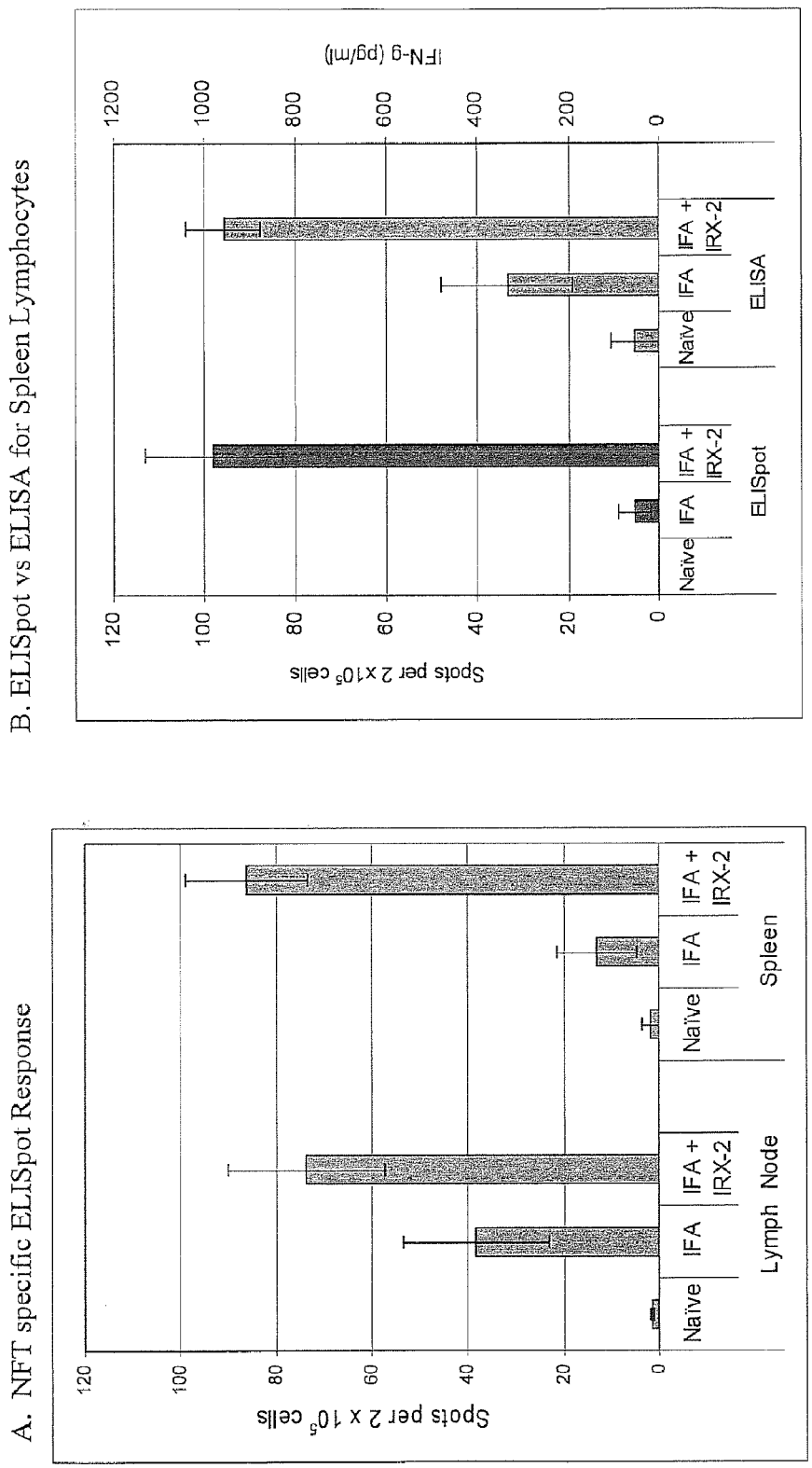
FIG. 38A is a graph of the number IFN-γ producing T cells in response to peptide antigen.
FIG. 38B is a graph comparing the number of IFN-γ producing cells versus the total production of IFN-γ in response to peptide antigen.
Figure 39:
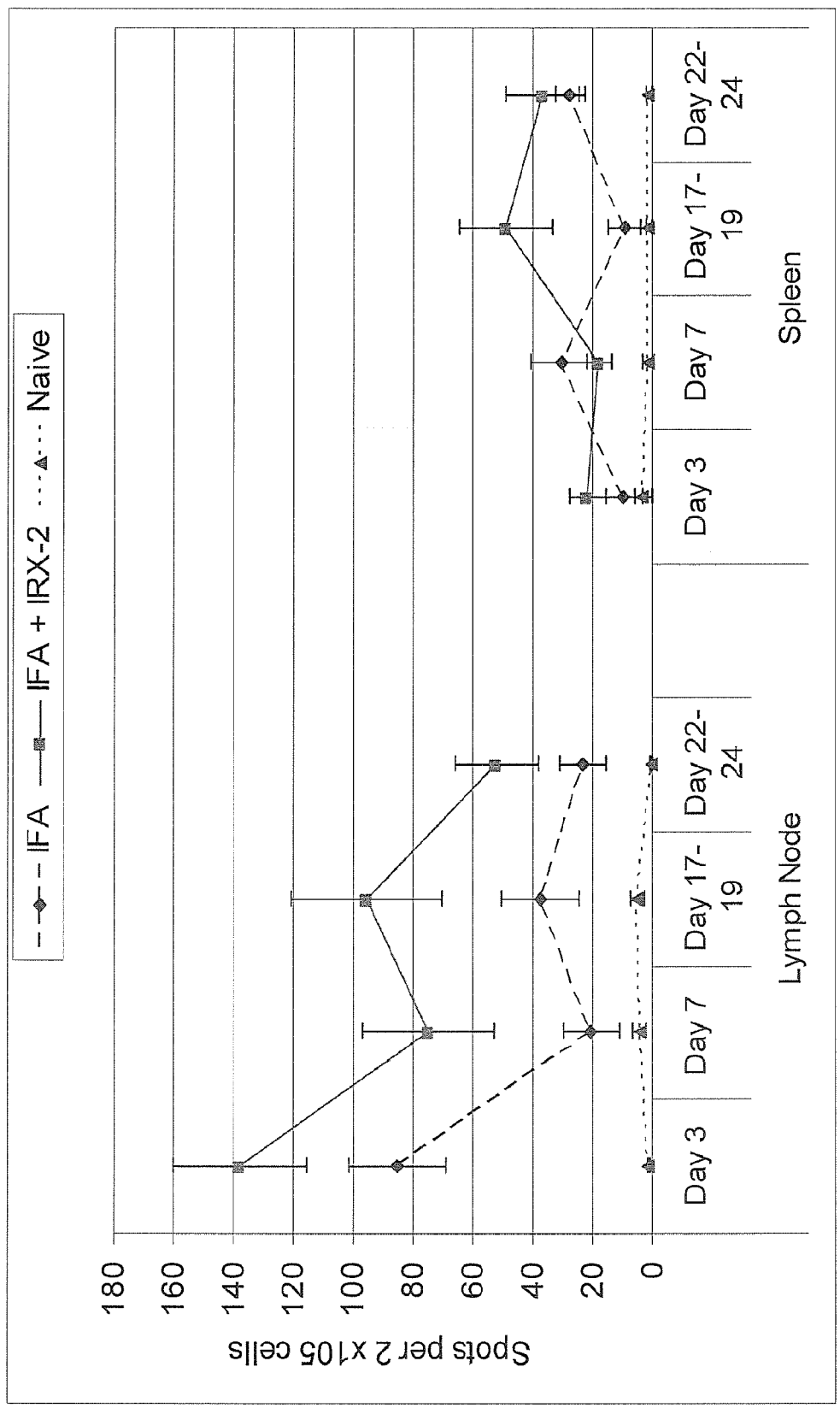
FIG. 39 is a graph of the kinetics of IFN-γ production in response to peptide vaccination.
Figure 40:
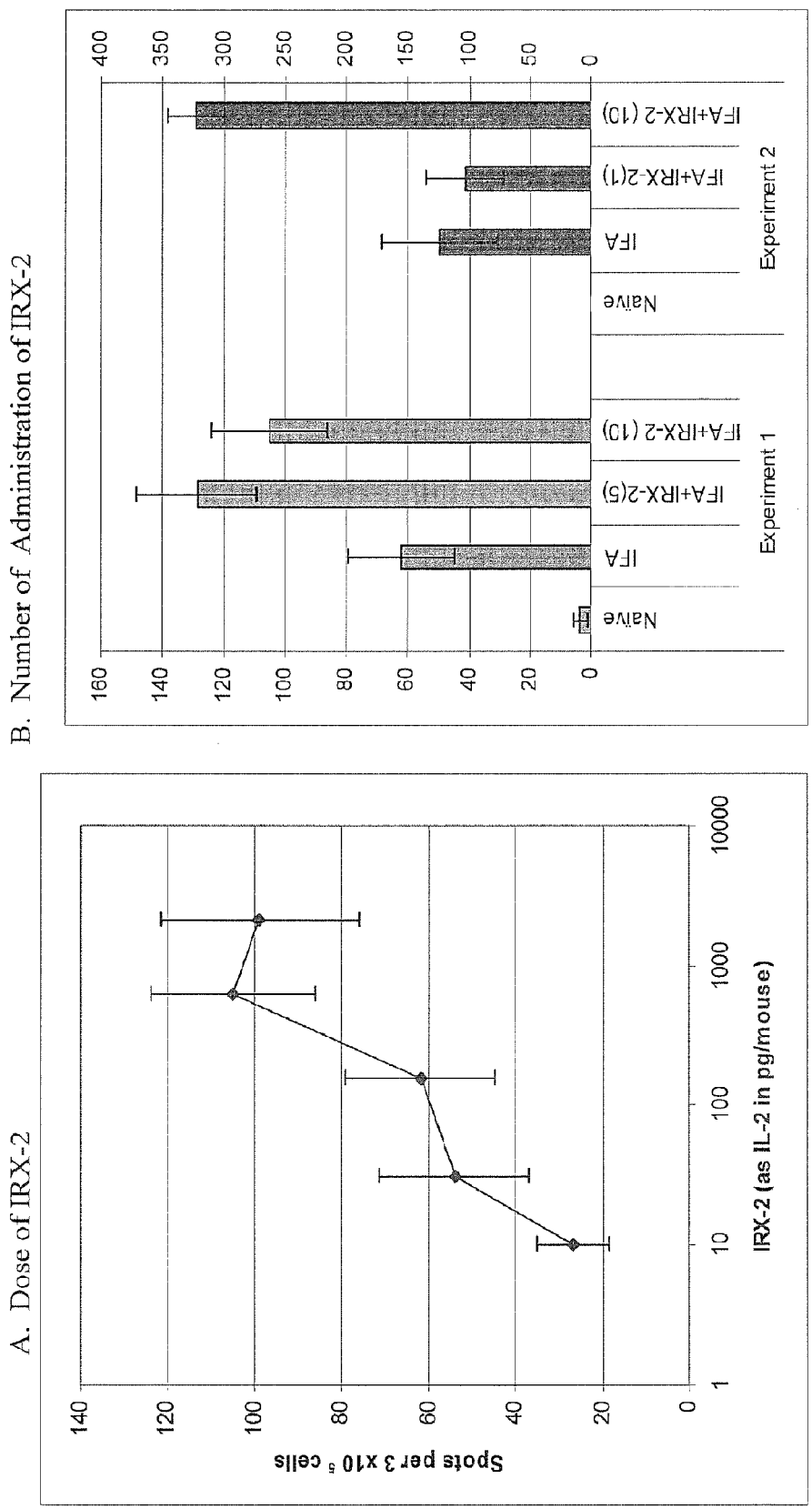
FIG. 40A is a graph of the dose response IFN-γ production in response to peptide vaccination.
FIG. 40B is a graph of the number of IFN-γ producing cells after different administrations of IRX-2

T cell responses to dominant peptide epitopes of protein antigens are typically evaluated by administering the peptides in Incomplete Freund's Adjuvant (IFA). IFA is effective as a result of its depot effect and its potential to generate inflammatory reactions at the site. Mice immunized with the dominant NFT peptide in IFA, mounted an immune response that was enhanced by treatment with IRX-2 as measured by the ELISpot assay for lymph node and spleen cells (FIG. 38A). Peptide without IFA with or without IRX-2 was not significantly different from naïve mice (data not shown). FIG. 38B confirms that the IRX-2 induced increase in spleen cell ELISpot response was also reflected in the IFN-γ secretion assay. FIGS. 39A and 39B presents the temporal development of the T cell response as defined by the ELIspot assay of cells harvested from mice over time following the booster immunization. IRX-2 increases the immune response compared to antigen only control in the lymph node at all time points. In the spleen cells, the response was enhanced only on days 17-19. The ELISpot assay with NFT in IFA was also used to measured the optimal dosing of IRX-2. As shown in FIG. 40A the optimal dose of IRX-2 was 700 pg of IL-2 equivalents/mouse administered daily for 10 days. Using the optimal dose both 9 and 4 additional doses of IRX-2 were found to be similar (FIG. 40B). A single administration of IRX-2 is not sufficient to enhance the T cell response (FIG. 40B). Similar results were obtained using peptide-conjugates as the immunogen in both the ELISpot and DTH assays (data not shown).

IRX-2 Preferentially Enhances T Cell Responses

Figure 41:
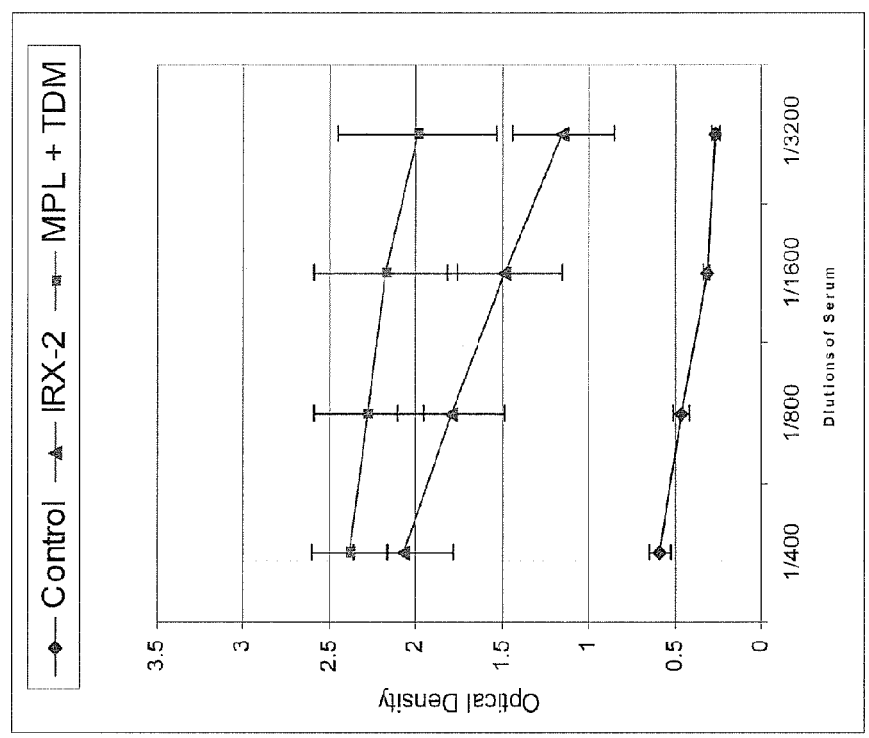
FIG. 41A is a graph of IFN-γ production after vaccination with IRX-2 versus other adjuvants.
FIG. 41B is a graph of antibody response after vaccination with IRX-2 versus other adjuvants.
Figure 41:
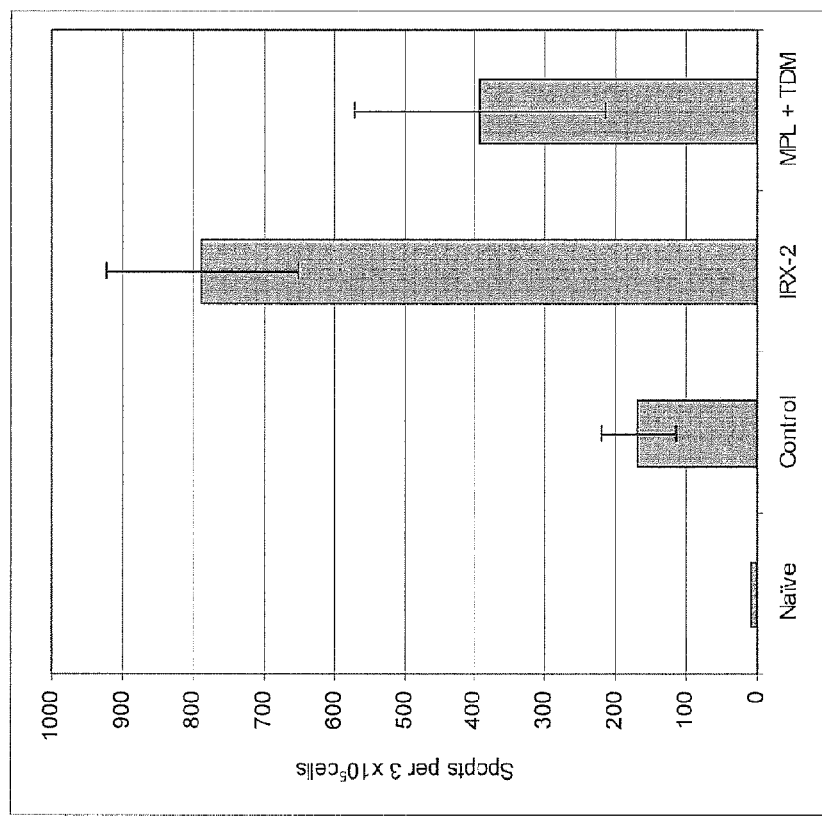

IRX-2 was compared to a commercially available combination adjuvant (MPL+TDM+squalene+Tween 80) using NFT peptide-conjugates and evaluated by measuring the T cell response to NFT and the B cell response to ovalbumin or KLH, which were used as the carriers. The MPL+TDM based adjuvant is commercially available from SIGMA and is similar to the RIBI adjuvant previously available from RIBI Adjuvant Company and subsequently sold by Sigma Chemical Company. The adjuvant is considered to be the prototypic example of a strong adjuvant since it is equivalent to the classis Freund's adjuvant but without the toxic side effects. The antibody titer to KLH at the 100 ug/ml dose used with the conjugate was not increased by the adjuvant due to the powerful activity of KLH (data not shown). For these studies, the response to ovalbumin was used to assess the B cell activity of the adjuvants. The increase in the T cell response for the NFT-conjugate on day 3 post booster immunization was positive for IRX-2 and the combination adjuvant (FIG. 41A) although IRX-2 was superior to the combination adjuvant. Conversely, IRX-2 enhanced the B cell response but it was not as effective as the combination adjuvant with respect to antibody titers in serum (FIG. 41B).

Prophylactic Tumor Vaccine Studies

Figure 42:
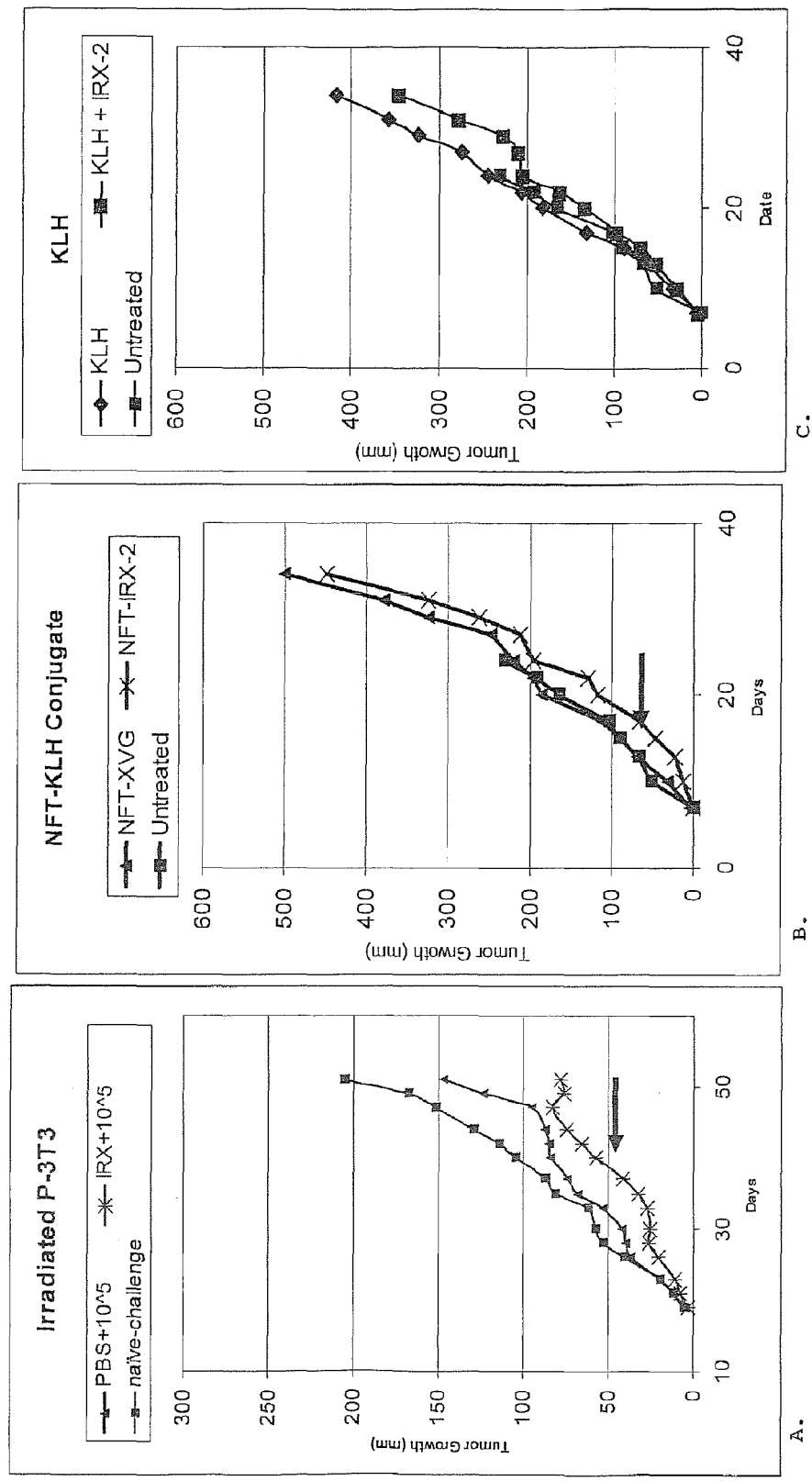
FIG. 42A is a graph of tumor growth after prior immunization with IRX-2 and a whole cell vaccine.
FIG. 42B is a graph of tumor growth after prior immunization with IRX-2 and a peptide-conjugate vaccine.
FIG. 42C is a graph of tumor growth after prior immunization with IRX-2 and the conjugate alone.

Previous studies demonstrated that mice immunized with a higher dose of irradiated hPSMA expressing 3T3 cells (P-3T3) than used in our studies were protected from tumor challenge with PSMA expressing RENCA cells (P-RENCA) as compared to mice immunized with 3T3 cells containing the neo-vector only. We confirmed and extended these studies using hPSMA expressing 3T3 cells with or without IRX-2 treatment and subsequently challenging with P-RENCA cells. As previously reported, mice that were immunized with a high dose of cells (>$10^6$ cells/mouse) were completely protected even without adjuvant (data not shown). Mice immunized with a lower dose $10^5$ cells/mouse had delayed tumor growth and IRX-2 enhanced the protection (FIG. 42). There was improved survival with IRX-2 but only a few mice failed to develop tumors in the IRX-2 group. To asses whether the dominant epitope was protective, mice were immunized with NFT-KLH conjugate (with or without IRX-2). A set of control mice was immunized with KLH only (with or without IRX-2). As shown in FIG. 42A-C, mice immunized with NFT-KLH plus IRX-2 had early delay in tumor growth as compared to the other three groups (NFT-KLH with no adjuvant or KLH with or without IRX-2. No mice completely rejected the tumor and the early protection as defined by tumor growth, did not translate to increased survival.

Figure 43:
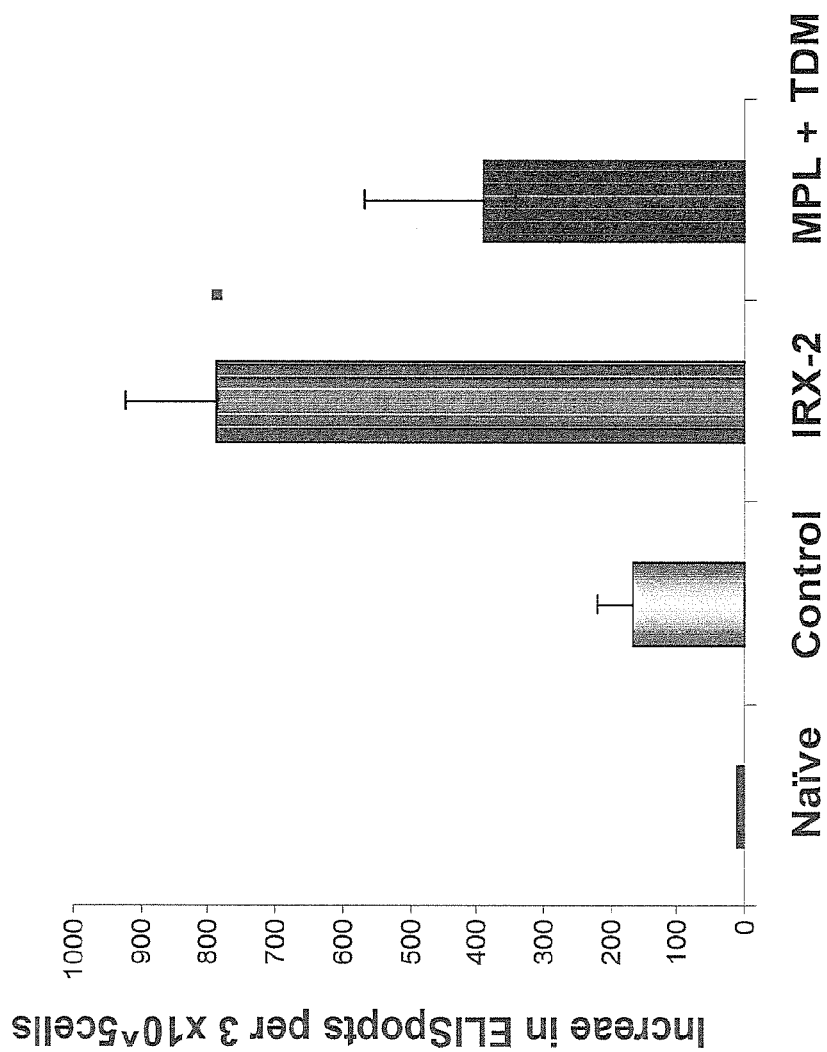
FIG. 43 is a graph of IFN-γ production of T cells after vaccination with IRX-2 and other adjuvants.

IRX-2 is Superior to Other Adjuvants in a Peptide Conjugated Vaccine System 8-10 week old mice (5-8 per group) were immunized with the NFT-KLH conjugate and either IRX-2, a combination adjuvant Monophosphoryl lipid A (MPL)+trehalose dicornymycolate (TDM) in squalene/Tween 8 or control. The NFT specific ELISpot response was measured using lymph node cells obtained 3 days after the booster immunization. As shown in FIG. 43 was superior to the MPL and TDM vaccine in enhancing in vivo antigen-specific T cell responses, as measured by IFN-γ secreting cells. The data is expressed as the increase in NFT specific ELISpots (mean+/−SEM)

Example 14

Development of subunit vaccines consisting of defined antigens derived from infectious organisms or tumors has been greatly hampered by the lack of effective CD8 T cell and Th1-inducing adjuvants. These responses collaborate to mediate effective cell-mediated immunity, resulting in the elimination of infected or malignant host cells. Indeed, most vaccines in current use still consist of live attenuated organisms, which can be difficult to manufacture and have potential safety and storage issues. Adjuvants such as mineral oil, mycobacteria, and alum are frequently required to amplify acquired immunity. The most effective is generally considered to be CFA, which can only be used in animals and can cause damaging skin inflammation. These studies described below, demonstrate IRX-2 added to a multi-adjuvant vaccine consisting of TLR-dependent and independent adjuvants induces extremely high levels of antigen-specific T cell immunity.

The following example demonstrates that IRX-2 enhances peptide vaccines in combination with other adjuvants that work by both TLR-dependent and independent mechanisms. Furthermore IRX-2 enhanced the number of antigen specific T cells in vivo after vaccination with a multi-component vaccine as well the cytotoxic activity of the antigen specific T cells.

Materials and Methods

Adjuvant Combinations and Vaccination Procedures

C57BL/6 or BALB/c mice (Harlan) were immunized intradermally (i.d.) with combinations of the following reagents in PBS (per mouse): OVA257-264 (SIINFEKL) peptide (100 µg; ProImmune), IFN-γ (100 ng, Peprotech), monophosphoryl lipid A (MPL) plus trehalose 6,6'-dimycolate (TDM) emulsion (Ribi adjuvant, used as per manufacturer's instructions; Sigma-Aldrich), CpG 1826 (25 µg; VH Bio), polyinosinic: polycytidylic acid (polyI:C; 50 µg; Sigma-Aldrich), MPL (50 µg; InvivoGen), Final vaccine volumes were 200 µl (100 µl/flank); vaccines were warmed to 37° C. and shaken vigorously before injection. Mice were primed on day 0 and boosted on days 9-11 with the same doses of Ag/adjuvant unless otherwise indicated. Combined adjuvants containing MPL plus TDM, an additional TLR agonist, IFN-γ, and either anti-CD40, class II peptide, or whole protein are referred to as the combined adjuvant for synergistic activation of cellular immunity (CASAC). Blood samples were taken for pentamer analysis on days 19-21 unless otherwise indicated. In vivo CTL assays were performed on days 20-22, unless otherwise indicated.

In Vivo Cytotoxicity Assays

Splenocytes from unprimed C57BL/6 mice were pulsed with 10 μg/ml antigenic peptide in culture for 1 h. These cells were then washed twice in PBS and labeled with 0.3 μM CFSE for 10 min. Control cells were cultured in medium alone and labeled with 3 μM CFSE. Control and target cells ($10^7$ each) were mixed and transferred i.v. into immunized or control recipients. Eighteen hours later we harvested spleens and analyzed CFSE by flow cytometry. Numbers of target (CFSElow) vs control (CFSEhigh) cells recovered were used to calculate the percentage of killing with the following formula: killing (%)=1−[(no. of targets/no. of control cells in immunized animal)/(no. of targets/no. of control cells in control animal)]×100.

Results

IRX-2 Synergizes with Other Adjuvants in Peptide Vaccines

Figure 44:
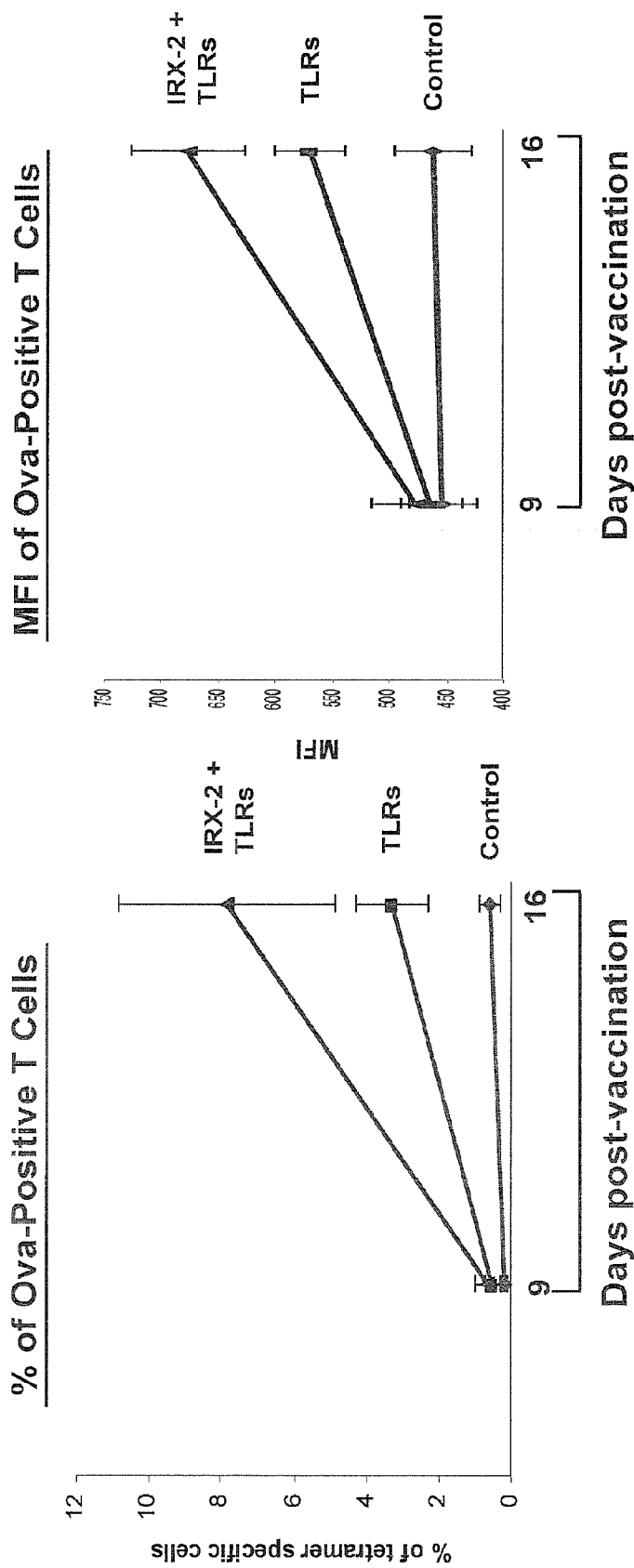
FIG. 44 is a graph of antigen specific cells after vaccination with IRX-2 and other adjuvants.

As shown in FIG. 44, IRX-2 in combination with a multi-adjuvant preparation (CpG, poly I:C, IFN-g in and oil emulsion) is superior to the adjuvant combination alone in creating antigen specific T cells. The percentage of antigen-specific T cells after vaccination as shown in FIG. 44A was increased when IRX-2 was added to the vaccine. Furthermore the number of antigen-specific MHC molecules per T cell was increased when IRX-2 was added to the vaccine as shown in FIG. 44B.

IRX-2 increases the cytotoxicity of antigen specific T cells when added to a peptide vaccine containing TLR-dependent and independent adjuvants.

Figure 45:
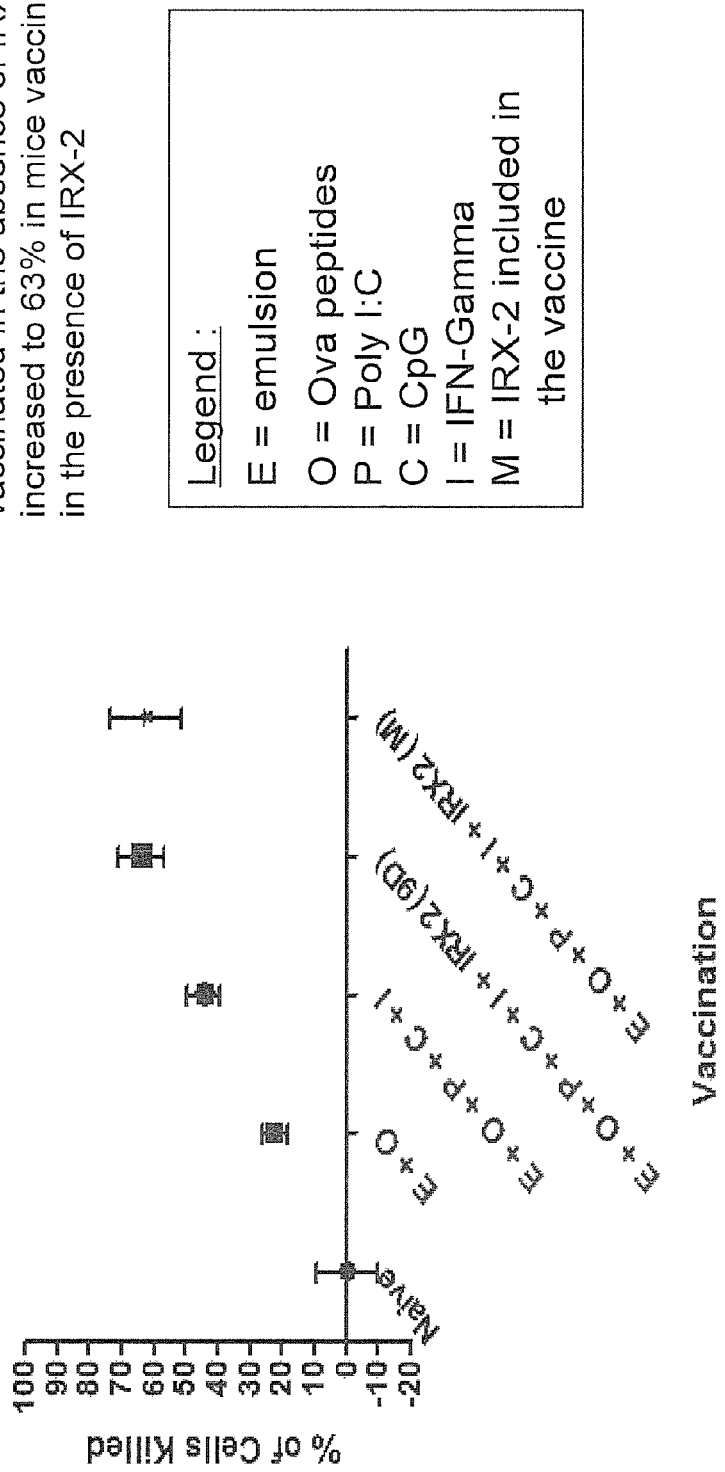
FIG. 45 is a graph of in vivo cytotoxicity after vaccination with IRX-2 and other adjuvants.

As shown in FIG. 45, IRX-2 in combination with a multi-adjuvant preparation (CpG, poly I:C, IFN-γ in and oil emulsion) is superior to the adjuvant combination alone in enhancing the cytotoxic activity of the antigen specific T cells that were created by vaccination with the vaccine. Furthermore, it was shown in FIG. 45 that when IRX-2 was added to the multi-adjuvant vaccine only a single injection was needed.

Example 15

IRX-2 Enhancement of the Immune Response to Ovalbumin Expressed by a Canary Pox Viral Vector (ALVAC)

The following example demonstrates the ability of IRX-2 to enhance the T cell responses to an antigen expressed in a viral-based vaccine. Furthermore, IRX-2 was shown to enhance T cell responses to a viral based that was further enhanced with TRICOM, a triad of stimulatory molecules.

VA-ALVAC is a canary pox virus that has been "engineered" to express ovalbumin protein. A putative advantage of the construct is that the virus should generate an "inflammatory response" which eliminates the need for a TLR adjuvant. OVA-ALVAC infects all cells at the site, including antigen presenting cells (DC's) which provides for presentation of processed antigen without a cross-presentation requirement. Lymph Nodes draining the site receive both the ovalbumin secreted by the infected cells and the DC's that have migrated from the site of inflammation. The APC entering the node are the primary driver of the T cells (Thelper and T cytotxic) and the ovalbumin draining from the site to the node is required to generate the Antibody producing cells. Two different ovalbumin expressing constructs were available for evaluation: OVA-ALVAC and OVA-TriCom-ALVAC. The TriCom construct was engineered to express LFA-1, ICAM-1 and B7.1 in addition to ovalbumin. These three proteins are hypothesized to enhance the immune response by providing for over-expression of important co-stimulatory proteins.

Materials and Methods

The model for evaluating the immune response was primary immunization followed by a booster immunization on day 14, 1RX-2 was delivered with the ALVAC constructs on both days. Additional IRX-2 was administered for 9 days following the primary immunization. Mice were sacrificed or bled on the days indicated in the figures accompanying this report. Three doses of OVA-ALVAC were used in the study ($3\times10^7$(standard dose), $3\times10^6$, $3\times10^5$, PFU per mouse). Two doses of OVA-TriCom-A ALVAC— were also evaluated in the study ($3\times10^5$(standard dose) and $3\times10^5$ PFU per mouse). The T cell response in lymph nodes and spleens was measured by ELISpot using the mouse dominant epitope (SIINFEKL, SEQ ID NO: 20). The B cell response was measured by ELISA using ovalbumin coated plates and serum from immunized mice.

Results

Figure 46:
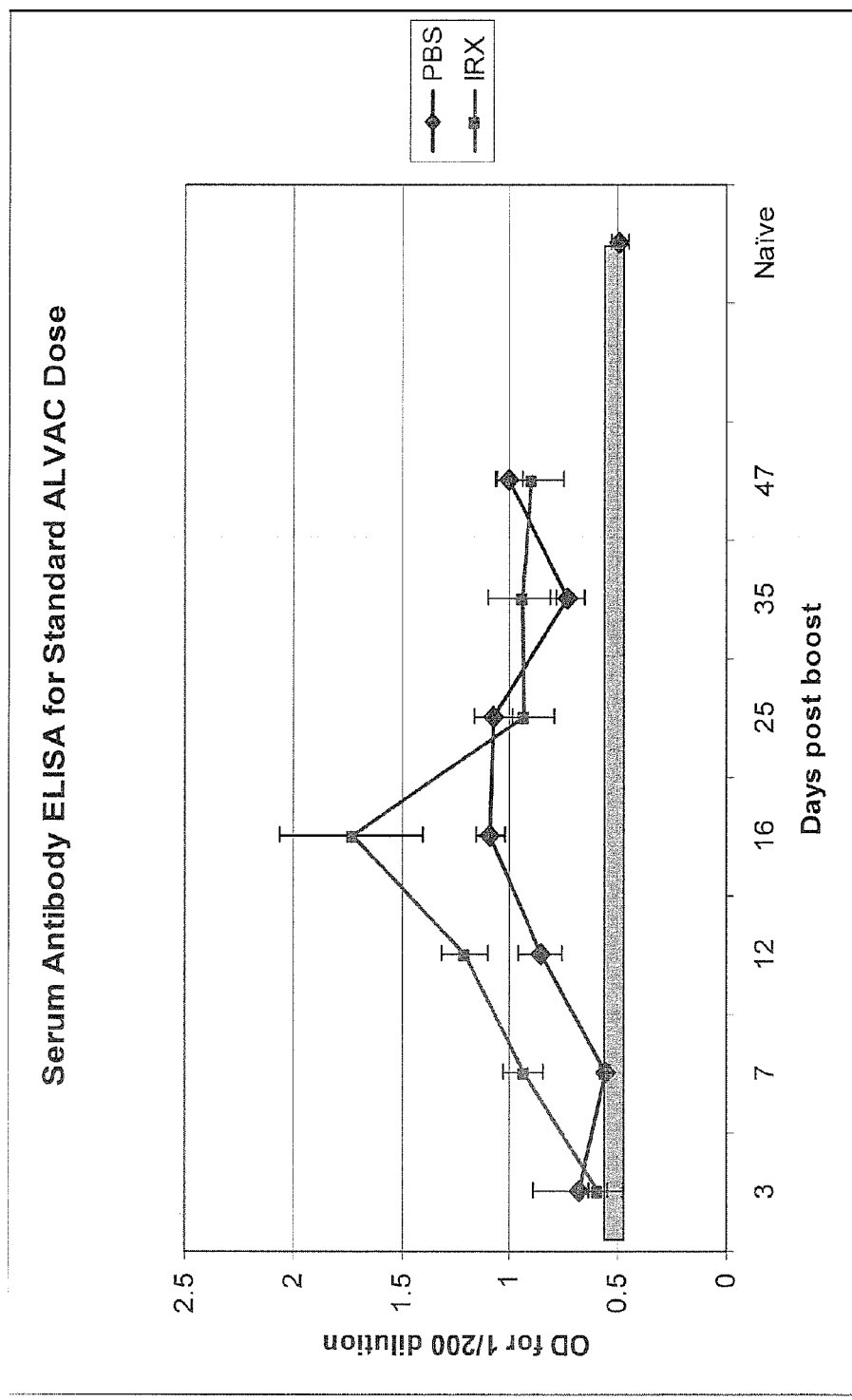
FIG. 46 is a graph of serum antibody response after vaccination with a viral-based vaccine and IRX-2.

IRX-2 Increases the Antibody Response after Vaccination with a Viral-Based Vaccine As shown in FIG. 46, the antibody response after vaccination with a viral vaccine was enhanced by the addition of IRX-2. IRX-2 consistently increased the peptide-specific T cell response compared to control at all time points.

IRX-2 increases the T Cell Response after Vaccination with a Viral-Based Vaccine.

Figure 47:
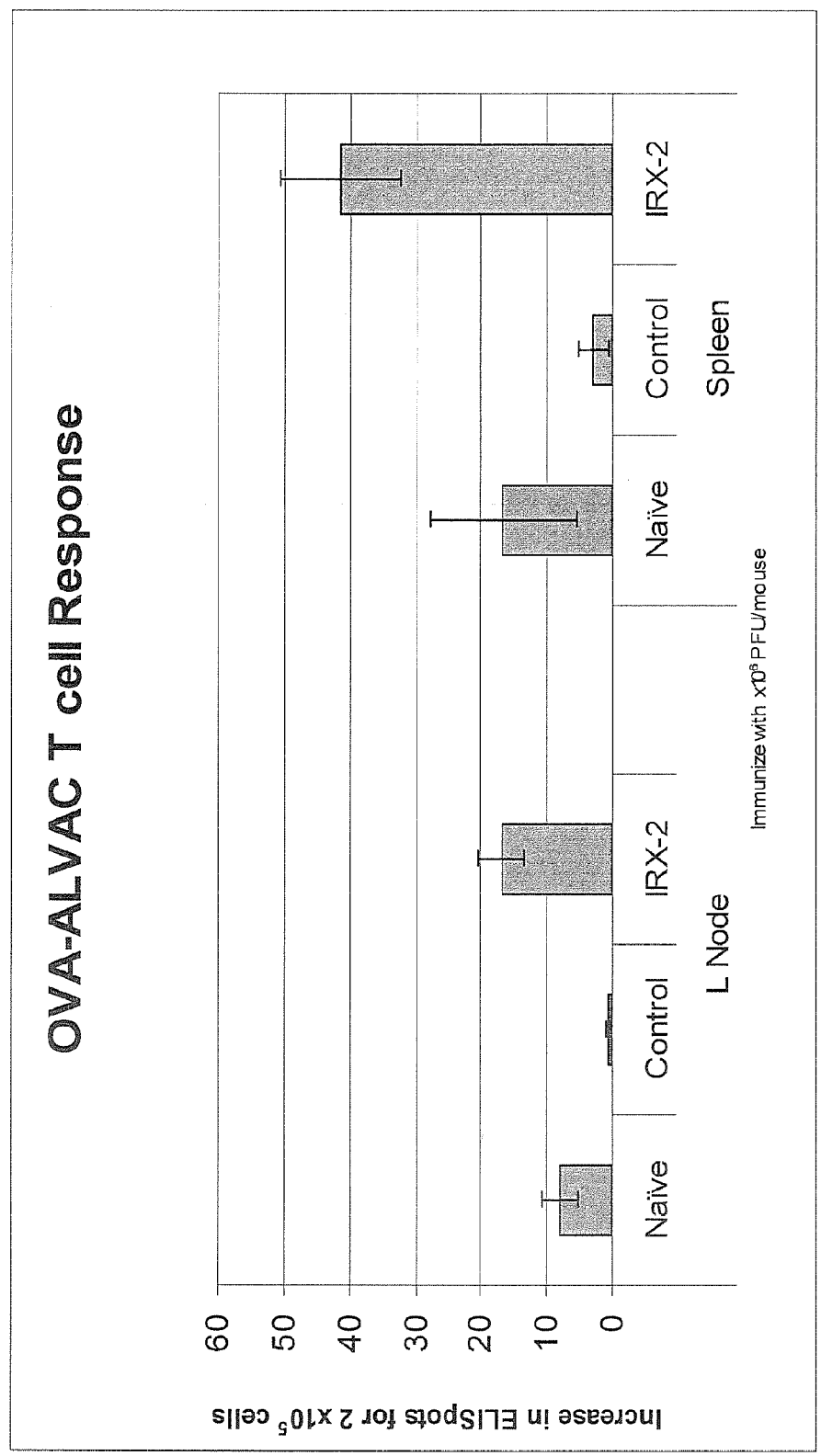
FIG. 47 is a graph of IFN-γ responses of T cells after vaccination with a viral-based vaccine and IRX-2.

As shown in FIG. 47, IRX-2 enhanced the antigen specific T cell response after vaccination with a viral-based vaccine.

IRX-2 enhances T Cell Responses after Vaccination with a Viral-Based Vaccine Expressing TRICOM.

IRX-2 enhanced the T cell responses to ice immunized with the lower doses of OVA-TriCom-ALVAC construct. The T cell response was dose dependent since the lower dose of OVA-TriCom-ALVAC gave a lower T cell response. As shown in FIG. 48, IRX-2 enhanced the T cell response compared to control for mice immunized with $3\times10^5$ pfu per mouse but not mice immunized with a higher dose of OVA-TriCom-ALVAC ($3\times10^6$ pfu per mouse).

Figure 49:
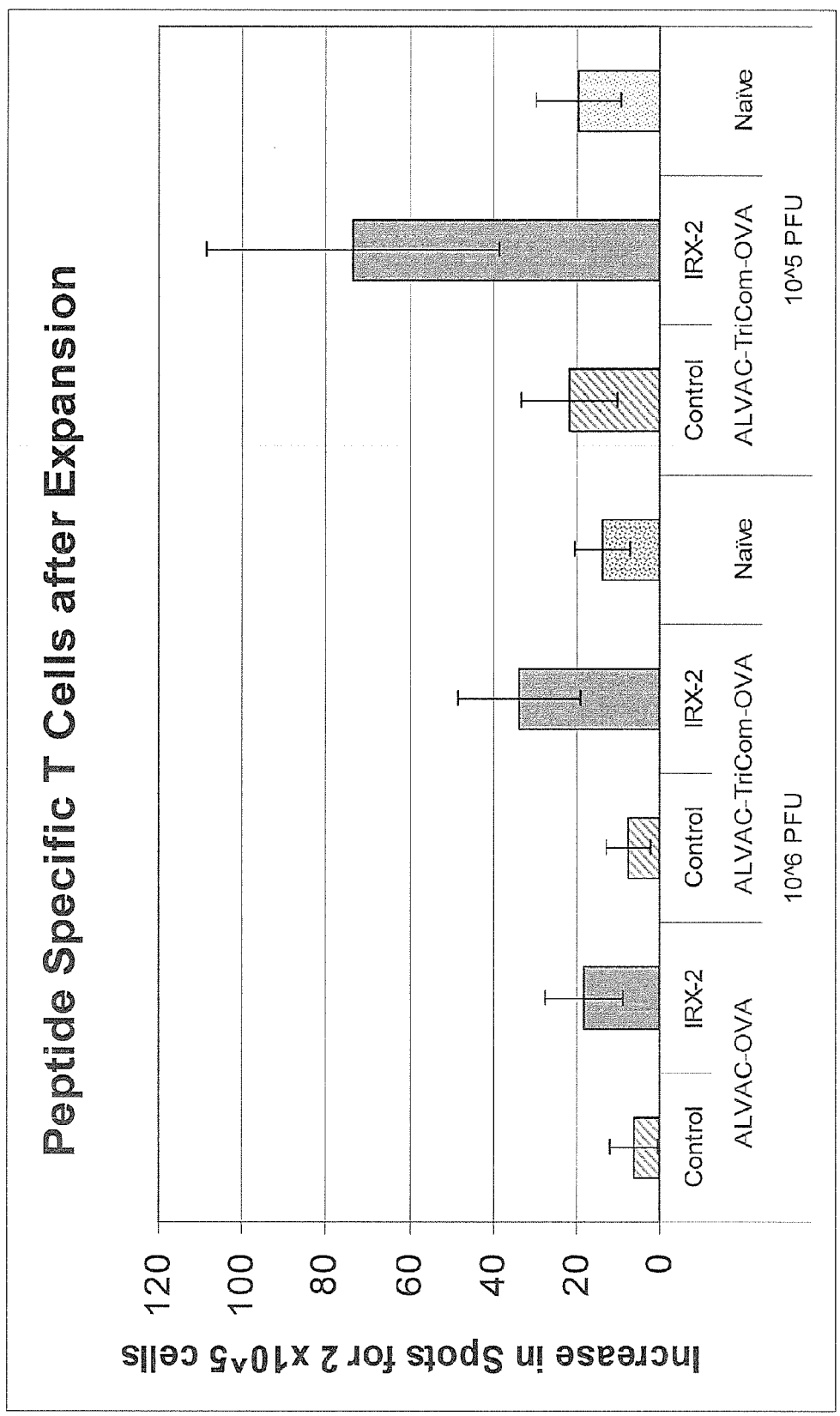
FIG. 49 is a graph of IFN-γ responses of T cells after vaccination with a viral-based vaccine and IRX-2.

IRX-2 Enhances the Expansion of Antigen-Specific Memory T Cells after Vaccination with a Viral-Based Vaccine As shown in FIG. 49, IRX-2 enhanced the peptide positive memory T cells compared to control. Both the $10^6$ PFU and $10^5$ PFU immunized mice had a stronger response when IRX-2 was included in the vaccine. The difference between the primary response and the expansion response for the higher dose of vaccine may be because the primary response measures active T cells while the expansion response focuses on the memory cells.

Figure 50:
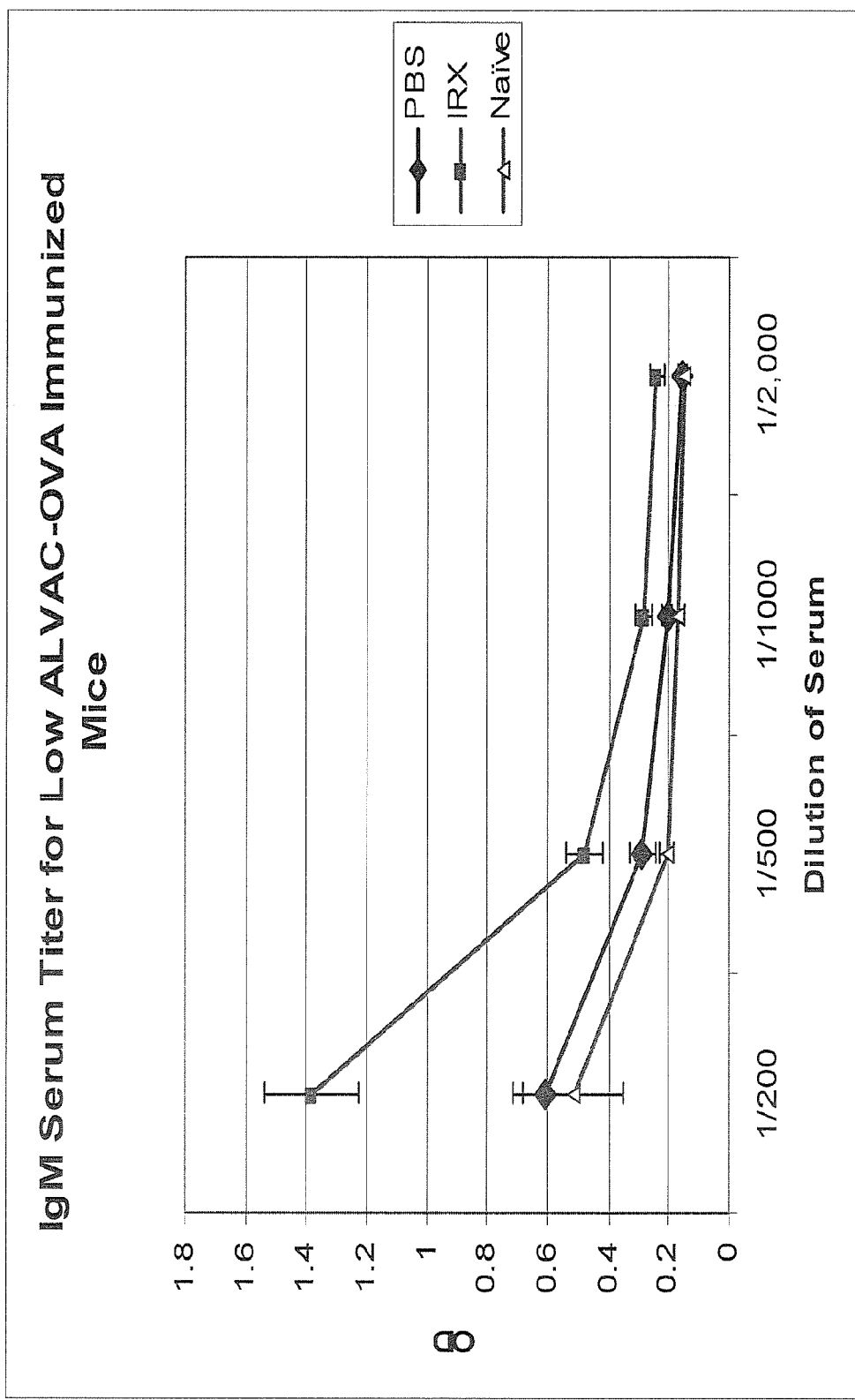
FIG. 50 is a graph of IgM responses after vaccination with a viral-based vaccine and IRX-2.

IRX-2 enhances IgM Antibody Responses after Vaccination with a Viral-Based Vaccine As shown in FIG. 50, IRX-2 enhances the response for ovalbumin specific IgM antibody at all times and doses of OVA-ALVAC.

Figure 51:
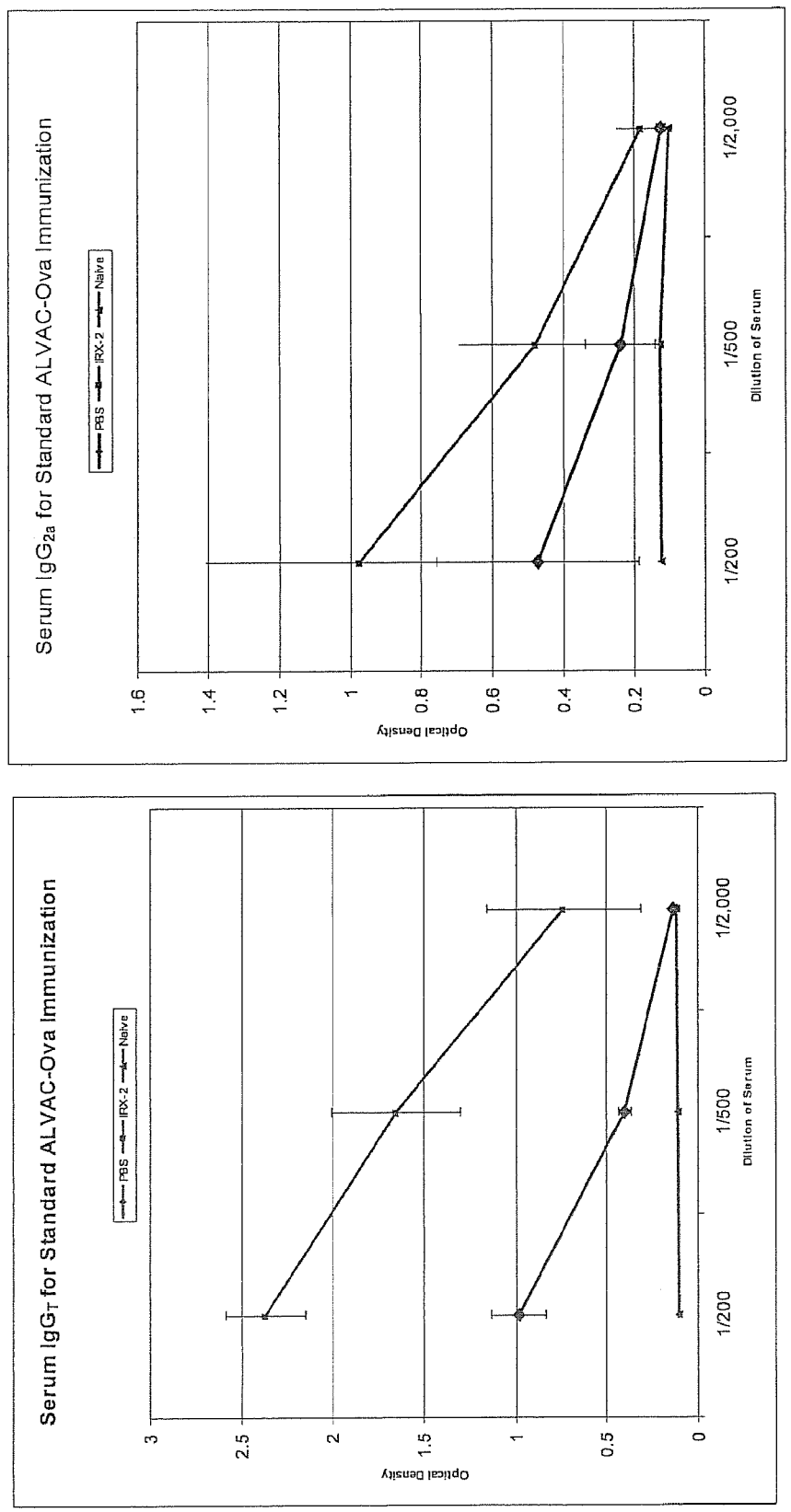
FIG. 51 is a graph of $IgG_1$ and $IgG2_A$ responses after vaccination with a viral-based vaccine and IRX-2.

IRX-2 Enhances $IgG_1$ and $IgG2_A$ Antibody Responses after Vaccination with a Viral-Based Vaccine As shown in FIG. 51 $IgG_1$ response and the $IgG2_A$ response were greater in IRX-2 immunized mice compared to control when plotted as dilution of serum vs OD.

Discussion

The results of this study point to IRX-2 as a powerful therapy that can be used to initiate a cellular immune response against exogenously administered tumor antigens in a cancer or infectious disease vaccine. IRX-2 administered with an irradiated PSMA expressing cell-based vaccine or a synthetic peptide conjugate vaccine was able to enhance in vivo T cell immune responses to these antigens. The novel nature of the IRX-2 activity was confirmed by comparing IRX-2 to other adjuvants, which were selected to represent various mechanisms of action. Alum was evaluated because it is a widely used FDA approved adjuvant, CpG because it is a TLR agonist that targets antigen presenting cells and the RIBI Adjuvant System (RAS) because it contains multiple adjuvant activities and is a safer alternative than Freund's adjuvant in mouse models. IRX-2 enhanced the peptide-specific DTH response to the conjugate vaccine but alum, CpG or RAS did not. The IRX-2 enhancement of the in vivo T cell peptide-specific DTH response was accompanied by enhanced T cell responses of spleen cells ex vivo to specific antigen as measured by IFN-γ secretion. These results also paralleled the antibody response to the peptides. While all adjuvants enhanced the antibody response as well as the DTH response to the protein carrier (as compared to PBS), only IRX-2 enhanced the antibody response to the peptides that were conjugated to the carrier. IRX-2 also enhanced the peptide specific antibody response when irradiated PSMA expressing cells were used as the immunogen. These observations are important because there is an 80% homology between the human and mouse protein and shows that tolerance to the peptides can be overcome by IRX-2 as compared to other adjuvants.

The studies reported here provide important preclinical data showing that IRX-2 enhances T cell immune responses to exogenous antigens and can be used in combination with multiple antigen types in therapeutic cancer vaccines. The unique nature of the T cell peptide-specific response to both the irradiated cell and conjugate vaccine is a result of the multi-target mode of action of IRX-2 and the synergy among the cytokines. IRX-2 provides a T cell adjuvant platform that results in a vaccine with multiple activities including not only increased antigen presentation but also stimulation of subsequent T cell differentiation, proliferation and migration to the periphery. The cytokines also shift the DC tolerance or regulatory T cell balance towards activation of the response to T cell epitopes and enhance the production of memory T cells. IRX-2 also enhances the T cell helper epitopes in the carrier or irradiated cells providing additional stimulation of the development of an effective T cell response.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

What is claimed is:

1. A composition for enhancing an immune response in a patient, comprising:
    (a) a primary cell-derived biologic comprising the cytokines IL-1, IL-2, IL-6, IL-8, TNF-α, and IFN-γ; and
    (b) a composition comprising at least one adjuvant selected from the group consisting of CpG, polyI:C and recombinant IFN-γ,
    wherein the combination of (a) and (b) acts synergistically to enhance the immune response in the patient.

2. The composition of claim 1, wherein the composition in (b) comprises CpG, polyI:C and recombinant IFN-γ.

3. The composition of claim 1, wherein the primary cell-derived biologic comprises 60-6,000 picograms/mL of IL-1, 600-60,000 picograms/mL of IL-2, 60-6,000 picograms/mL of IL-6, 6,000-600,000 picograms/mL of IL-8, 200-20,000 picograms/mL of TNF-α, and 200-20,000 picograms/mL of IFN-γ.

4. A method of enhancing an immune response in a patient, comprising administering the composition of claim 1 to the patient, wherein the combination of (a) and (b) acts synergistically to enhance the immune response in the patient.

5. The method of claim 4, further including the step of administering at least one exogenous antigen.

6. The method of claim 4, wherein the composition in (b) comprises CpG, polyI:C and recombinant IFN-γ.

7. The method of claim 4, wherein the primary cell-derived biologic comprises 60-6,000 picograms/mL of IL-1, 600-60,000 picograms/mL of IL-2, 60-6,000 picograms/mL of IL-6,000-600,000picograms/mL of IL-8, 200-20,000 picograms/mL of TNF-α, and 200-20,000 picograms/mL of IFN-γ.

8. A method of enhancing an immune response in a patient, comprising administering to the patient:
    (a) a primary cell-derived biologic comprising the cytokines IL-1, IL-2, IL-6, IL-8, TNF-α, and IFN-γ; and
    (b) a composition comprising at least one adjuvant selected from the group consisting of CpG, polyI:C and recombinant IFN-γ,
    wherein the combination of (a) and (b) acts synergistically to enhance the immune response in the patient, and wherein (a) and (b) are administered separately.

9. The method of claim 8, wherein the composition in (b) comprises CpG, polyI:C and recombinant IFN-γ.

10. The method of claim 8, wherein the primary cell-derived biologic comprises 60-6,000 picograms/mL of IL-1, 600-60,000 picograms/mL of IL-2, 60-6,000 picograms/mL of IL-6, 6,000-600,000 picograms/mL of IL-8, 200-20,000 picograms/mL of TNF-α, and 200-20,000picograms/mL of IFN-γ.

11. The method of claim 8, further including the step of administering at least one exogenous antigen.

* * * * *